United States Patent
Kauffmann-Hefner et al.

(10) Patent No.: US 8,865,702 B2
(45) Date of Patent: Oct. 21, 2014

(54) B1-ANTAGONISTS

(75) Inventors: Iris Kauffmann-Hefner, Attenweiler (DE); Angelo Ceci, Mittelbiberach (DE); Henri Doods, Warthausen (DE); Norbert Hauel, Schemmerhofen (DE); Ingo Konetzki, Warthausen (DE); Annette Schuler-Metz, Ulm (DE); Rainer Walter, Biberach (DE)

(73) Assignee: Boehringer Ingelheim International GmbH, Ingelheim am Rhein (DE)

( * ) Notice: Subject to any disclaimer, the term of this patent is extended or adjusted under 35 U.S.C. 154(b) by 199 days.

(21) Appl. No.: 12/669,970

(22) PCT Filed: Jul. 23, 2008

(86) PCT No.: PCT/EP2008/059622
§ 371 (c)(1),
(2), (4) Date: Mar. 18, 2010

(87) PCT Pub. No.: WO2009/013299
PCT Pub. Date: Jan. 29, 2009

(65) Prior Publication Data
US 2010/0197664 A1    Aug. 5, 2010

(30) Foreign Application Priority Data

Jul. 25, 2007   (DE) .................. 10 2007 034 620

(51) Int. Cl.
| | | |
|---|---|---|
| *C07D 223/16* | (2006.01) | |
| *C07D 401/14* | (2006.01) | |
| *C07D 217/06* | (2006.01) | |
| *C07D 487/04* | (2006.01) | |
| *C07D 471/10* | (2006.01) | |
| *C07D 211/58* | (2006.01) | |
| *C07D 209/40* | (2006.01) | |
| *C07D 209/44* | (2006.01) | |

(52) U.S. Cl.
CPC ............ *C07D 401/14* (2013.01); *C07D 217/06* (2013.01); *C07D 487/04* (2013.01); *C07D 471/10* (2013.01); *C07D 223/16* (2013.01); *C07D 211/58* (2013.01); *C07D 209/40* (2013.01); *C07D 209/44* (2013.01)
USPC ................ 514/217.01; 514/316; 514/253.09; 514/307; 514/254.01; 514/278; 544/364; 544/372; 546/16; 546/146; 546/187; 540/594

(58) Field of Classification Search
None
See application file for complete search history.

(56) References Cited

U.S. PATENT DOCUMENTS

| | | |
|---|---|---|
| 7,291,642 B2 | 11/2007 | Kauffmann-Hefner et al. |
| 8,372,838 B2 | 2/2013 | Hauel et al. |
| 8,450,306 B2 | 5/2013 | Hauel et al. |
| 2006/0100219 A1 | 5/2006 | Kauffmann-Hefner et al. |
| 2006/0178360 A1 | 8/2006 | Barth et al. |
| 2010/0197664 A1 | 8/2010 | Kauffmann-Hefner et al. |
| 2011/0263626 A1 | 10/2011 | Hauel et al. |
| 2012/0208823 A1 | 8/2012 | Hauel et al. |
| 2014/0038977 A1 | 2/2014 | Hauel et al. |

FOREIGN PATENT DOCUMENTS

| | | | | |
|---|---|---|---|---|
| CA | 2790952 A1 | 9/2011 | | |
| WO | WO 2004087700 | * 10/2004 | ........... | C07D 471/04 |
| WO | 2007140383 | * 12/2007 | ......... | A61K 31/5415 |
| WO | 2008/046753 A1 | 4/2008 | | |
| WO | 2009013299 A2 | 1/2009 | | |
| WO | 2009021946 A1 | 2/2009 | | |
| WO | 2009027450 A1 | 3/2009 | | |
| WO | 2011104203 A1 | 9/2011 | | |
| WO | 2012022794 A1 | 2/2012 | | |
| WO | 2012022795 A1 | 2/2012 | | |

OTHER PUBLICATIONS

Chen, J.,"Targeting the bradykinin B1 receptor to reduce pain." Expert Opinion on Therapeutic Targets (2007) 11(1): 21-35.*
Caplus: Kravchenko, D.V., "Synthesis of substituted 4-oxo-7-sulfamoyl-2,3,4,5-tetrahydrobenzo(b)(1,4) thiazepines". 2005.
International Search Report for PCT/EP2008/059622 mailed Feb. 2, 2009.
Marceau, F. "A possible common pharmacophore int he non-peptide antagonists of the bradykinin B1 receptor". Trends in Pharmacological Sciences, Elsevier, Hayworth, GB, Bd26, No. 3, Mar. 1, 2005, pp. 116-118.
Shalygina, E.E., et al., "The synthesis, structure and properties of the sulfamide derivative 2-methyl-indoline series containing a piperdine or piperazine fragment", Chemistry and Chemical Technology (Khimiya I Khimicheskaya Tekhnologiya), vol. 48, 2005, pp. 66-69.
Kravchenko, D.V., et al., "The synthesis of substitituted 4-Oxo-7-sulfamoyl-2,3,4,5-tertrahydro-benzo(b)(1.4) thiazepin", Chemistry and Chemical Technology (Khimiya I Khimicheskaya Tekhnologiya), vol. 48, Issue 5, 2005, pp. 123-131.

* cited by examiner

*Primary Examiner* — Noble Jarrell
*Assistant Examiner* — John Mauro
(74) *Attorney, Agent, or Firm* — Michael P. Morris; Anthony P. Bottino

(57) ABSTRACT

Disclosed are compounds of the formula I $$R^5-R^4-A-R^3\underset{O}{\overset{}{\diagdown}}\underset{}{\overset{Y}{\diagup}}\underset{R^2}{\overset{}{N}}\underset{}{\overset{O}{\underset{O}{\diagdown S\diagup}}}R^1,\qquad(I)$$

wherein A, Y, $R^1$, $R^2$, $R^3$, $R^4$ and $R^5$ are defined, suitable for treating diseases and symptoms of diseases caused at least to some extent by stimulation of bradykinin-B1 receptors, the preparation thereof and the use thereof.

22 Claims, No Drawings

B1-ANTAGONISTS

APPLICATION DATA

This application is the national phase entry under 35 U.S.C. §371 of International Application No. PCT/EP2008/059622, filed Jul. 23, 2008, which claims priority to German Patent Application No. DE102007034620.6, filed Jul. 25, 2007, which is hereby incorporated by reference in its entirety.

The present invention relates to compounds of general formula I

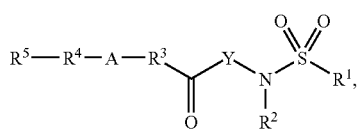

wherein A, Y, $R^1$, $R^2$, $R^3$, $R^4$ and $R^5$ are defined as in claim 1, the enantiomers, the diastereomers, the mixtures thereof and the salts thereof, particularly the physiologically acceptable salts thereof with organic or inorganic acids or bases, which have valuable properties, the preparation thereof, the pharmaceutical compositions containing the pharmacologically effective compounds, the preparation thereof and the use thereof.

DETAILED DESCRIPTION OF THE INVENTION

In the above general formula I in a first embodiment

A denotes
  a) a bond,
  b) $C_{1-4}$-alkylene,
  c) —N($R^2$),
  d) —C(O),
  e) a saturated 5- or 6-membered aza heterocyclic group or
  f) a saturated 6- or 7-membered diaza heterocyclic group, Y denotes a $C_{1-6}$-alkylene group optionally substituted by the group $R^2$, while a methylene group contained therein may additionally be replaced by $Y^1$ and $Y^1$ denotes —O—, —S—, —S(O)—, —N($R^2$), —N($R^2$)—C(O), —C(O)—N($R^2$), —C(O), —CH(aryl) or —S(O)$_2$—, $R^1$ denotes
  a) aryl or
  b) heteroaryl,
  while the previously mentioned aryl and heteroaryl groups may each be substituted by one, two, three or four groups $R^{1.1}$ and the groups $R^{1.1}$ may be identical or different and
  $R^{1.1}$ denotes H, F, Cl, Br, I, $C_{1-3}$-alkyl, $F_3C$, HO, $C_{1-3}$-alkyl-O or $C_{1-3}$-alkyl-O—$C_{2-4}$-alkylene-O—, $R^2$ denotes
  a) H or
  b) $C_{1-3}$-alkyl, while each methylene group may be substituted by up to two and each methyl group may be substituted by up to three fluorine atoms, $R^3$ denotes
  a) a saturated 4- to 7-membered aza heterocyclic group which is selected from among

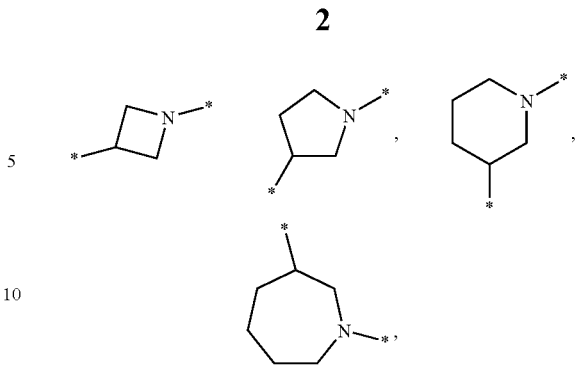

b) a monounsaturated 5- to 7-membered aza heterocyclic group, wherein an olefinic double bond is fused to a group $R^{3.1}$, or
  c) a saturated 8- to 10-membered diaza-heterobicyclic group, and $R^{3.1}$ denotes phenyl or pyridyl,
  while the groups $R^{3.1}$ in the carbon skeleton may additionally be substituted by one, two or three identical or different groups $R^{3.1.1}$ and
  $R^{3.1.1}$ denotes F, Cl, Br, I, $H_3C$ or $F_3C$—, $R^4$ denotes
  a) a bond,
  b) $C_{1-3}$-alkylene
  c) $C_{3-6}$-cycloalkylene,
  d) a saturated 4- to 7-membered aza heterocyclic group,
  e) a saturated 6- to 7-membered diaza heterocyclic group or
  f) a saturated 9- to 11-membered diaza-spirocycle, $R^5$ denotes
  a) a $C_{1-4}$-alkyl group substituted by $R^{5.1}$,
  b) $H_2N$,
  c) $C_{1-4}$-alkyl-NH—
  d) ($C_{1-4}$-alkyl)$_2$N or
  e) a saturated 4- to 6-membered aza heterocyclic group and
  $R^{5.1}$ denotes H, ($C_{1-4}$-alkyl)$_2$N or a saturated 4- to 6-membered aza heterocyclic group, the enantiomers, the diastereomers, the mixtures thereof and the salts thereof, particularly the physiologically acceptable salts thereof with organic or inorganic acids or bases.

A second embodiment of the present invention consists of the compounds of the above general formula I, wherein A, Y, $R^2$, $R^3$, $R^4$ and $R^5$ are defined as hereinbefore in the first embodiment and $R^1$ denotes an aryl group which is substituted in each case by one, two, three or four groups $R^{1.1}$, while the groups $R^{1.1}$ may be identical or different and
  $R^{1.1}$ denotes H, F, Cl, Br, I, $C_{1-3}$-alkyl, $F_3C$, HO, $C_{1-3}$-alkyl-O or $C_{1-3}$-alkyl-O—$C_{2-4}$-alkylene-O—, the enantiomers, the diastereomers, the mixtures thereof and the salts thereof, particularly the physiologically acceptable salts thereof with organic or inorganic acids or bases.

A third embodiment of the present invention consists of the compounds of the above general formula I, wherein A, Y, $R^2$, $R^3$, $R^4$ and $R^5$ are defined as hereinbefore in the first embodiment and

3

R¹ denotes a group selected from

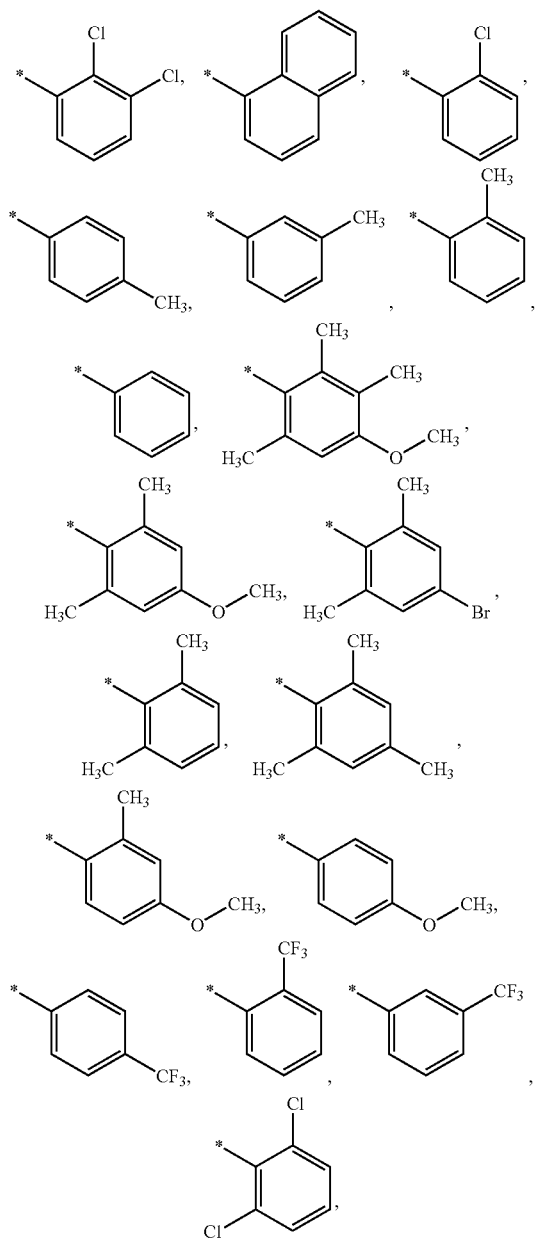

the enantiomers, the diastereomers, the mixtures thereof and the salts thereof, particularly the physiologically acceptable salts thereof with organic or inorganic acids or bases.

A fourth embodiment of the present invention consists of the compounds of the above general formula I, wherein A, Y, R², R³, R⁴ and R⁵ are defined as hereinbefore in the first embodiment and R¹ denotes the group

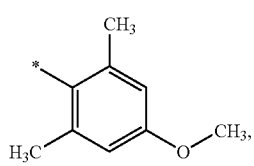

4 the enantiomers, the diastereomers, the mixtures thereof and the salts thereof, particularly the physiologically acceptable salts thereof with organic or inorganic acids or bases.

A fifth embodiment of the present invention consists of the compounds of the above general formula I, wherein A, Y, R¹, R³, R⁴ and R⁵ are defined as hereinbefore in the first embodiment and R² denotes a) H or b) H₃C—, the enantiomers, the diastereomers, the mixtures thereof and the salts thereof, particularly the physiologically acceptable salts thereof with organic or inorganic acids or bases.

A sixth embodiment of the present invention consists of the compounds of general formula I, wherein A, R¹, R², R³, R⁴ and R⁵ are defined as hereinbefore in the first embodiment and Y denotes $C_{1-4}$-alkylene or a group selected from

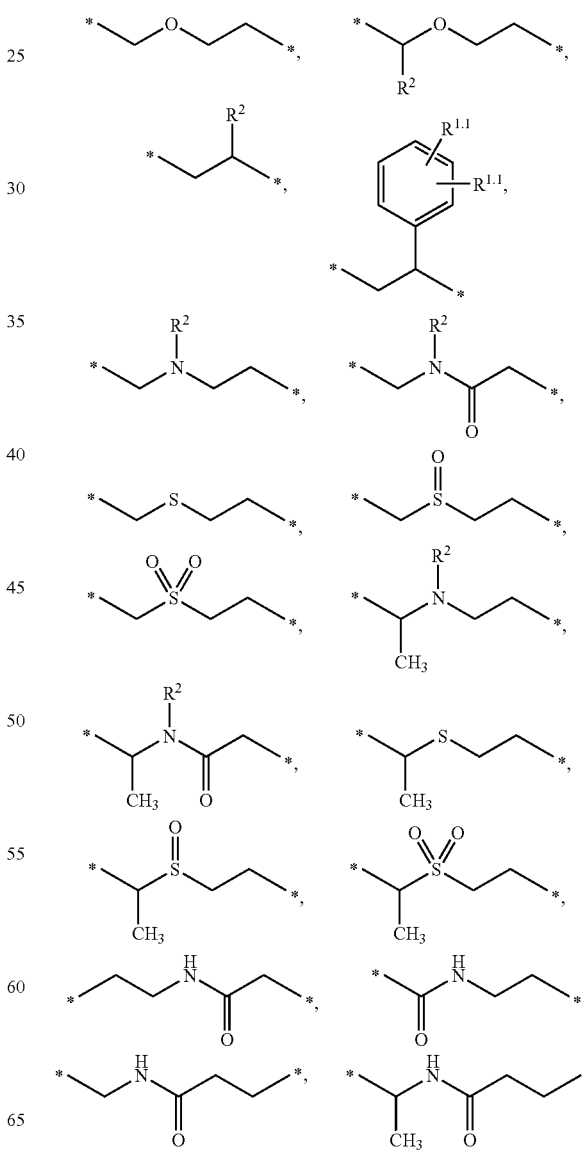

-continued

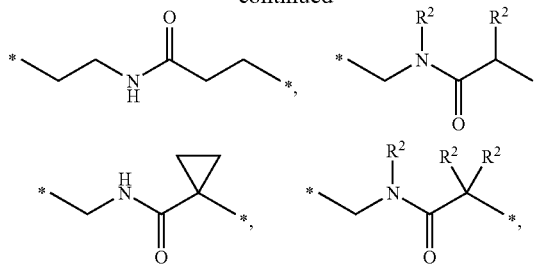

the enantiomers, the diastereomers, the mixtures thereof and the salts thereof, particularly the physiologically acceptable salts thereof with organic or inorganic acids or bases.

A seventh embodiment of the present invention consists of the compounds of general formula I, wherein A, $R^1$, $R^2$, $R^3$, $R^4$ and $R^5$ are defined as hereinbefore in the first embodiment and Y denotes a group selected from

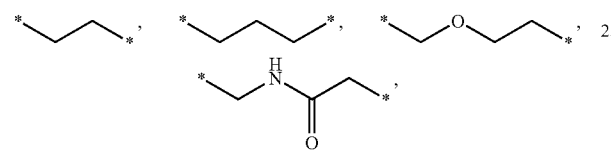

the enantiomers, the diastereomers, the mixtures thereof and the salts thereof, particularly the physiologically acceptable salts thereof with organic or inorganic acids or bases.

An eighth embodiment of the present invention consists of the compounds of general formula I, wherein A, Y, $R^1$, $R^2$, $R^4$ and $R^5$ are defined as hereinbefore in the first embodiment and $R^3$ denotes a saturated 4- to 7-membered aza heterocyclic group which is selected from among

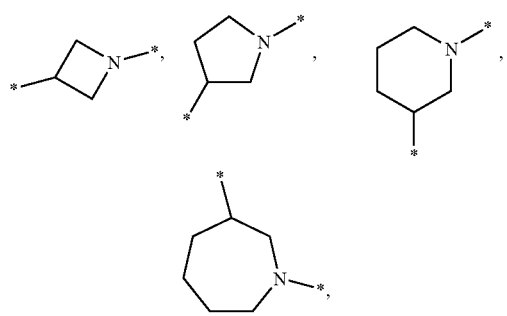

the enantiomers, the diastereomers, the mixtures thereof and the salts thereof, particularly the physiologically acceptable salts thereof with organic or inorganic acids or bases.

A ninth embodiment of the present invention consists of the compounds of general formula I, wherein A, Y, $R^1$, $R^2$, $R^4$ and $R^5$ are defined as hereinbefore in the first embodiment and $R^3$ denotes a monounsaturated 5- to 7-membered aza heterocyclic group, wherein an olefinic double bond is fused to a phenyl or pyridyl group which is selected from among

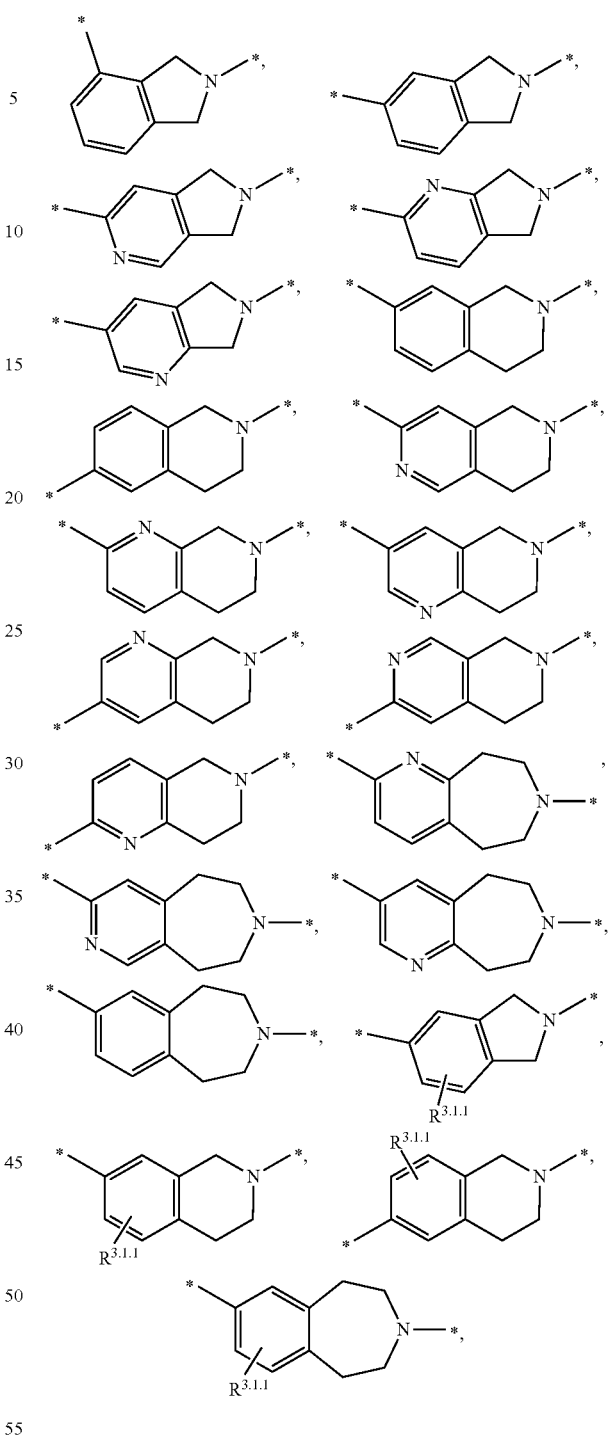

wherein $R^{3.1.1}$ denotes F, Cl, Br, I, $H_3C$ or $F_3C-$, the enantiomers, the diastereomers, the mixtures thereof and the salts thereof, particularly the physiologically acceptable salts thereof with organic or inorganic acids or bases.

A tenth embodiment of the present invention consists of the compounds of general formula I, wherein A, Y, $R^1$, $R^2$, $R^4$ and $R^5$ are defined as hereinbefore in the first embodiment and $R^3$ denotes a saturated 8- to 10-membered diaza-heterobicyclic group which is selected from among

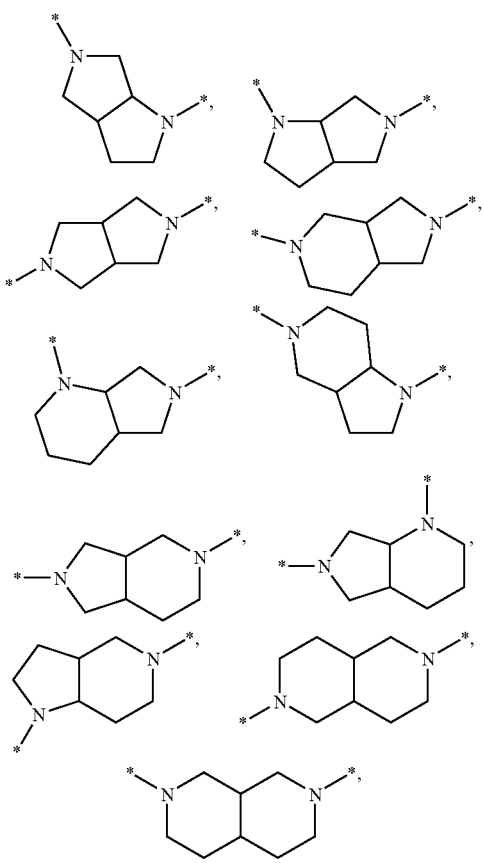

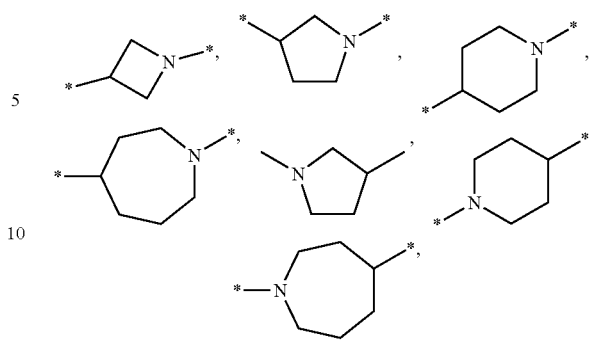

the enantiomers, the diastereomers, the mixtures thereof and the salts thereof, particularly the physiologically acceptable salts thereof with organic or inorganic acids or bases.

An eleventh embodiment of the present invention consists of the compounds of the above general formula I, wherein A, Y, $R^1$, $R^2$, $R^3$ and $R^5$ are defined as hereinbefore in the first embodiment and $R^4$ denotes a bond, the enantiomers, the diastereomers, the mixtures thereof and the salts thereof, particularly the physiologically acceptable salts thereof with organic or inorganic acids or bases.

A twelfth embodiment of the present invention consists of the compounds of the above general formula I, wherein A, Y, $R^1$, $R^2$, $R^3$ and $R^5$ are defined as hereinbefore in the first embodiment and $R^4$ denotes a $C_{1-3}$-alkylene group, the enantiomers, the diastereomers, the mixtures thereof and the salts thereof, particularly the physiologically acceptable salts thereof with organic or inorganic acids or bases.

A thirteenth embodiment of the present invention consists of the compounds of the above general formula I, wherein A, Y, $R^1$, $R^2$, $R^3$ and $R^5$ are defined as hereinbefore in the first embodiment and $R^4$ denotes a $C_{3-6}$-cycloalkylene group, the enantiomers, the diastereomers, the mixtures thereof and the salts thereof, particularly the physiologically acceptable salts thereof with organic or inorganic acids or bases.

A fourteenth embodiment of the present invention consists of the compounds of the above general formula I, wherein A, Y, $R^1$, $R^2$, $R^3$ and $R^5$ are defined as hereinbefore in the first embodiment and $R^4$ denotes a saturated 4- to 7-membered aza heterocyclic group which is selected from among the enantiomers, the diastereomers, the mixtures thereof and the salts thereof, particularly the physiologically acceptable salts thereof with organic or inorganic acids or bases.

A fifteenth embodiment of the present invention consists of the compounds of the above general formula I, wherein A, Y, $R^1$, $R^2$, $R^3$ and $R^5$ are defined as hereinbefore in the first embodiment and $R^4$ denotes a saturated 6- to 7-membered diaza heterocyclic group selected from among

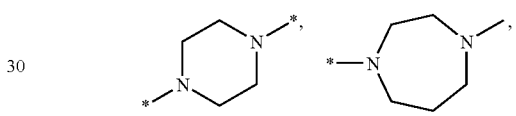

the enantiomers, the diastereomers, the mixtures thereof and the salts thereof, particularly the physiologically acceptable salts thereof with organic or inorganic acids or bases.

A sixteenth embodiment of the present invention consists of the compounds of the above general formula I, wherein A, Y, $R^1$, $R^2$, $R^3$ and $R^5$ are defined as hereinbefore in the first embodiment and $R^4$ denotes a saturated 9- to 11-membered diaza-spirocycle selected from among

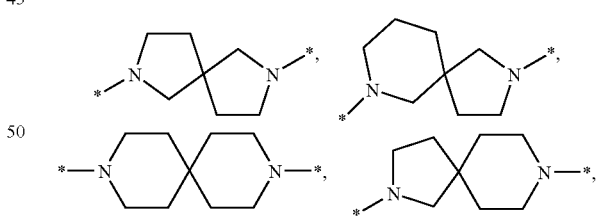

the enantiomers, the diastereomers, the mixtures thereof and the salts thereof, particularly the physiologically acceptable salts thereof with organic or inorganic acids or bases.

A seventeenth embodiment of the present invention consists of the compounds of general formula I wherein A denotes a) a bond, b) $C_{1-4}$-alkylene, c) —N($R^2$), d) —C(O), e) a heterocyclic group which is selected from among
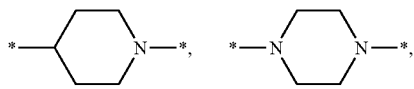
Y denotes C$_{1-4}$-alkylene or a group selected from
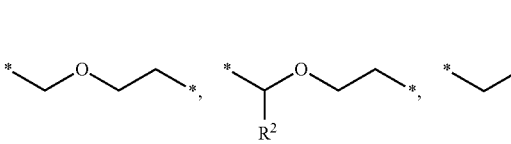
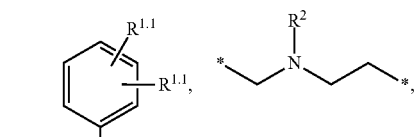
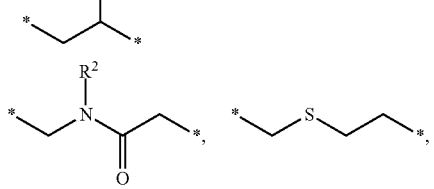
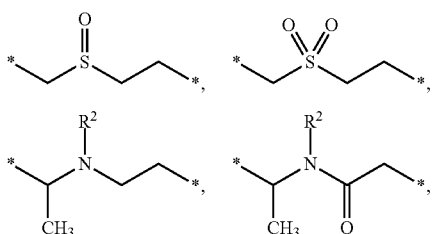
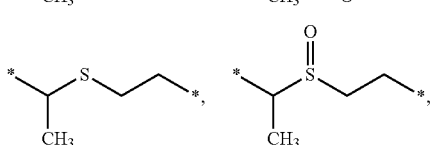
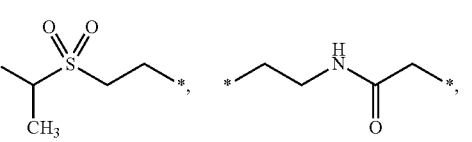
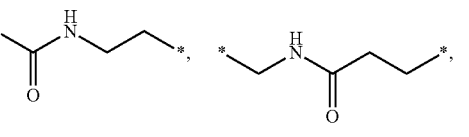
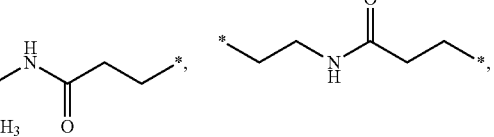
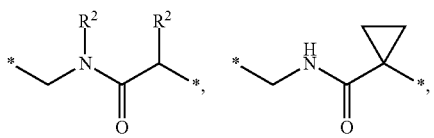
-continued
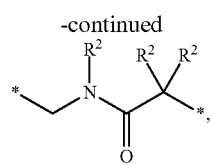
R$^1$ denotes a group selected from
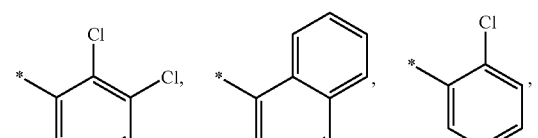
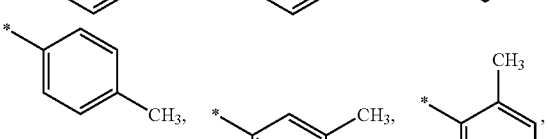
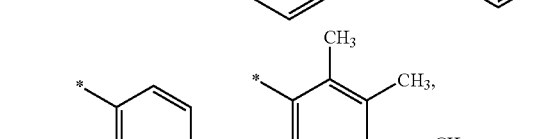
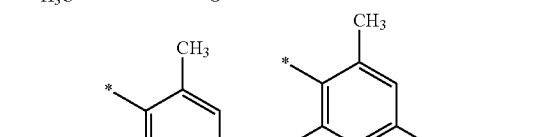
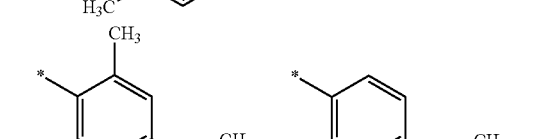
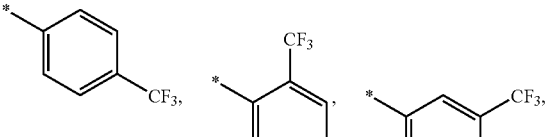
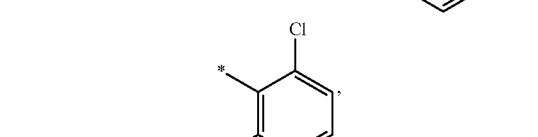
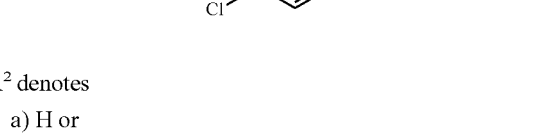
R$^2$ denotes
a) H or
b) H$_3$C, R³ denotes a group selected from
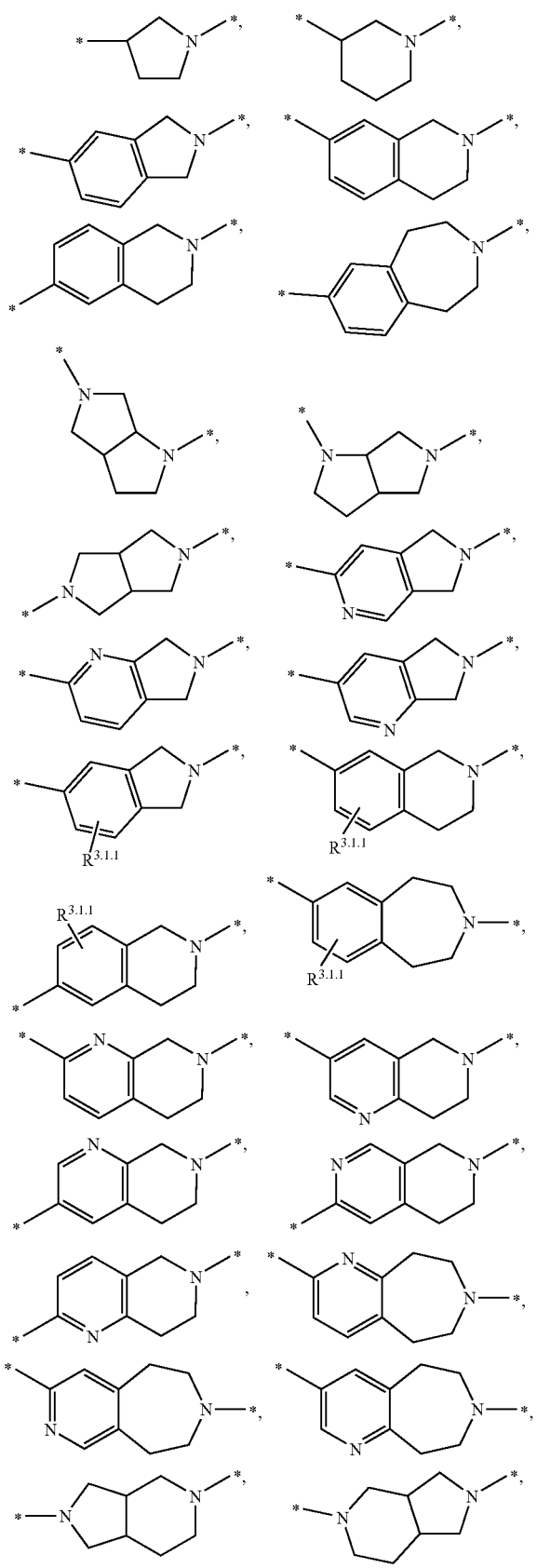
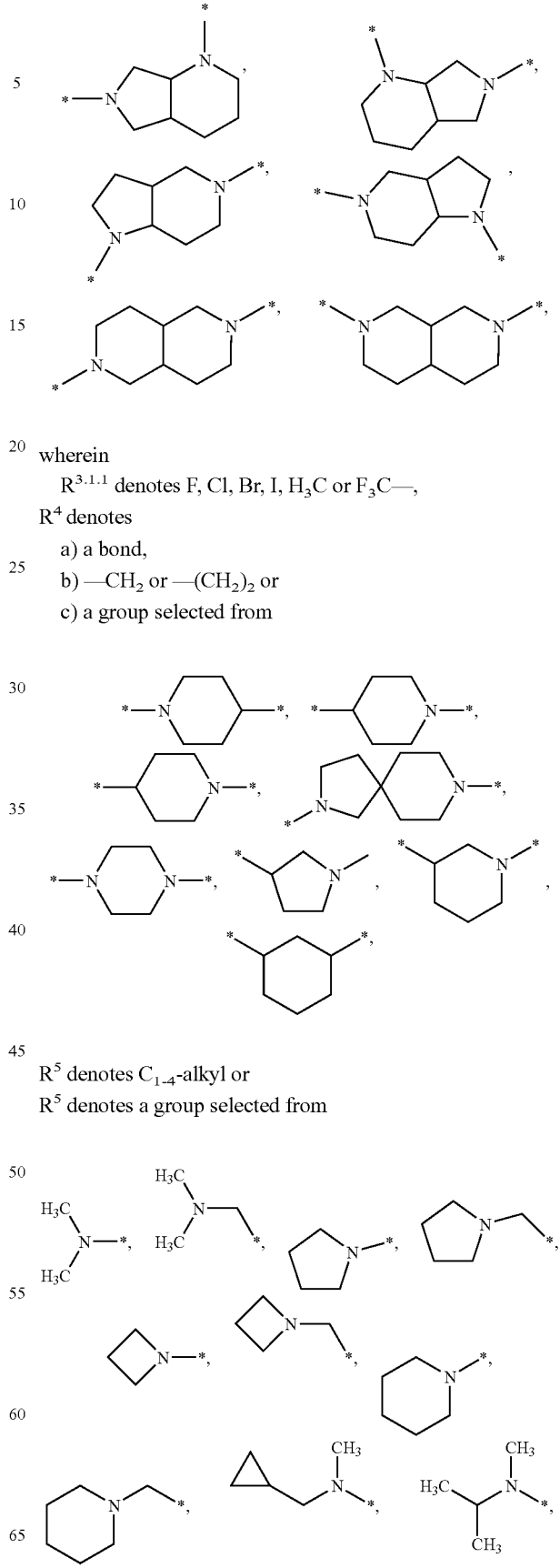
wherein
R³·¹·¹ denotes F, Cl, Br, I, H₃C or F₃C—,
R⁴ denotes
  a) a bond,
  b) —CH₂ or —(CH₂)₂ or
  c) a group selected from
R⁵ denotes $C_{1-4}$-alkyl or
R⁵ denotes a group selected from -continued

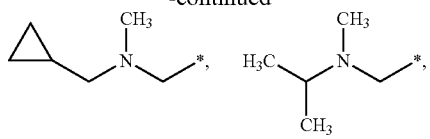

the enantiomers, the diastereomers, the mixtures thereof and the salts thereof, particularly the physiologically acceptable salts thereof with organic or inorganic acids or bases.

An eighteenth embodiment of the present invention consists of the compounds of general formula I wherein
A denotes
  a) a bond,
  b) —CH$_2$ or —(CH$_2$)$_2$,
  c) —N(R$^2$),
  d) —C(O),
  e) a heterocyclic group which is selected from among

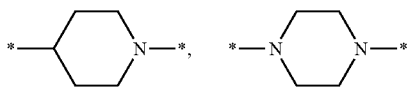

Y denotes a group selected from

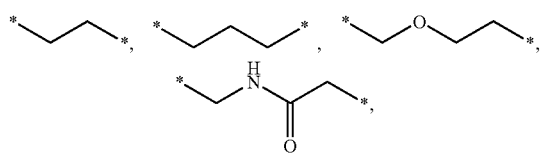

R$^1$ denotes the group

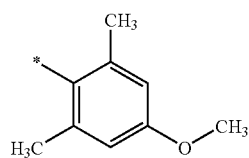

R$^2$ denotes
  a) H or
  b) H$_3$C,
R$^3$ denotes a group selected from

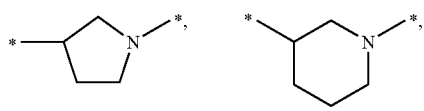

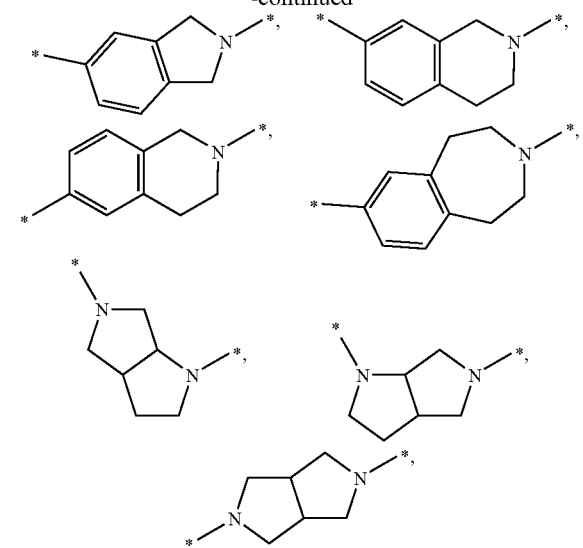

R$^4$ denotes
  a) a bond,
  b) —CH$_2$ or —(CH$_2$)$_2$ or
  b) a group selected from

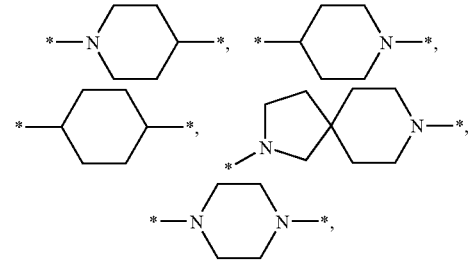

R$^5$ denotes a group selected from

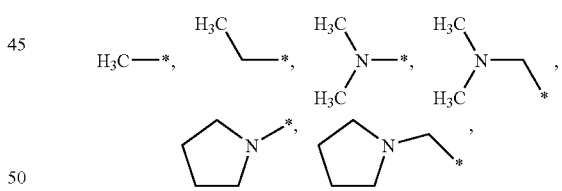

the enantiomers, the diastereomers, the mixtures thereof and the salts thereof, particularly the physiologically acceptable salts thereof with organic or inorganic acids or bases.

The following are mentioned as examples of most particularly preferred compounds of the above general formula I:

| Example | Structure |
|---------|-----------|
| (1) | ![structure] |

| Example | Structure |
|---|---|
| (2) | 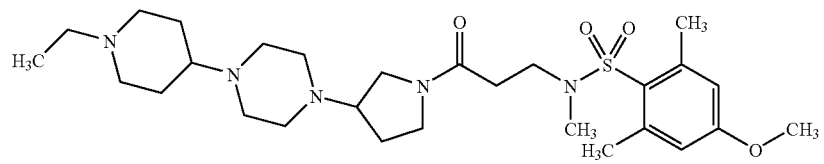 |
| (3) | 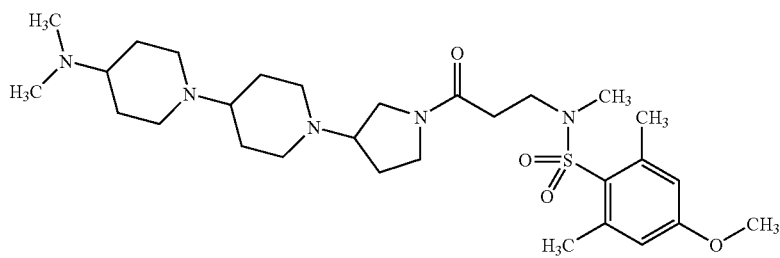 |
| (4) | 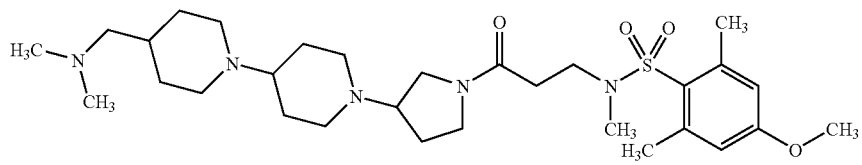 |
| (5) | 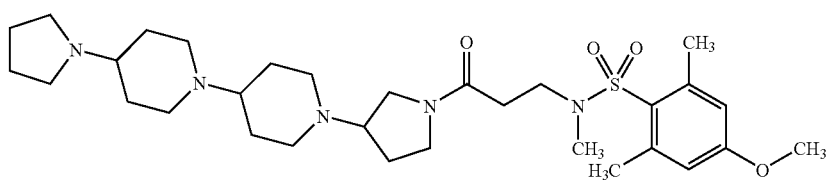 [SMILES: COc1cc(C)c(S(=O)(=O)N(C)CCC(=O)N2CCC(N3CCC(N4CCC(N5CCCC5)CC4)CC3)C2)c(C)c1] |
| (6) | 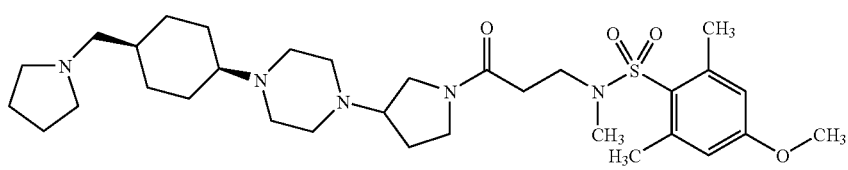 [SMILES: COc1cc(C)c(S(=O)(=O)N(C)CCC(=O)N2CCC(N3CCN([C@H]4CC[C@@H](CN5CCCC5)CC4)CC3)C2)c(C)c1] |
| (7) | 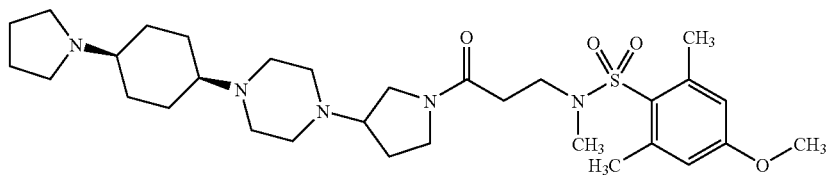 [SMILES: COc1cc(C)c(S(=O)(=O)N(C)CCC(=O)N2CCC(N3CCN([C@H]4CC[C@@H](N5CCCC5)CC4)CC3)C2)c(C)c1] |
| (8) | 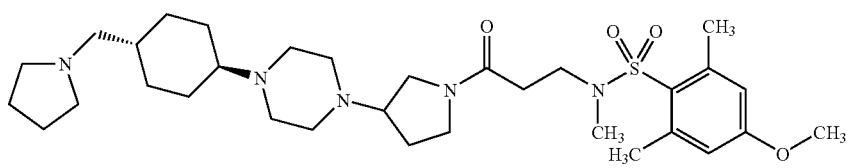 |
| (9) | 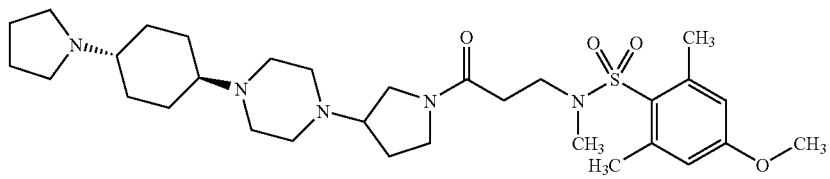 [SMILES: COc1cc(C)c(S(=O)(=O)N(C)CCC(=O)N2CCC(N3CCN([C@H]4CC[C@H](N5CCCC5)CC4)CC3)C2)c(C)c1] |

-continued
| Example | Structure |
|---|---|
| (10) | 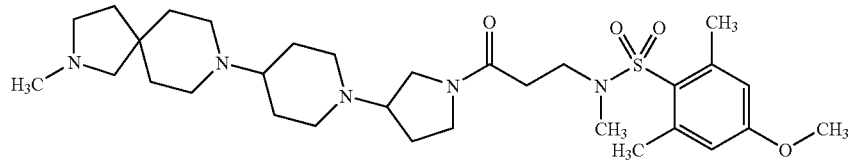 |
| (11) | 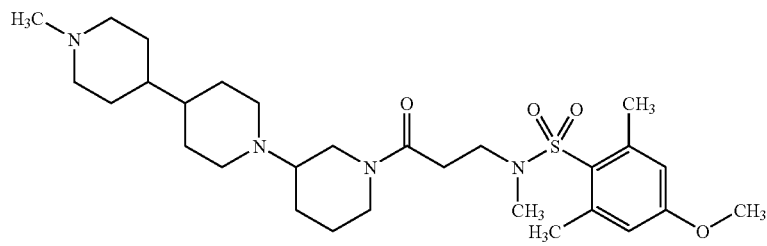 |
| (12) | 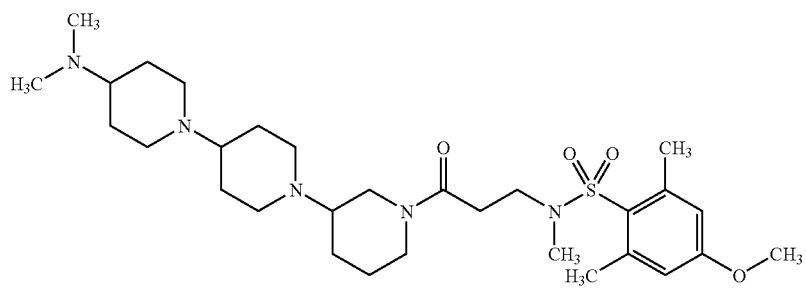 |
| (13) | 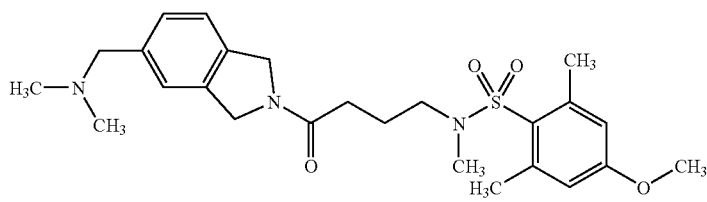 |
| (14) | 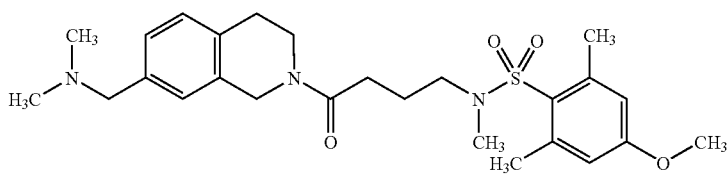 |
| (15) | 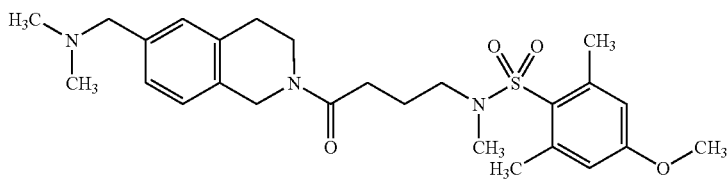 |
| (16) | 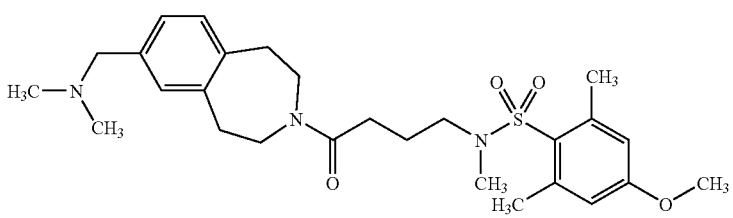 |

-continued
| Example | Structure |
|---|---|
| (17) | 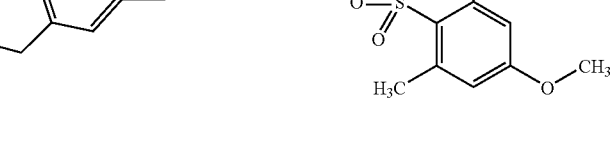 |
| (18) | 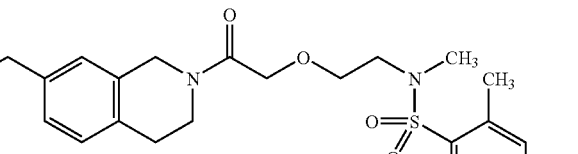 |
| (19) | 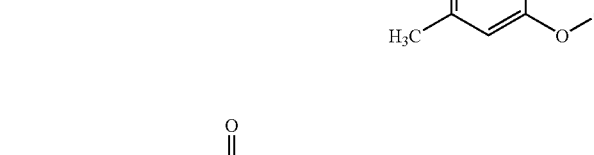 |
| (20) | 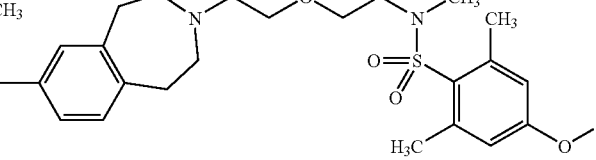 |
| (21) | Chiral 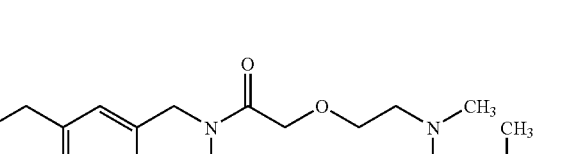 |
| (22) | Chiral  |

| Example | Structure | |
|---|---|---|
| (23) | (structure) | |
| (24) | (structure) | Chiral |
| (25) | (structure) | Chiral |
| (26) | (structure) | Chiral |
| (27) | (structure) | Chiral |
| (28) | (structure) | Chiral |

-continued
| Example | Structure |
|---|---|
| (29) | 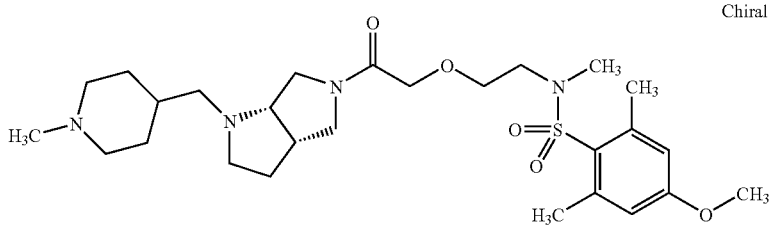 Chiral |
| (30) | 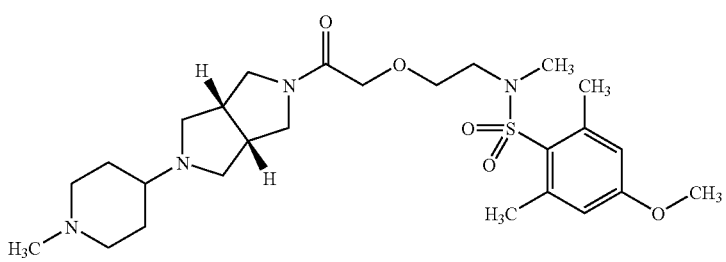 |
| (31) | 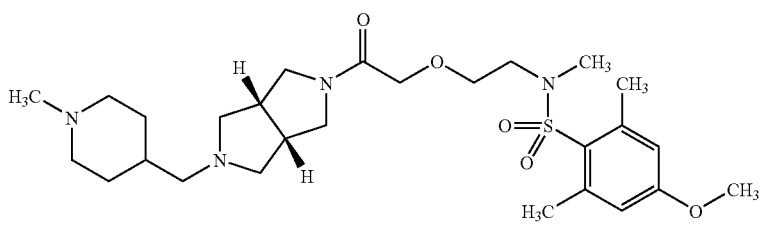 |
| (32) | 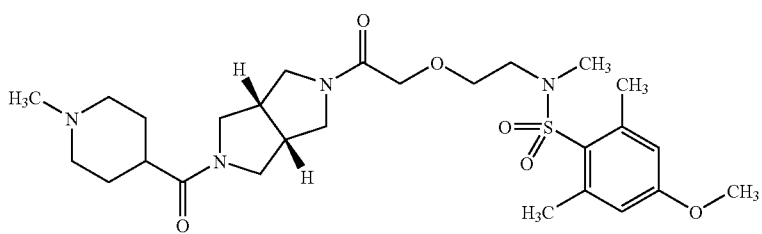 |
| (33) | 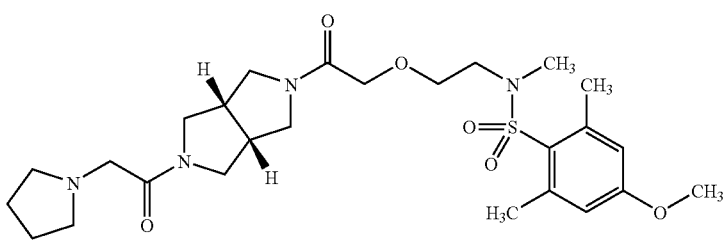 [SMILES: COc1cc(C)c(S(=O)(=O)N(C)CCOCC(=O)N2C[C@@H]3CN(C(=O)CN4CCCC4)C[C@@H]3C2)c(C)c1] |
| (34) | 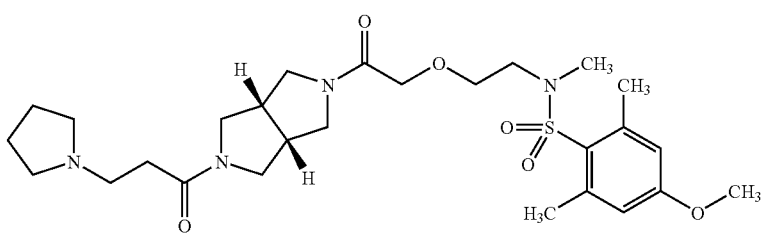 [SMILES: COc1cc(C)c(S(=O)(=O)N(C)CCOCC(=O)N2C[C@H]3CN(C(=O)CCN4CCCC4)C[C@H]3C2)c(C)c1] |

-continued

| Example | Structure |
|---|---|
| (35) | 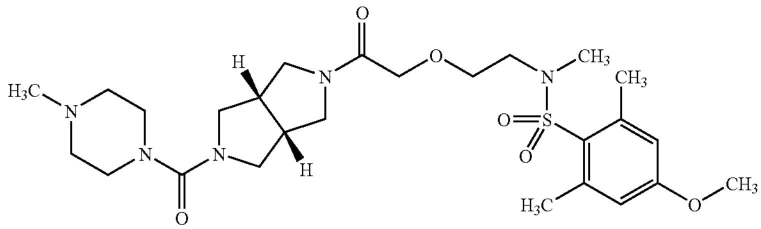 |
| (36) | 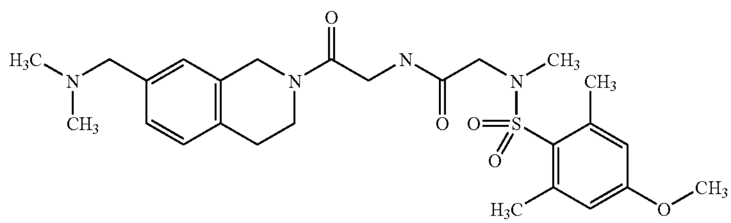 |
| (37) | 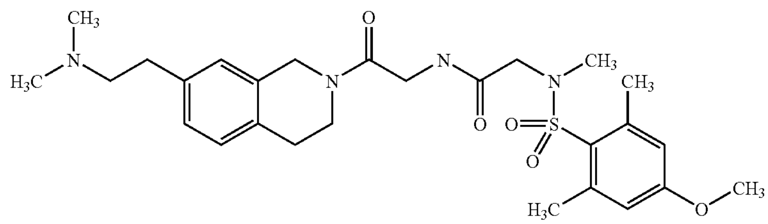 |
| (38) | 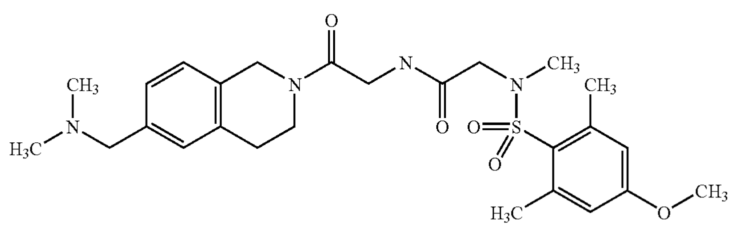 |
| (39) | | the enantiomers, the diastereomers, the mixtures thereof and the salts thereof, particularly the physiologically acceptable salts thereof with organic or inorganic acids or bases.

TERMS AND DEFINITIONS USED

Unless otherwise stated, all the substituents are independent of one another. If for example there are a plurality of $C_{1-6}$-alkyl groups as substituents in one group, in the case of three $C_{1-6}$-alkyl substituents, independently of one another, one may represent methyl, one n-propyl and one tert-butyl.

Within the scope of this application, in the definition of possible substituents, these may also be represented in the form of a structural formula. If present, an asterisk (*) in the structural formula of the substituent is to be understood as being the linking point to the rest of the molecule.

The subject-matter of this invention also includes the compounds according to the invention, including the salts thereof, wherein one or more hydrogen atoms, for example one, two, three, four or five hydrogen atoms, are replaced by deuterium.

By the term "$C_{1-3}$-alkyl" (including those which are a part of other groups) are meant alkyl groups with 1 to 3 carbon atoms and by the term "$C_{1-4}$-alkyl" are meant branched and unbranched alkyl groups with 1 to 4 carbon atoms. Examples include: methyl, ethyl, n-propyl, iso-propyl, n-butyl, iso-butyl, sec-butyl and tert-butyl. Optionally the abbreviations Me, Et, n-Pr, i-Pr, n-Bu, i-Bu, t-Bu, etc are also used for the above-mentioned groups. Unless stated otherwise, the definitions propyl and butyl include all the possible isomeric forms of the groups in question. Thus, for example, propyl includes n-propyl and iso-propyl, butyl includes iso-butyl, sec-butyl and tert-butyl.

In addition, the terms mentioned above also include those groups wherein each methylene group may be substituted by up to two fluorine atoms and each methyl group may be substituted by up to three fluorine atoms.

By the term "$C_{1-3}$-alkylene" are meant branched and unbranched alkylene groups with 1 to 3 carbon atoms, by the term "$C_{1-4}$-alkylene" are meant branched and unbranched alkylene groups with 1 to 4 carbon atoms and by the term "$C_{2-4}$-alkylene" are meant branched and unbranched alkylene groups with 2 to 4 carbon atoms. Examples include: methylene, ethylene, ethan-1,1-diyl, propylene, propane-2,2-diyl, 1-methylethylene, butylene, 1-methylpropylene, 1,1-dimethylethylene, 1,2-dimethylethylene. Unless stated otherwise, the definitions propylene and butylene include all the possible isomer forms with the same carbon number. Thus, for example, propyl also includes also 1-methylethylene and butylene includes 1-methylpropylene, 1,1-dimethylethylene, 1,2-dimethylethylene.

Moreover, the terms mentioned above also include those groups wherein each methylene group may be substituted by up to two fluorine atoms.

By the term "$C_{3-6}$-cycloalkyl" (including those which are a part of other groups) are meant cyclic alkyl groups with 3 to 6 carbon atoms. Examples include: cyclopropyl, cyclobutyl, cyclopentyl or cyclohexyl. Unless otherwise stated, the cyclic alkyl groups may be substituted by one or more groups selected from among methyl, ethyl, iso-propyl, tert-butyl, hydroxy, fluorine, chlorine, bromine and iodine.

By the term "$C_{3-6}$-cycloalkylene" (including those which are a part of other groups) are meant cyclic alkylene groups with 3 to 6 carbon atoms. Examples include: cyclopropylene, cyclobutylene, cyclopentylene or cyclohexylene. Unless otherwise stated, the cyclic alkylene groups may be substituted by one or more groups selected from among methyl, ethyl, iso-propyl, tert-butyl, hydroxy, fluorine, chlorine, bromine and iodine.

By the term "saturated aza-heterocycles" are meant four-, five-, six- or seven-membered heterocyclic rings which contain a nitrogen atom. The ring is linked to the remainder of the molecule either through the nitrogen atom or through a carbon atom and through a nitrogen atom. Examples include:

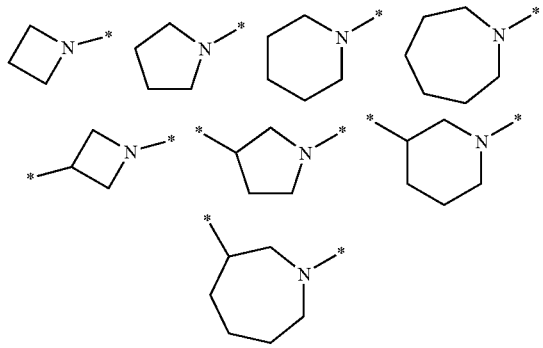

By the term "monounsaturated aza-heterocycles" are meant five-, six- or seven-membered, monounsaturated heterocyclic rings which contain a nitrogen atom and which are fused to a phenyl or pyridyl ring via the unsaturated bond. The heterocyclic ring is linked to the remainder of the molecule through a nitrogen atom or through a nitrogen atom and a carbon atom. Examples include:

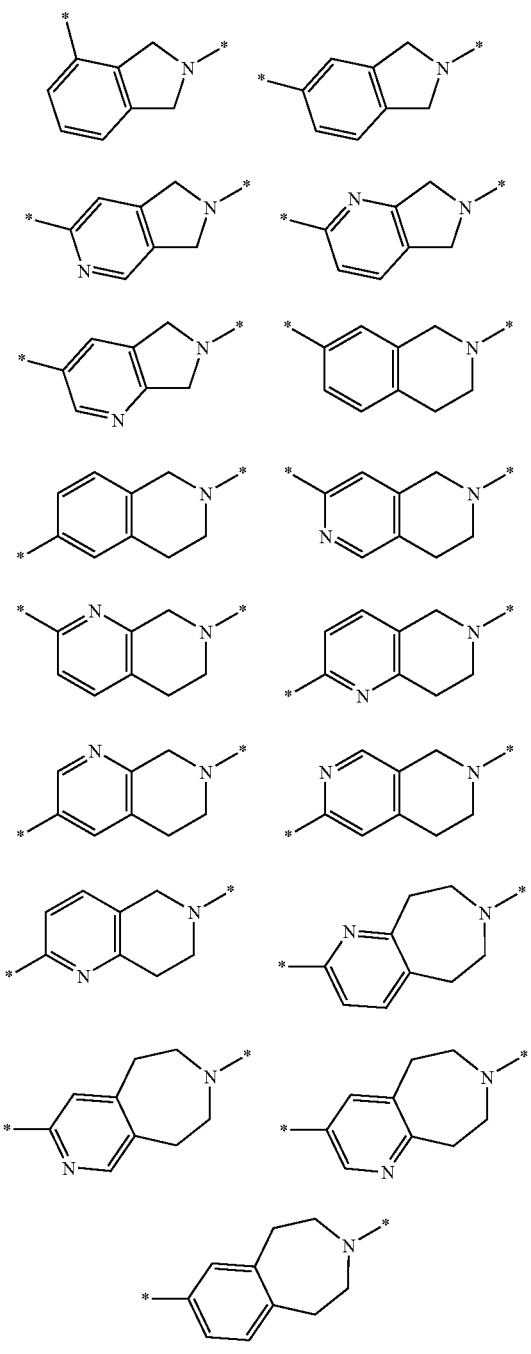

By the term "saturated diaza-heterocycles" are meant six- or seven-membered heterocyclic rings which contain two nitrogen atoms. The ring is linked to the remainder of the molecule through both nitrogen atoms. Examples include:

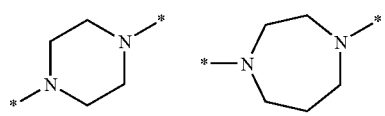 [SMILES: *N1CCN(*)CC1 ; *N1CCCN(*)CC1]

By the term "saturated diaza-heterobicyclic groups" are meant eight-, nine- or ten-membered heterobicyclic rings which contain two nitrogen atoms. The ring is linked to the remainder of the molecule through both nitrogen atoms. Examples include:

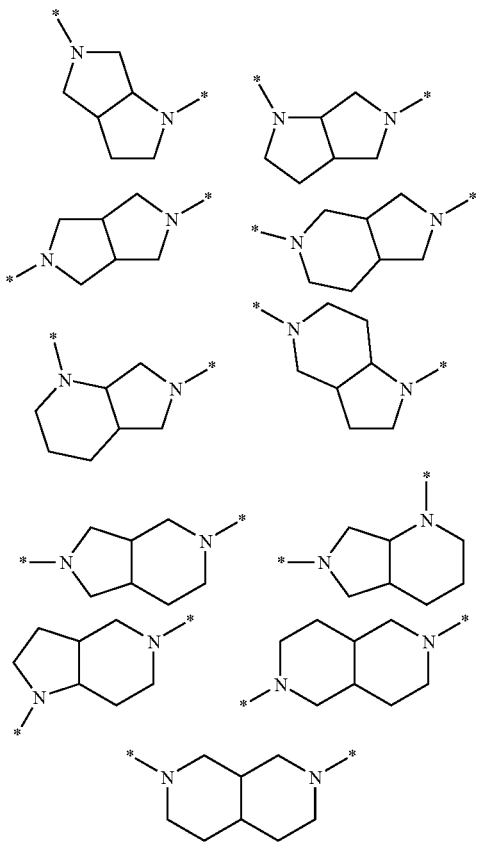

By the term "saturated diaza-spirocyclic groups" are meant nine-, ten- or eleven-membered spirocyclic rings which contain two nitrogen atoms. The ring is linked to the remainder of the molecule through both nitrogen atoms. Examples include:

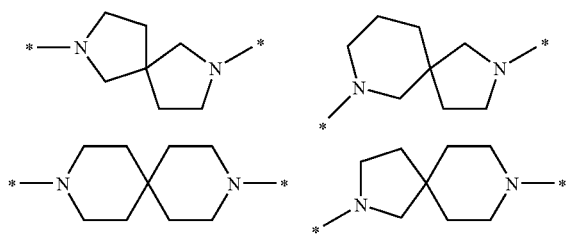

By the term "aryl" (including those which are a part of other groups) are meant aromatic ring systems with 6 or 10 carbon atoms. Examples include phenyl, 1-naphthyl or 2-naphthyl; the preferred aryl group is phenyl. Unless otherwise stated, the aromatic groups may be substituted by one or more groups selected from among methyl, ethyl, n-propyl, iso-propyl, tert-butyl, hydroxy, methoxy, trifluoromethoxy, fluorine, chlorine, bromine and iodine, while the groups may be identical or different.

By the term "heteroaryl" are meant five- or six-membered heterocyclic aromatic groups or 5-10 membered bicyclic heteroaryl rings which may contain one, two or three heteroatoms selected from among oxygen, sulphur and nitrogen, and additionally contain sufficient conjugated double bonds to form an aromatic system. Examples of five- or six-membered heterocyclic aromatic groups include:

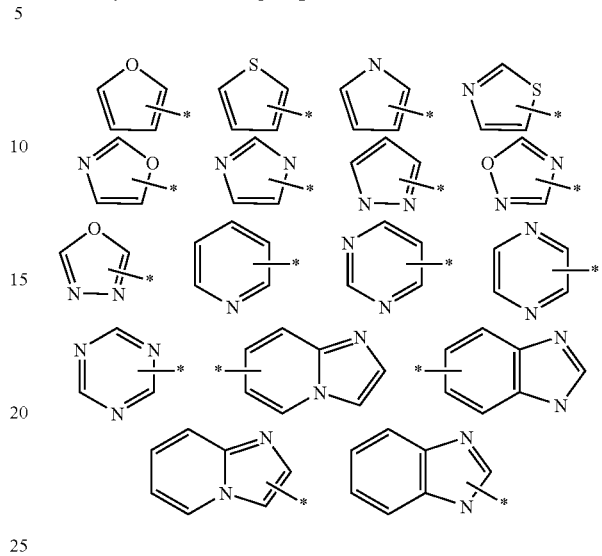

Unless otherwise stated, the heteroaryls mentioned previously may be substituted by one or more groups selected from among methyl, ethyl, n-propyl, iso-propyl, tert-butyl, hydroxy, methoxy, trifluoromethoxy, fluorine, chlorine, bromine and iodine, while the groups may be identical or different.

Bicyclic heteroaryl rings may preferably be substituted in the phenyl group.

By the term "arylene" (including those which are part of other groups) are meant aromatic ring systems with 6 or 10 carbon atoms. Examples include: phenylene, 1-naphthylene or 2-naphthylene, the preferred arylene group being phenylene. Unless otherwise stated, the aromatic groups may be substituted by one or more groups selected from among methyl, ethyl, n-propyl, iso-propyl, tert-butyl, hydroxy, methoxy, trifluoromethoxy, fluorine, chlorine, bromine and iodine.

These aromatic ring systems are linked to the rest of the molecule at two places independently of one another through a carbon atom in each case.

By the term "heteroarylene" are meant five- or six-membered heterocyclic aromatic groups or 5-10-membered bicyclic heteroaryl rings which may contain one, two or three heteroatoms selected from among oxygen, sulphur and nitrogen, and additionally sufficient conjugated double bonds to form an aromatic system. These heterocyclic aromatic groups are linked at two points independently of one another either through carbon and/or nitrogen.

The following are examples of five- or six-membered heterocyclic aromatic groups:

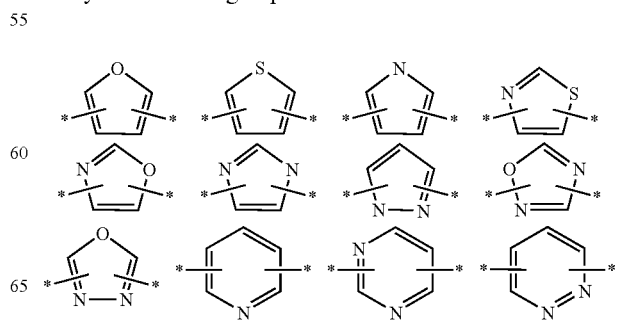

-continued

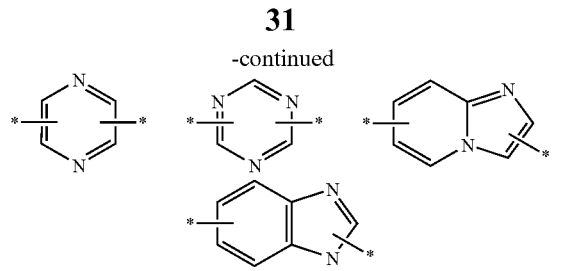

Unless otherwise stated, the heteroaromatic groups may be substituted by one or more groups selected from among methyl, ethyl, n-propyl, iso-propyl, tert-butyl, hydroxy, methoxy, trifluoromethoxy, fluorine, chlorine, bromine and iodine. Preferably, the substituents in the above-mentioned 5-10 membered bicyclic heteroaryl rings are in the phenyl ring.

If they contain suitable basic functions, for example amino groups, compounds of general formula I may be converted, particularly for pharmaceutical use, into the physiologically acceptable salts thereof with inorganic or organic acids. Examples of inorganic acids for this purpose include hydrobromic acid, phosphoric acid, nitric acid, hydrochloric acid, sulphuric acid, methanesulphonic acid, ethanesulphonic acid, benzenesulphonic acid or p-toluenesulphonic acid, while organic acids that may be used include malic acid, succinic acid, acetic acid, fumaric acid, maleic acid, mandelic acid, lactic acid, tartaric acid or citric acid.

In addition, the compounds of general formula I, if they contain suitable carboxylic acid functions, may if desired be converted into the addition salts thereof with inorganic or organic bases. Examples of inorganic bases include alkali or alkaline earth metal hydroxides, e.g. sodium hydroxide or potassium hydroxide, or carbonates, ammonia, zinc or ammonium hydroxides; examples of organic amines include diethylamine, triethylamine, ethanolamine, diethanolamine, triethanolamine, cyclohexylamine or dicyclohexylamine.

The compounds according to the invention may be present as racemates, provided that they have only one chiral element, but may also be obtained as pure enantiomers, i.e. in the (R) or (S) form.

However, the application also includes the individual diastereomeric pairs of antipodes or mixtures thereof, which are obtained if there is more than one chiral element in the compounds of general formula I, as well as the individual optically active enantiomers of which the above-mentioned racemates are made up.

Methods of Preparation

According to the invention the compounds of general formula I are obtained by methods known per se, for example by the following methods:

Scheme 1

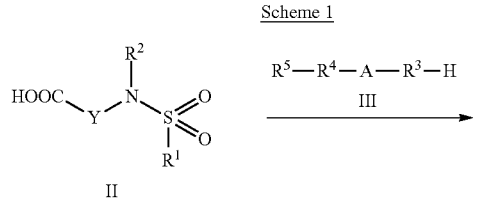

-continued

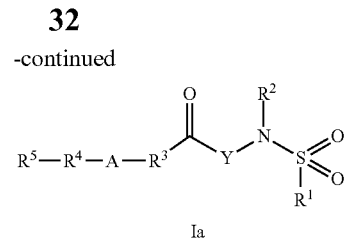

The linking of carboxylic acids of general formula II shown in Scheme 1 wherein all the groups are as hereinbefore defined, with amines of general formula III, wherein all the groups are as hereinbefore defined, forming carboxylic acid amides of general formula Ia, wherein all the groups are as hereinbefore defined, may be carried out using conventional methods of amide formation.

The coupling is preferably carried out using methods known from peptide chemistry (cf. e.g. Houben-Weyl, Methoden der Organischen Chemie, Vol. 15/2), for example using carbodiimides such as e.g. dicyclohexylcarbodiimide (DCC), diisopropyl carbodiimide (DIC) or ethyl-(3-dimethylaminopropyl)-carbodiimide, O-(1H-benzotriazol-1-yl)-N,N—N', N'-tetramethyluronium hexafluorophosphate (HBTU) or tetrafluoroborate (TBTU) or 1H-benzotriazol-1-yl-oxy-tris-(dimethylamino)-phosphonium hexafluorophosphate (BOP). By adding 1-hydroxybenzotriazole (HOBt) or 3-hydroxy-4-oxo-3,4-dihydro-1,2,3-benzotriazine (HOObt) the reaction speed can be increased. The couplings are normally carried out with equimolar amounts of the coupling components as well as the coupling reagent in solvents such as dichloromethane, tetrahydrofuran, acetonitrile, dimethyl formamide (DMF), dimethyl acetamide (DMA), N-methylpyrrolidone (NMP) or mixtures thereof and at temperatures between −30° C. and +30° C., preferably −20° C. and +25° C. If necessary, N-ethyl-diisopropylamine (Hünig base) is preferably used as an additional auxiliary base.

The carboxylic acids of general formula II used as starting materials, wherein all the groups are as hereinbefore defined, are obtained using methods known per se from the literature, for example by the methods of synthesis shown in Schemes 2 to 7.

Scheme 2

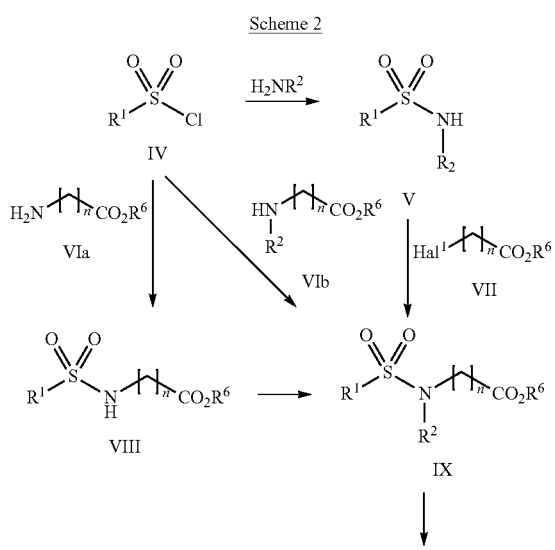

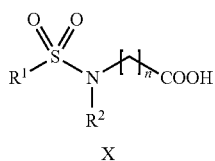

X

The sulphonic acid chlorides of general formula IV, wherein $R^1$ is as hereinbefore defined, are either known from the literature or commercially obtainable. They are reacted under standard reaction conditions with an amine of general formulae $H_2N$—$R^2$, VIa or VIb to obtain sulphonic acid amides of general formulae V, VIII or IX, wherein $R^1$ and $R^2$ are hereinbefore defined and n denotes a number 1, 2, 3 or 4 and $R^6$ denotes a $C_{1-6}$-alkyl group. The reaction is optionally carried out in the presence of a base such as triethylamine, DIPEA or pyridine and an inert solvent such as dichloromethane or tetrahydrofuran at a temperature of 0° C. to 100° C. with a typical reaction time of one to 24 hours.

The reaction of the sulphonic acid amides of general formula V with a halide of general formula VII, wherein $Hal^1$ denotes chlorine or bromine, is carried out using methods known from the literature, for example with the aid of a base such as potassium or sodium carbonate in dimethylformamide or tetrahydrofuran at 0° C. to 100° C.

The hydrolysis of the carboxylic acid esters of general formula IX, wherein $R^1$ and $R^2$ are as hereinbefore defined, n denotes a number 1, 2, 3 or 4 and $R^6$ denotes a $C_{1-3}$-alkyl group, to obtain carboxylic acids of general formula X, wherein $R^1$ and $R^2$ are as hereinbefore defined and n denotes a number 1, 2, 3 or 4 and $R^6$ denotes a $C_{1-3}$-alkyl group, is carried out under known conditions, for example with lithium or sodium carbonate and water in methanol and/or tetrahydrofuran.

strong inorganic base such as sodium hydroxide solution or potassium hydroxide solution and in an inert solvent such as toluene at 0° C. to 100° C.

The cleaving of the tert-butylester of general formula XIV, wherein $R^1$ and $R^2$ are as hereinbefore defined, n denotes a number 1, 2, 3 or 4 and $R^6$ denotes a $C_{1-3}$-alkyl group and $R^7$ denotes a hydrogen atom or a $C_{1-3}$-alkyl group, is carried out using methods known from the literature (see e.g. Philip J. Kocieński, Protecting Groups, 3rd Edition, 2005, published by Georg Thieme).

Scheme 4:

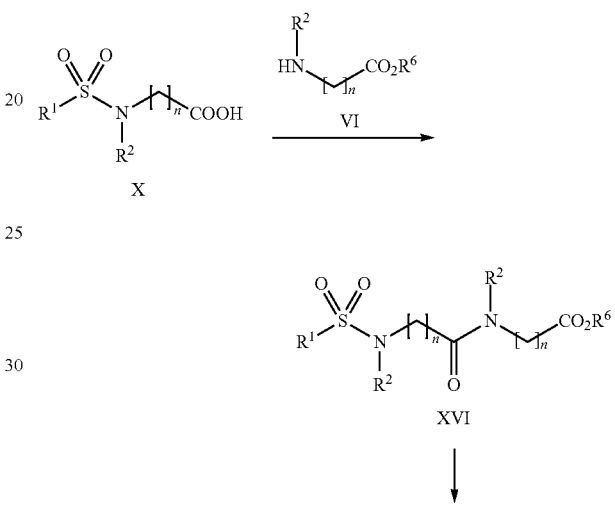

Scheme 3

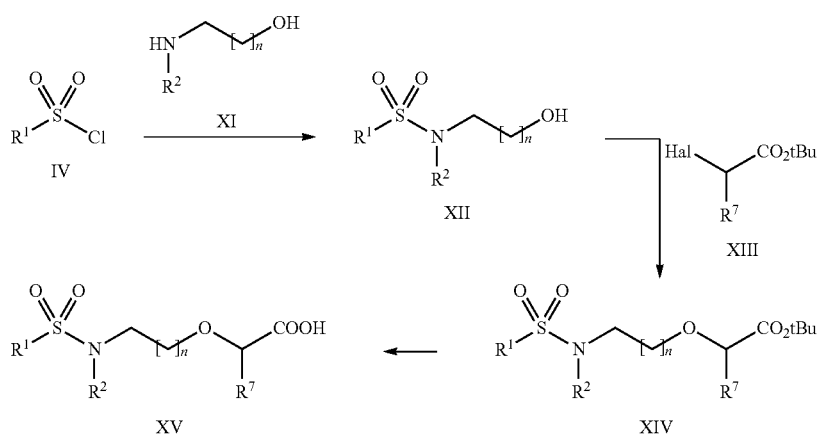

The preparation of sulphonic acid amides of general formula XIi is carried out as described under Scheme 2.

The alkylation of the hydroxyl function of the sulphonic acid amides of general formula XII, wherein $R^1$ and $R^2$ are as hereinbefore defined with the proviso that $R^2$ does not denote a hydrogen atom, and n denotes a number 1, 2, 3 or 4 and $R^6$ denotes a $C_{1-3}$-alkyl group, is carried out under reaction conditions known from the literature, for example under 2-phase conditions using a phase transfer catalyst in the presence of a -continued

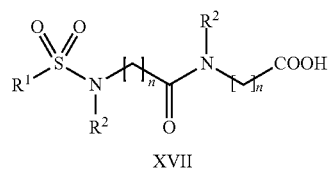

XVII

The amide linking of carboxylic acids of general formula X, wherein $R^1$ and $R^2$ are defined as hereinbefore and n denotes a number 1, 2, 3 or 4, and amino acids of general formula VI, wherein $R^1$ and $R^2$ are defined as hereinbefore, n denotes a number 1, 2, 3 or 4 and $R^6$ denotes a $C_{1-6}$-alkyl group, to form carboxylic acid amides of general formula XVI, wherein $R^1$ and $R^2$ are defined as hereinbefore, n denotes a number 1, 2, 3 or 4 and $R^6$ denotes a $C_{1-6}$-alkyl group, is carried out as described under Scheme 1.

As explained under Scheme 2, the carboxylic acid ester of general formula XVI is cleaved to form the carboxylic acid of general formula XVII, wherein $R^1$ and $R^2$ are defined as hereinbefore and n denotes a number 1, 2, 3 or 4.

The amines of general formula III used as starting materials are either commercially available or may be obtained using methods known from the literature.

Description of the Method of hBK1 Receptor Binding

CHO cells expressing the hBK1 receptor are cultivated in Dulbecco's modified medium. The medium from confluent cultures is removed and the cells are washed with PBS buffer, scraped off and isolated by centrifugation. The cells are then homogenized in suspension and the homogenate is centrifuged and resuspended. The protein content is determined and the membrane preparation obtained in this manner is then frozen at −80° C.

After thawing, 200 µl of the homogenate (50 to 100 µg of proteins/assay) are incubated at room temperature with 0.5 to 1.0 nM of kallidin (DesArg10, Leu9), [3,4-prolyl-3,43H(N)] and increasing concentrations of the test substance in a total volume of 250 µl for 60 minutes. The incubation is terminated by rapid filtration through GF/B glass fibre filters which had been pretreated with polyethyleneimine (0.3%). The protein-bound radioactivity is measured in a TopCount NXT. Non-specific binding is defined as radioactivity bound in the presence of 1.0 µM of kallidin (DesArg10, Leu9), [3,4-prolyl-3, 43H(N)]. The concentration/binding curve is analysed using a computer-assisted nonlinear curve fitting. The $K_i$ which corresponds to the test substance is determined using the data obtained in this manner.

Indications

By virtue of their pharmacological properties, the novel compounds and their physiologically acceptable salts are suitable for treating diseases and symptoms of diseases caused at least to some extent by stimulation of bradykinin-B1 receptors.

In view of their pharmacological effect the substances are suitable for the treatment of
  (a) acute pain such as e.g. toothache, peri- and postoperative pain, traumatic pain, muscle pain, the pain caused by burns, sunburn, trigeminal neuralgia, pain caused by colic, as well as spasms of the gastro-intestinal tract or uterus;
  (b) visceral pain such as e.g. chronic pelvic pain, gynaecological pain, pain before and during menstruation, pain caused by pancreatitis, peptic ulcers, interstitial cystitis, renal colic, angina pectoris, pain caused by irritable bowel, non-ulcerative dyspepsia and gastritis, non-cardiac thoracic pain and pain caused by myocardial ischaemia and cardiac infarct;
  (c) neuropathic pain such as e.g. painful neuropathies, pain of diabetic neuropathy, AIDS-associated neuropathic pain, pain of lumbago, non-herpes-associated neuralgia, post-zoster neuralgia, nerve damage, cerebro-cranial trauma, pain of nerve damage caused by toxins or chemotherapy, phantom pain, pain of multiple sclerosis, nerve root tears and painful traumatically-caused damage to individual nerves;
  (d) inflammatory/pain receptor-mediated pain in connection with diseases such as osteoarthritis, rheumatoid arthritis, rheumatic fever, tendo-synovitis, tendonitis, gout, vulvodynia, damage to and diseases of the muscles and fascia (muscle injury, fibromyalgia), osteoarthritis, juvenile arthritis, spondylitis, gout-arthritis, psoriasis-arthritis, fibromyalgia, myositis, migraine, dental disease, influenza and other virus infections such as colds, systemic lupus erythematodes,
  (e) tumour pain associated with cancers such as lymphatid or myeloid leukaemia, Hodgkin's disease, non-Hodgkin's lymphomas, lymphogranulomatosis, lymphosarcomas, solid malignant tumours and extensive metastases;
  (f) headache diseases such as e.g. headache of various origins, cluster headaches, migraine (with or without aura) and tension headaches.

The compounds are also suitable for treating
  (g) inflammatory changes connected with diseases of the airways such as bronchial asthma, including allergic asthma (atopic and non-atopic) as well as bronchospasm on exertion, occupationally induced asthma, viral or bacterial exacerbation of an existing asthma and other non-allergically induced asthmatic diseases;
  chronic obstructive pulmonary disease (COPD) including pulmonary emphysema, acute adult respiratory distress syndrome (ARDS), bronchitis, lung inflammation, allergic rhinitis (seasonal and all year round), vasomotor rhinitis and diseases caused by dust in the lungs such as aluminosis, anthracosis, asbestosis, chalicosis, siderosis, silicosis, tabacosis and byssinosis;
  (h) inflammatory phenomena caused by sunburn and burns, oedema after burns trauma, cerebral oedema and angiooedema, intestinal complaints including Crohn's diseases and ulcerative colitis, irritable bowel syndrome, pancreatitis, nephritis, cystitis (interstitial cystitis), uveitis; inflammatory skin diseases (such as e.g. psoriasis and eczema), vascular diseases of the connective tissue, lupus, sprains and fractures;
  (i) diabetes mellitus and its effects (such as e.g. diabetic vasculopathy, diabetic neuropathy, diabetic retinopathy) and diabetic symptoms in insulitis (e.g. hyperglycaemia, diuresis, proteinuria and increased renal excretion of nitrite and kallikrein);
  (j) neurodegenerative diseases such as Parkinson's disease and Alzheimer's disease;
  (k) sepsis and septic shock after bacterial infections or after trauma;
  (l) syndromes that cause itching and allergic skin reactions;
  (m) osteoporosis;
  (n) epilepsy;
  (o) damage to the central nervous system;
  (p) wounds and tissue damage;
  (q) inflammation of the gums;
  (r) benign prostatic hyperplasia and hyperactive bladder;
  (s) pruritus;
  (t) vitiligo;
  (u) disorders of the motility of respiratory, genito-urinary, gastro-intestinal or vascular regions and
  (v) post-operative fever.

In addition to being suitable as human therapeutic agents, these substances are also useful in the veterinary treatment of domestic animals, exotic animals and farm animals.

For treating pain, it may be advantageous to combine the compounds according to the invention with stimulating substances such as caffeine or other pain-alleviating active compounds. If active compounds suitable for treating the cause of the pain are available, these can be combined with the compounds according to the invention. If, independently of the pain treatment, other medical treatments are also indicated, for example for high blood pressure or diabetes, the active compounds required can be combined with the compounds according to the invention.

The following compounds may be used for combination therapy, for example:

Non-steroidal antirheumatics (NSAR): COX-2 inhibitors such as propionic acid derivatives (alminoprofen, benoxaprofen, bucloxic acid, carprofen, fenhufen, fenoprofen, fiuprofen, fiulbiprofen, ibuprofen, indoprofen, ketoprofen, miroprofen, naproxen, oxaprozin, pirprofen, pranoprofen, suprofen, tiaprofenic acid, tioxaprofen), acetic acid derivatives (indomethacin, acemetacin, alcofenac, isoxepac, oxpinax, sulindac, tiopinac, tolmetin, zidometacin, zomepirac) fenamic derivatives (meclofenamic acid, mefenamic acid, tolfenamic acid), biphenyl-carboxylic acid derivatives, oxicams (isoxicam, meloxicam, piroxicam, sudoxicam and tenoxicam), salicylic acid derivatives (acetylsalicylic acid, sulphasalazin, mesalazin, olsalazin, and pyrazolone, apazone, bezpiperylone, feprazone, mofebutazone, oxyphenbutazone, phenylbutazone, propyphenazone and metamizol), and coxibs (celecoxib, valecoxib, rofecoxib, etoricoxib).

Opiate receptor agonists such as e.g. morphine, propoxyphen (Darvon), tramadol, buprenorphine.

Cannabinoid agonists such as e.g. GW-1000, KDS-2000, SAB-378, SP-104, NVP001-GW-843166, GW-842166X, PRS-211375.

Sodium channel blockers such as e.g. carbamazepine, mexiletin, lamotrigin, pregabalin, tectin, NW-1029, CGX-1002.

N-type calcium channel blockers such as e.g. ziconitide, NMED-160, SP1-860.

Serotonergic and noradrenergic modulators such as e.g. SR-57746, paroxetine, duloxetine, clonidine, amitriptyline, citalopram.

Corticosteroids such as e.g. betamethasone, budesonide, cortisone, dexamethasone, hydrocortisone, methylprednisolone, prednisolone, prednisone and triamcinolone.

Histamine H1-receptor antagonists such as e.g. Bromopheniramine, chlorpheniramine, dexchlorpheniramine, triprolidine, clemastine, diphenhydramine, diphenylpyraline, tripelennamine, hydroxyzine, methdilazine, promethazine, trimeprazine azatadine, cyproheptadine, antazoline, pheniramine, pyrilamine, astemizole, terfenadine, loratadine, cetirizine, desloratadine, fexofenadine, levocetirizine.

Histamine H2-receptor antagonists such as e.g. cimetidine, famotidine, and ranitidine.

Proton pump inhibitors such as e.g. omeprazole, pantoprazole, esomeprazole.

Leukotriene antagonists and 5-lipoxygenasehemmer such as e.g. zafirlukast, montelukast, pranlukast and zileuton.

Local anaesthetics such as e.g. Ambroxol, lidocaine.

VR1 agonists and antagonists such as e.g. NGX-4010, WL-1002, ALGRX-4975, WL-10001, AMG-517.

Nicotine receptor agonists such as e.g. ABT-202, A-366833, ABT-594, BTG-102, A-85380, CGX1204.

P2X3-receptor antagonists such as e.g. A-317491, ISIS-13920, AZD-9056.

NGF agonists and antagonists such as e.g. RI-724, RI-1024, AMG-819, AMG-403, PPH 207.

NK1 and NK2 antagonists such as e.g. DA-5018, R-116301, CP-728663, ZD-2249.

NMDA antagonists such as e.g. NER-MD-11, CNS-5161, EAA-090, AZ-756, CNP-3381.

potassium channel modulators such as e.g. CL-888, ICA-69673, retigabin.

GABA modulators such as e.g. lacosamide.

Serotonergic and noradrenergic modulators such as e.g. SR-57746, paroxetine, duloxetine, clonidine, amitriptyline, citalopram, flibanserine.

Anti-migraine drugs such as e.g. sumatriptan, zolmitriptan, naratriptan, eletriptan.

The dosage necessary for obtaining a pain-alleviating effect is, in the case of intravenous administration, expediently from 0.01 to 3 mg/kg of body weight, preferably from 0.1 to 1 mg/kg, and, in the case of oral administration, from 0.1 to 8 mg/kg of body weight, preferably from 0.5 to 3 mg/kg, in each case 1 to 3 times per day. The compounds prepared according to the invention can be administered intravenously, subcutaneously, intramuscularly, intrarectally, intranasally, by inhalation, transdermally or orally, aerosol formulations being particularly suitable for inhalation. They can be incorporated into customary pharmaceutical preparations, such as tablets, coated tablets, capsules, powders, suspensions, solutions, metered-dose aerosols or suppositories, if appropriate together with one or more customary inert carriers and/or diluents, for example with maize starch, lactose, cane sugar, microcrystalline cellulose, magnesium stearate, polyvinylpyrrolidone, citric acid, tartaric acid, water, water/ethanol, water/glycerol, water/sorbitol, water/polyethylene glycol, propylene glycol, cetylstearyl alcohol, carboxymethylcellulose or fatty substances, such as hardened fat, or suitable mixtures thereof.

Experimental Section

Generally, there are IR, $^1$H NMR and/or mass spectra for the compounds that were prepared. The ratios given for the eluants are in volume units of the solvents in question. For ammonia, the given volume units are based on a concentrated solution of ammonia in water.

Unless indicated otherwise, the acid, base and salt solutions used for working up the reaction solutions are aqueous systems having the stated concentrations. For chromatographic purification, silica gel from Millipore (MATREX™, 35-70 µm) or Alox (E. Merck, Darmstadt, Alumina 90 standardized, 63-200 µm, article No. 1.01097.9050) are used.

In the descriptions of the experiments, the following abbreviations are used:

TLC thin layer chromatogram
DIPEA diisopropylethylamine
DMF dimethylformamide
HPLC High Pressure Liquid chromatography
tert tertiary
TBTU 2-(1H-benzotriazol-1-yl)-1.1.3.3-tetramethyluronium-tetrafluoroborate
TFA trifluoroacetic acid
THF tetrahydrofuran The following analytical HPLC methods were used:
Method 1:

| Column: | YMC-Pack ODS-AQ, 3.0 µM, 4.6 × 75 mm |
| --- | --- |
| Detection: | 230-360 nm |
| Eluant A: | water/0.1% formic acid |
| Eluant B: | acetonitrile/0.1% formic acid |
| Gradient: | |

| time in min | % A | % B | flow rate in mL/min |
| --- | --- | --- | --- |
| 0.0 | 95.0 | 5.0 | 1.6 |
| 4.5 | 10.0 | 90.0 | 1.6 |
| 5.0 | 10.0 | 90.0 | 1.6 |
| 5.5 | 90.0 | 10.0 | 1.6 |

Method 2:

| Column: | Merck chromolith ™ Flash RP18e, 4.6 × 25 mm |
|---|---|
| Detection: | 190-400 nm |
| Eluant A: | water/0.1% formic acid |
| Eluant B: | acetonitrile/0.1% formic acid |
| Gradient: | |

| time in min | % A | % B | flow rate in mL/min |
|---|---|---|---|
| 0.0 | 90.0 | 10.0 | 1.6 |
| 2.7 | 10.0 | 90.0 | 1.6 |
| 3.0 | 10.0 | 90.0 | 1.6 |
| 3.3 | 90.0 | 10.0 | 1.6 |

Method 3:

| Column: | Zorbax Stable Bond C18, 3.5 μM, 4.6 × 75 mm |
|---|---|
| Detection: | 230-360 nm |
| Eluant A: | water/0.1% formic acid |
| Eluant B: | acetonitrile/0.1% formic acid |
| Gradient: | |

| time in min | % A | % B | flow rate in mL/min |
|---|---|---|---|
| 0.0 | 95.0 | 5.0 | 1.6 |
| 0.1 | 95.0 | 5.0 | 1.6 |
| 4.5 | 10.0 | 90.0 | 1.6 |
| 5.09 | 10.0 | 90.0 | 1.6 |
| 5.5 | 90.0 | 10.0 | 1.6 |

Method 4:

| Column: | Interchim Strategy C18, 5 μM, 4.6 × 50 mm |
|---|---|
| Detection: | 220-320 nm |
| Eluant A: | water/0.1% TFA |
| Eluant B: | acetonitrile |
| Gradient: | |

| time in min | % A | % B | flow rate in mL/min |
|---|---|---|---|
| 0.0 | 95.0 | 5.0 | 3.0 |
| 0.3 | 95.0 | 5.0 | 3.0 |
| 2.0 | 2.0 | 98.0 | 3.0 |
| 2.4 | 2.0 | 98.0 | 3.0 |
| 2.45 | 95.0 | 5.0 | 3.0 |
| 2.8 | 95.0 | 5.0 | 3.0 |

Method 5:

| Column: | Waters XBridge C18, 3.5 μM, 4.6 × 50 mm |
|---|---|
| Detection: | 210-500 nm |
| Eluant A: | water/0.1% TFA |
| Eluant B: | acetonitrile/0.1% TFA |
| Gradient: | |

| time in min | % A | % B | flow rate in mL/min |
|---|---|---|---|
| 0.0 | 95.0 | 5.0 | 1.5 |
| 2.0 | 0.0 | 100.0 | 1.5 |
| 3.0 | 0.0 | 100.0 | 1.5 |
| 3.4 | 95.0 | 5.0 | 1.5 |

Preparation of the End Compounds

Example 1

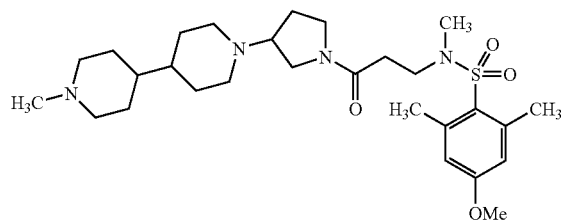

1a)

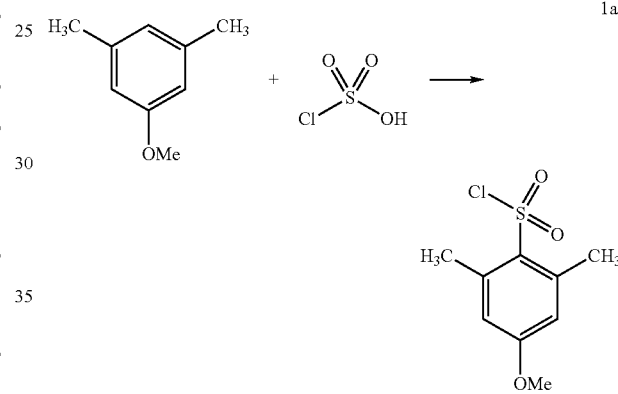

A mixture of 2.0 g (14.69 mmol) of 3,5-dimethylanisole and 20 ml dichloromethane is combined with 5.85 ml (88.0 mmol) of chlorosulphonic acid while cooling with an ice bath. The reaction mixture is then stirred for 20 min at ambient temperature and then poured onto 50 ml ice water. The mixture is extracted with 100 ml dichloromethane. The organic extracts are washed with 5% sodium hydrogen carbonate solution, dried on sodium sulphate and evaporated to dryness.

$C_9H_{11}ClO_3S$ (234.70)

[M+H]+=234/236

TLC: silica gel, petroleum ether/ethyl acetate 9:1, Rf value=0.46

1b)

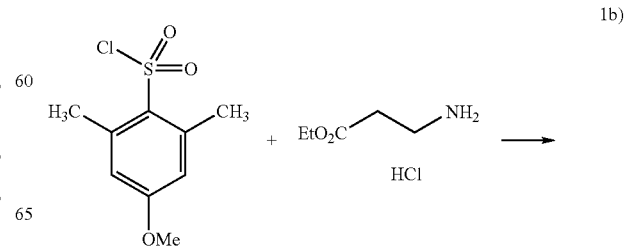

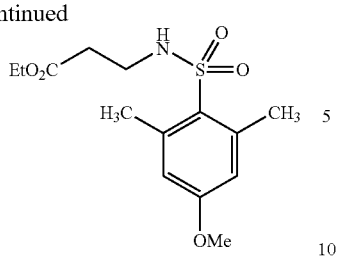

A mixture of 3.00 g (12.78 mmol) of product from 1a, 2.16 g (14.06 mmol) of β-alaninethylester hydrochloride, 7.13 ml (51.13 mmol) of triethylamine and 70 ml dichloromethane is stirred overnight at ambient temperature. The reaction mixture is then washed with 0.5 M HCl, saturated sodium hydrogen carbonate solution, water and saturated sodium chloride solution, dried on sodium sulphate and evaporated to dryness in vacuo.

$C_{14}H_{21}NO_5S$ (315.39)
[M+H]+=316
TLC: silica gel, petroleum ether/ethyl acetate 2:1, Rf value=0.23

1c)

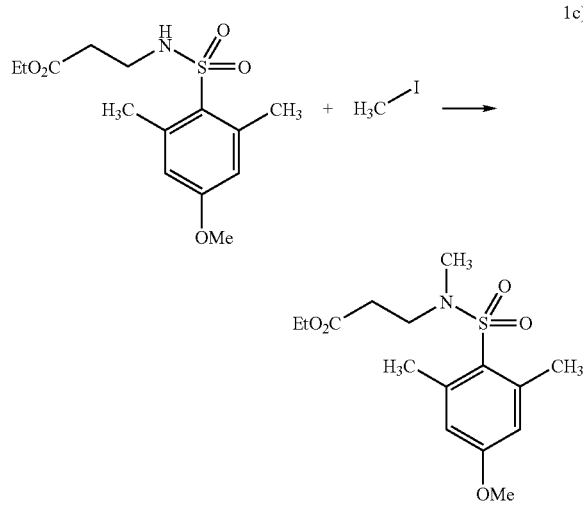

A mixture of 4.06 g (12.87 mmol) of product from 1b, 0.84 ml (13.55 mmol) of methyl iodide, 3.56 g (25.75 mmol) of anhydrous potassium carbonate and 40 ml DMF is stirred for five hours at ambient temperature. The reaction mixture is then evaporated to dryness in vacuo, the residue is taken up in ethyl acetate. It is washed with water, saturated sodium hydrogen carbonate solution and saturated sodium chloride solution, dried on sodium sulphate and evaporated to dryness in vacuo.

$C_{15}H_{23}NO_5S$ (329.41)
[M+H]+=330
TLC: silica gel, petroleum ether/ethyl acetate 2:1, Rf value=0.36

1d)

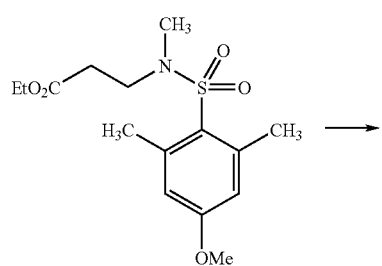

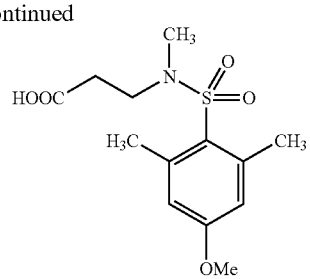

A mixture of 3.83 g (11.63 mmol) of product from 1c, 2.44 g (58.13 mmol) of lithium hydroxide monohydrate, 30 ml THF and 30 ml of water is stirred for one hour at ambient temperature. Then the THF is eliminated in vacuo and the residue is acidified with concentrated HCl. The reaction mixture is then extracted three times with ethyl acetate. The organic extracts are washed with saturated sodium chloride solution, dried on sodium sulphate and evaporated to dryness. The crude product is triturated with diethyl ether and suction filtered.

$C_{13}H_{19}NO_5S$ (301.36)
[M+H]+=302
TLC: silica gel, petroleum ether/ethyl acetate 1:1, Rf value=0.12

1e)

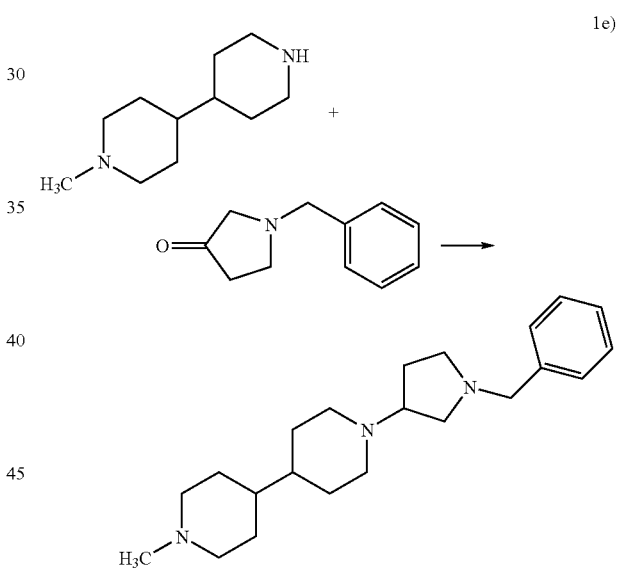

A mixture of 1.19 g (6.60 mmol) of 1-methyl-[4,4']bipiperidine (J. Chem. Soc. 1957, 3165-3172), 1.28 g (7.80 mmol) of 1-benzyl-3-pyrrolidinone (Aldrich) and 60 ml THF is stirred for one hour at ambient temperature. Then 1.65 g (7.80 mmol) of sodium triacetoxyborohydride and 0.37 ml (6.50 mmol) of glacial acetic acid are added. The reaction mixture is then stirred overnight at ambient temperature and then combined with semisaturated potassium carbonate solution. The THF is eliminated in vacuo, the aqueous residue is extracted with ethyl acetate. The organic extracts are dried on sodium sulphate and evaporated to dryness. The crude product thus obtained is purified by column chromatography (eluant: dichloromethane/methanol/ammonia 95:5:0.5 to 90:10:1).

$C_{22}H_{35}N_3$ (341.53)
[M+H]+=342
TLC: silica gel, dichloromethane/methanol/ammonia 9:1:0.1, Rf value=0.31

1f)

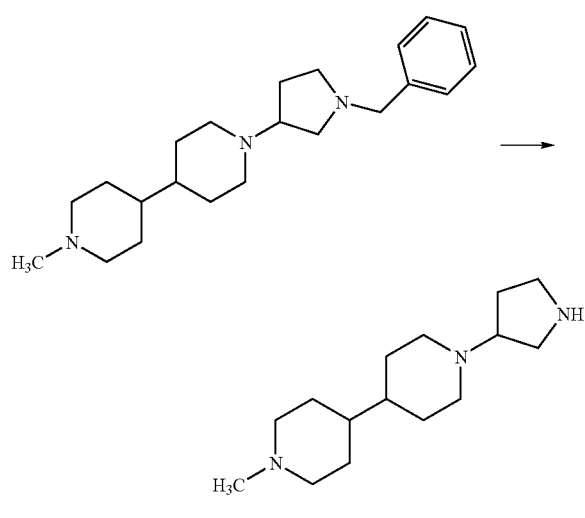

A mixture of 1.43 g (4.19 mmol) of product from 1e, 0.30 g palladium hydroxide and 40 ml of methanol is hydrogenated for four hours in the autoclave at ambient temperature. Then the catalyst is filtered off and the filtrate is evaporated to dryness in vacuo.

$C_{15}H_{29}N_3$ (251.41)
[M+H]+=252
TLC: silica gel, dichloromethane/methanol/ammonia 8:2: 0.2, Rf value=0.08

1g)

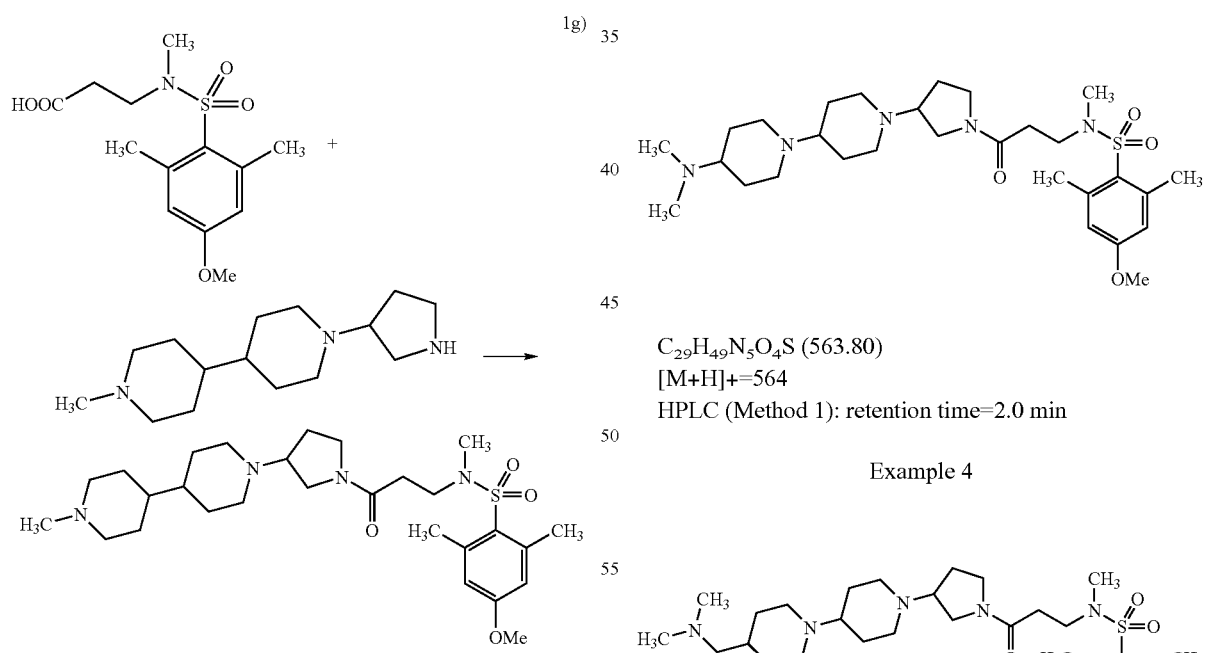

A mixture of 90.4 mg (0.30 mmol) of product from 1d, 83.6 μl (0.60 mmol) of triethylamine, 106.0 mg (0.33 mmol) of TBTU, 7 ml THF and 1 ml DMF is stirred for 30 min at ambient temperature. Then 75.4 mg (0.30 mmol) of product from 1f are added and the mixture is stirred further overnight at ambient temperature. Then the THF is eliminated in vacuo, the DMF-containing residue is combined with 2 ml of methanol/water and a few drops of formic acid. This mixture is filtered through a syringe filter and then the product is eluted using preparative HPLC. The corresponding eluates are evaporated to dryness, combined with saturated potassium carbonate solution and extracted with ethyl acetate. The organic extracts are dried on sodium sulphate and evaporated to dryness in vacuo. The product thus obtained is triturated with diisopropylether and dried in the drying pistol at 60° C.

$C_{28}H_{46}N_4O_4S$ (534.76)
[M+H]+=535
HPLC (Method 1): retention time=2.3 min The following compounds (Example 2-12) were prepared analogously to Example 1:

Example 2

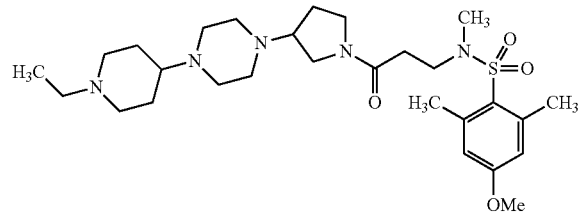 [SMILES: CCN1CCC(N2CCN(C3CCN(C(=O)CCN(C)S(=O)(=O)c4c(C)cc(OC)cc4C)C3)CC2)CC1]

$C_{28}H_{47}N_5O_4S$ (549.77)
[M+H]+=550
HPLC (Method 1): retention time=2.3 min Example 3

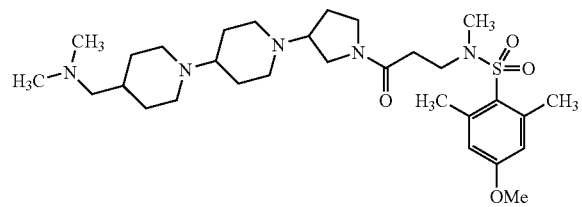

$C_{29}H_{49}N_5O_4S$ (563.80)
[M+H]+=564
HPLC (Method 1): retention time=2.0 min Example 4

$C_{30}H_{51}N_5O_4S$ (577.82)
[M+H]+=578
HPLC (Method 1): retention time=2.0 min

Example 5

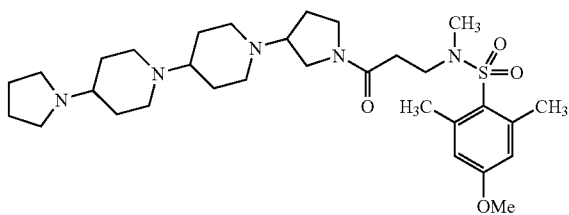

C$_{31}$H$_{51}$N$_5$O$_4$S (589.83)
[M+H]+=590
HPLC (Method 1): retention time=2.0 min

Example 6

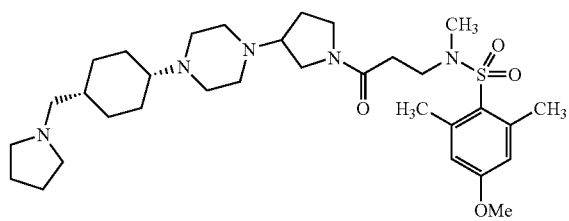 [SMILES: COc1cc(C)c(S(=O)(=O)N(C)CCC(=O)N2CCC(N3CCN([C@H]4CC[C@@H](CN5CCCC5)CC4)CC3)C2)c(C)c1]

C$_{32}$H$_{53}$N$_5$O$_4$S×3HCl (713.24)
[M+H]+=604
TLC: silica gel, dichloromethane/methanol/ammonia 8:2:0.2, Rf value=0.71

Example 7

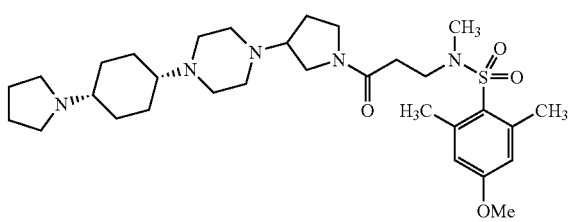 [SMILES: COc1cc(C)c(S(=O)(=O)N(C)CCC(=O)N2CCC(N3CCN([C@H]4CC[C@@H](N5CCCC5)CC4)CC3)C2)c(C)c1]

C$_{31}$H$_{51}$N$_5$O$_4$S×3HCl (699.22)
[M+H]+=590
HPLC (Method 1): retention time=2.3 min

Example 8

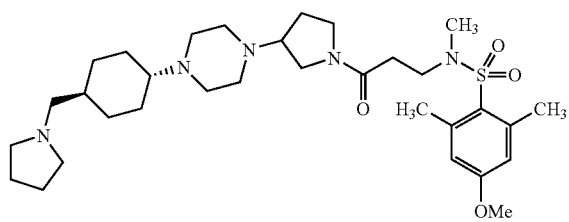 [SMILES: COc1cc(C)c(S(=O)(=O)N(C)CCC(=O)N2CCC(N3CCN([C@H]4CC[C@H](CN5CCCC5)CC4)CC3)C2)c(C)c1]

C$_{32}$H$_{53}$N$_5$O$_4$S (603.86)
[M+H]+=604
TLC: silica gel, dichloromethane/methanol/ammonia 8:2:0.2, Rf value=0.64

Example 9

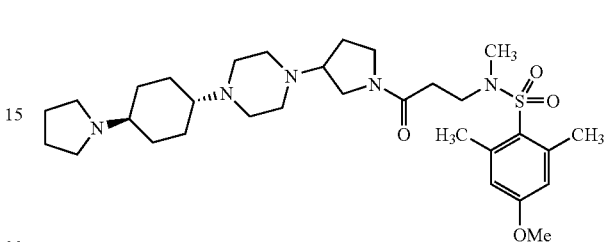

C$_{31}$H$_{51}$N$_5$O$_4$S (589.83)
[M+H]+=590
TLC: silica gel, dichloromethane/methanol/ammonia 8:2:0.2, Rf value=0.49

Example 10

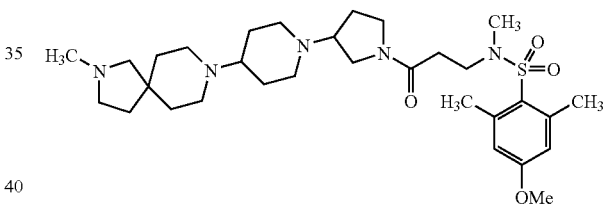

C$_{31}$H$_{51}$N$_5$O$_4$S×3HCl (699.22)
[M+H]+=590
HPLC (Method 1): retention time=2.06 min

Example 11

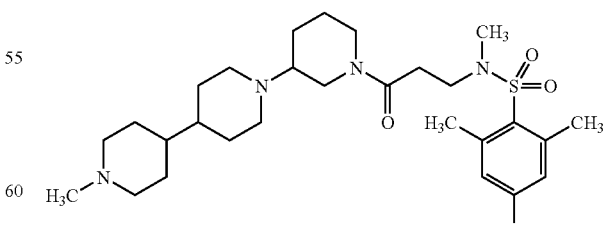

C$_{29}$H$_{48}$N$_4$O$_4$S×2HCl (621.70)
[M+H]+=549
HPLC (Method 1): retention time=2.4 min

Example 12

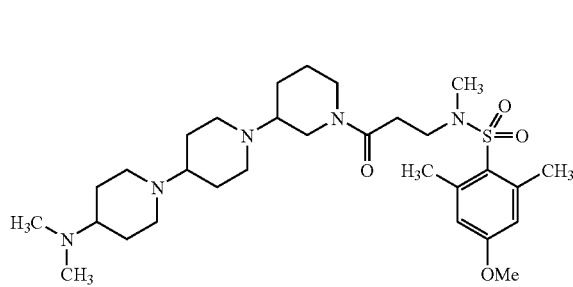

C$_{30}$H$_{51}$N$_5$O$_4$S×3HCl (687.21)
[M+H]+=578
HPLC (Method 1): retention time=2.1 min

Example 13

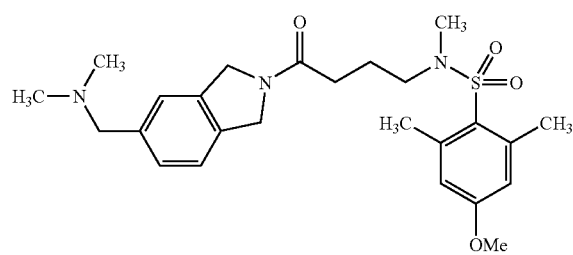

13a)

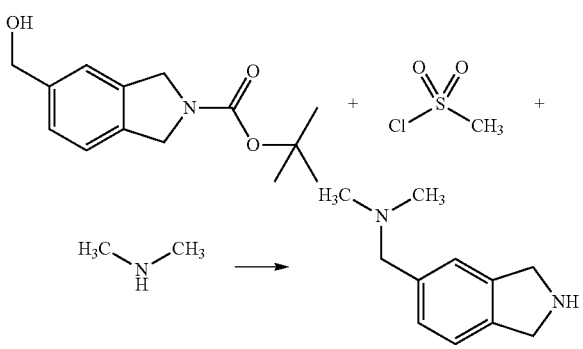

A mixture of 0.20 g (0.80 mmol) of tert-butyl 5-hydroxymethyl-1,3-dihydroisoindole-2-carboxylate (analogously to THL 23, 1982, 2691-2692), 124 µl (0.88 mmol) of triethylamine and 2 ml dichloromethane is combined with 65.2 µl (0.84 mmol) of methanesulphonic acid chloride while cooling with an ice bath. The reaction mixture is then stirred for 1 hour at 0° C., then mixed with 1.20 ml (2.41 mmol) of dimethylamine 2M in THF while cooling with an ice bath and heated overnight to ambient temperature. The reaction mixture is then evaporated to dryness in vacuo, dissolved in some methanol and membrane-filtered. The crude product is purified by preparative HPLC.

C$_{11}$H$_{16}$N$_2$×2C$_2$HF$_3$O$_2$ (404.30)
[M+H]+=177
HPLC (Method 2): retention time=1.40 min 13b)

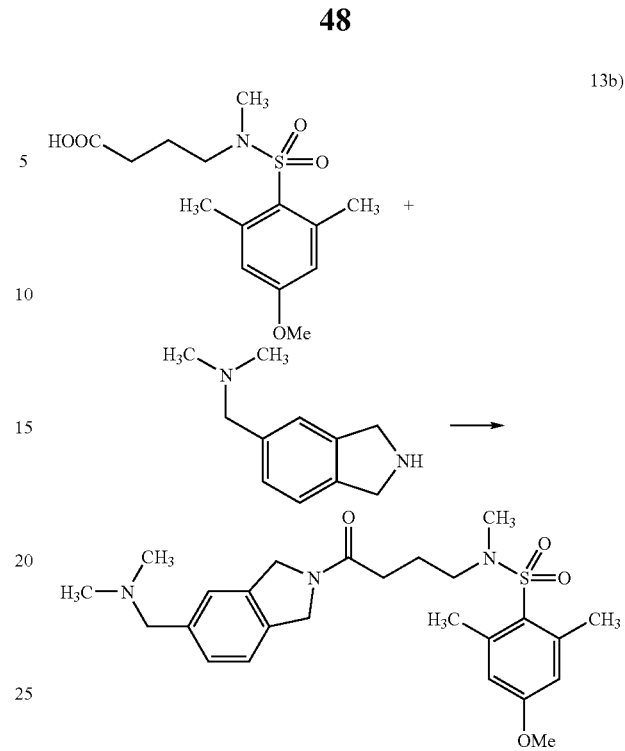

Example 13 is prepared analogously to 1 g from 50.0 mg (0.16 mmol) of 4-[(4-methoxy-2,6-dimethylbenzenesulphonyl)-methylamino]-butyric acid (prepared analogously to 1a-1d), 128.2 mg (0.32 mmol) of product from 13a, 0.11 ml (0.79 mmol) of triethylamine and 56.0 mg (0.17 mmol) of TBTU in 0.5 ml DMF.

C$_{25}$H$_{35}$N$_3$O$_4$S (473.63)
[M+H]+=474
HPLC (Method 2): retention time=1.57 min

Example 14

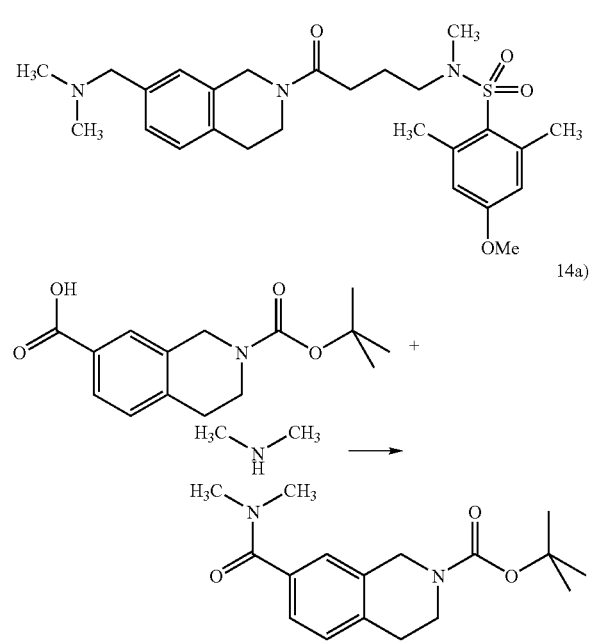

14a)

14a is prepared analogously to 1 g from 1.00 g (3.61 mmol) of 2-tert-butyl 3,4-dihydro-1H-isoquinoline-2,7-dicarboxylate (Arch), 1.98 ml (3.97 mmol) of dimethylamine 2 M in THF, 0.60 ml (4.33 mmol) of triethylamine and 1.39 g (4.33 mmol) of TBTU in 10 ml DMF.

$C_{17}H_{24}N_2O_3$ (304.38)

[M+H]+=305

HPLC (Method 2): retention time=2.06 min

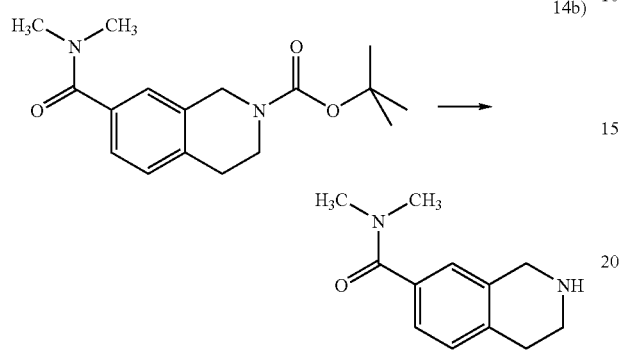

14b)

A mixture of 1.00 g (3.29 mmol) of product from 14a, 5 ml TFA and 10 ml dichloromethane is stirred for 1.5 hours at ambient temperature. Then the reaction mixture is evaporated to dryness in vacuo. The residue is mixed with water, made alkaline with 1 M sodium hydroxide solution and extracted with dichloromethane. The combined organic extracts are washed with water, dried on sodium sulphate and evaporated to dryness in vacuo.

$C_{12}H_{16}N_2O$ (204.27)

[M+H]+=205

HPLC (Method 2): retention time=0.33 min

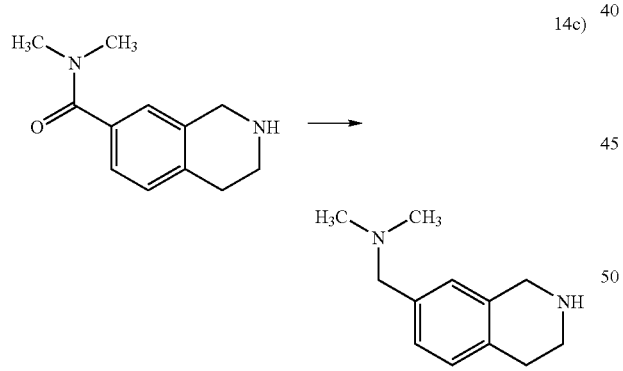

14c)

A mixture of 0.50 g (2.45 mmol) of product from 14b and 20 ml dioxane is slowly added dropwise to 7.34 ml (7.34 mmol) of lithium aluminium hydride 1 M in THF under a nitrogen atmosphere. Then the reaction mixture is stirred for 3 hours at 75° C. Then the reaction mixture is carefully quenched with a little water and 1 M sodium hydroxide solution. The reaction mixture is filtered, the filtrate is evaporated to dryness in vacuo. The residue is taken up in dichloromethane, filtered and again evaporated to dryness in vacuo.

$C_{12}H_{18}N_2$ (190.28)

[M+H]+=191

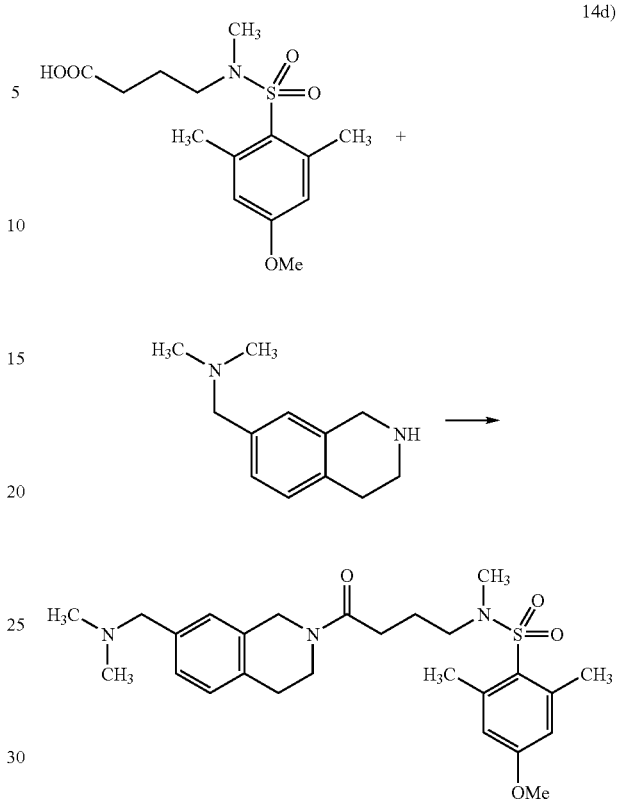

14d)

Example 14 is prepared analogously to 1 g from 50.0 mg (0.16 mmol) of 4-[(4-methoxy-2,6-dimethylbenzolsulphonyl)-methylamino]-butyric acid (prepared analogously to 1a-1d), 60.3 mg (0.32 mmol) of product from 14c, 0.11 ml (0.79 mmol) of triethylamine and 56.0 mg (0.17 mmol) of TBTU in 0.5 ml DMF.

$C_{26}H_{37}N_3O_4S$ (487.66)

[M+H]+=488

HPLC (Method 2): retention time=1.60 min

The following compounds (Example 15-16) were prepared analogously to Example 14:

Example 15

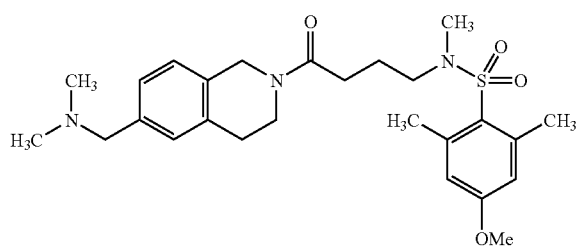

$C_{26}H_{37}N_3O_4S$ (487.66)

[M+H]+=488

HPLC (Method 2): retention time=1.60 min

Example 16

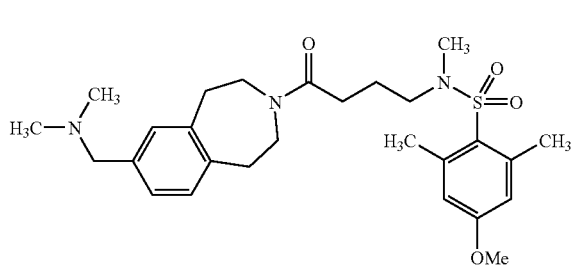

C₂₇H₃₉N₃O₄S (501.68)
[M+H]+=502
HPLC (Method 2): retention time=1.53 min

Example 17

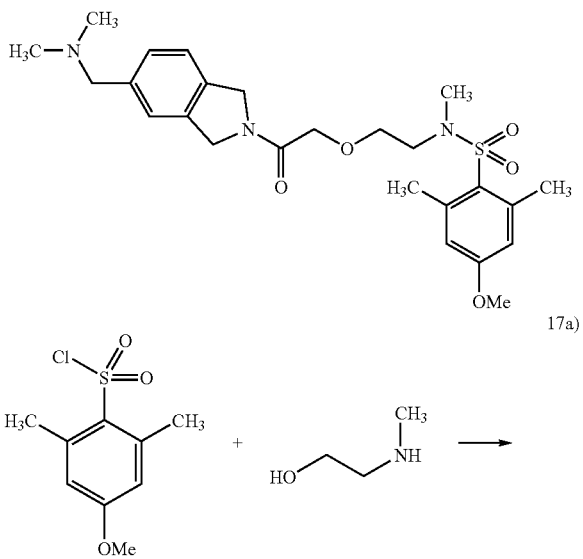

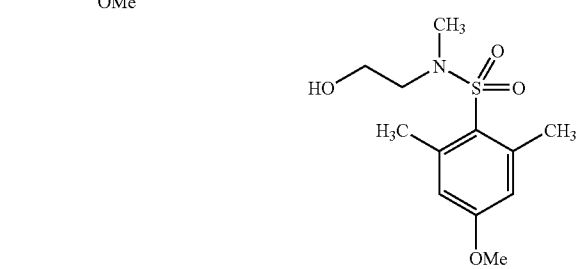

A mixture of 4.50 g (19.17 mmol) of product from 1a, 1.69 g (21.10 mmol) of N-methylaminoethanol (BASF), 6.68 ml (47.90 mmol) of triethylamine and 150 ml dichloromethane is stirred overnight at ambient temperature. The reaction mixture is then washed with 0.5 M HCl, saturated sodium hydrogen carbonate solution, water and saturated sodium chloride solution, dried on sodium sulphate and evaporated to dryness in vacuo.

C₁₂H₁₉NO₄S (273.35)
[M+H]+=274
TLC: silica gel, dichloromethane/ethanol 19:1, Rf value=0.43

17b)

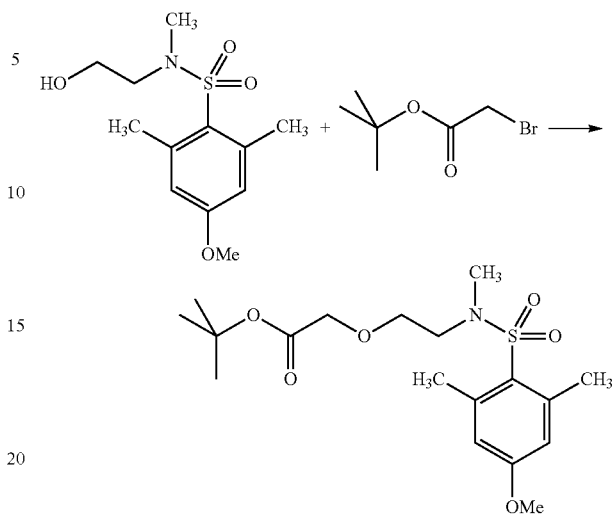

A mixture of 5.15 g (18.84 mmol) of product from 17a, 1.75 g (6.60 mmol) of tetrabutylammonium chloride (Fluka) and 80 ml of toluene is combined at 0° C. first with 100 ml of 35% sodium hydroxide solution, then with 4.18 ml (28.26 mmol) of tert-butyl bromoacetate in 20 ml of toluene. The reaction mixture is then stirred for 1.5 hours at ambient temperature, then diluted with diethyl ether. After the phase separation the organic phase is washed four times with water until neutral, dried on sodium sulphate and evaporated to dryness in vacuo. The crude product thus obtained is purified by column chromatography through silica gel (eluant: petroleum ether/ethyl acetate 4:1).

C₁₈H₂₉NO₆S (387.49)
[M+H]+=388
TLC: silica gel, petroleum ether/ethyl acetate 7:3, Rf value=0.59

17c)

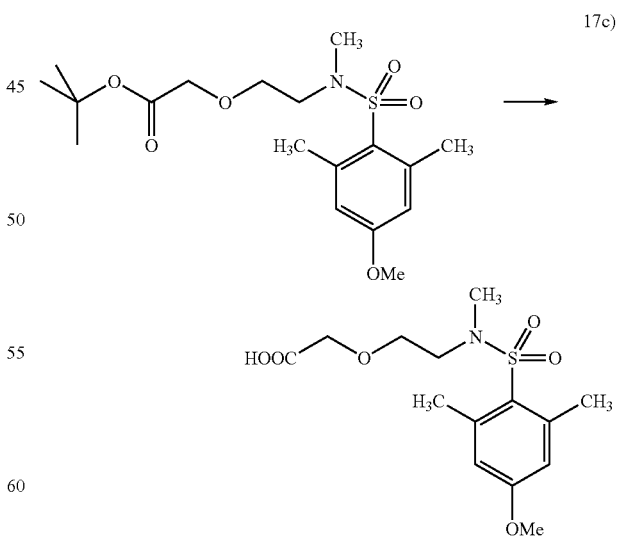

A mixture of 6.80 g (17.55 mmol) of product from 17b, 8 ml TFA and 100 ml dichloromethane is stirred for 2.5 hours at ambient temperature. The reaction mixture is then evaporated to dryness in vacuo. The residue is combined with 1 M sodium hydroxide solution and extracted twice with ethyl acetate (organic extracts are discarded). The aqueous phase is acidified with 2 M HCl, then extracted again with ethyl acetate. The organic extracts are washed with water, dried on sodium sulphate and evaporated to dryness in vacuo.

$C_{14}H_{21}NO_6S$ (331.29)
[M+H]+=332
HPLC (Method 3): retention time=3.4 min

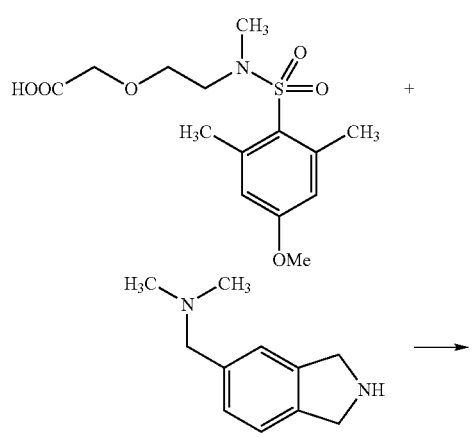

17d)

Example 17 is prepared analogously to 1 g from 0.10 g (0.30 mmol) of product from 17c, 0.43 g (2.44 mmol) of product from 13a, 1.0 ml (7.19 mmol) of triethylamine and 0.50 g (1.56 mmol) of TBTU in 10 ml DMF.

$C_{25}H_{35}N_3O_5S$ (489.63)
[M+H]+=490
HPLC (Method 4): retention time=1.50 min Example 18

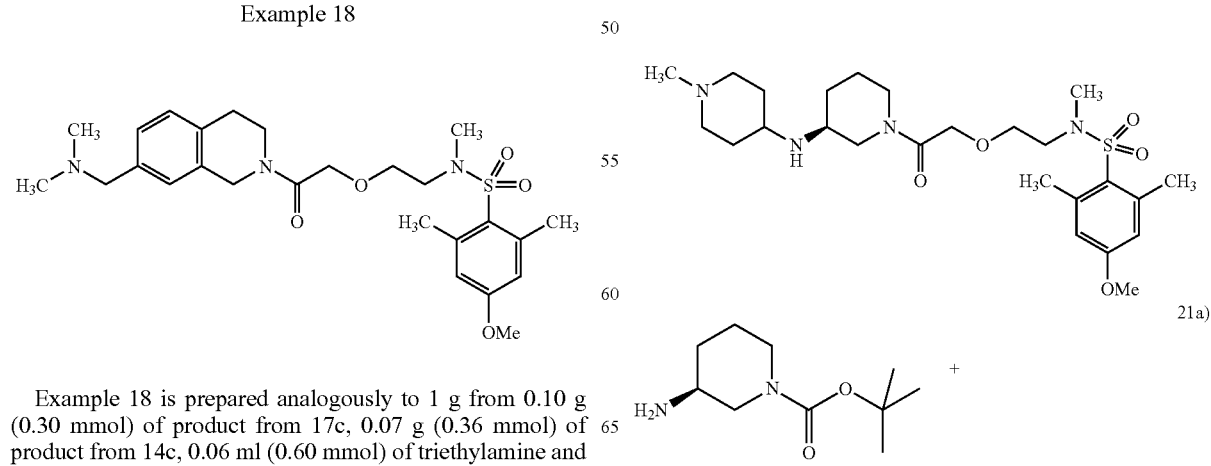

Example 18 is prepared analogously to 1 g from 0.10 g (0.30 mmol) of product from 17c, 0.07 g (0.36 mmol) of product from 14c, 0.06 ml (0.60 mmol) of triethylamine and 0.12 g (0.36 mmol) of TBTU in 5 ml DMF.

$C_{26}H_{37}N_3O_5S \times HCl$ (540.12)
[M+H]+=504
HPLC (Method 4): retention time=1.50 min The following compounds (Example 19-20) were prepared analogously to Example 18:

Example 19

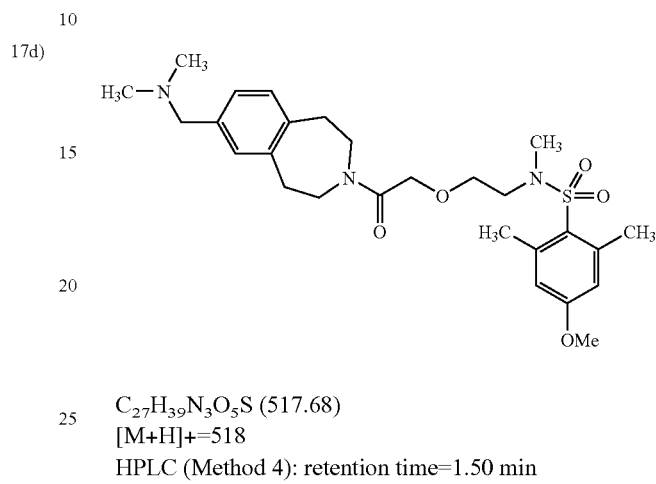

$C_{27}H_{39}N_3O_5S$ (517.68)
[M+H]+=518
HPLC (Method 4): retention time=1.50 min Example 20

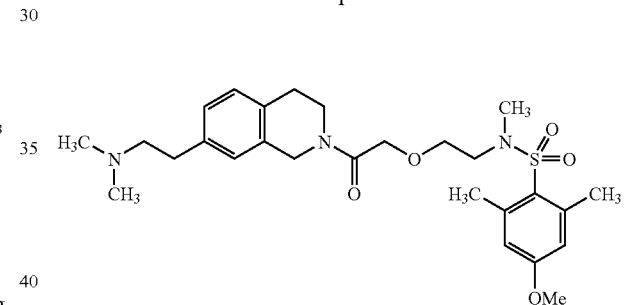

$C_{27}H_{39}N_3O_5S \times HCl$ (554.14)
[M+H]+=518
HPLC (Method 4): retention time=1.56 min Example 21

21a)

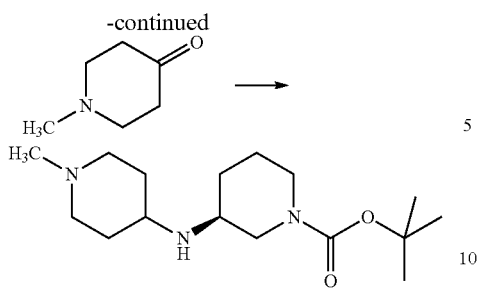

A mixture of 0.20 g (1.00 mmol) of (S)-3-amino-1-N-Boc-piperidine (Arch), 0.08 ml (1.47 mmol) of acetic acid, 0.11 g (1.00 mmol) of N-methyl-4-piperidone (Aldrich) and 1.9 ml dichloromethane is stirred for 20 minutes at ambient temperature. The reaction mixture is then combined with 0.30 g (1.43 mmol) of sodium triacetoxyborohydride and stirred overnight at ambient temperature. Then the reaction mixture is quenched with saturated potassium carbonate solution and the phases are separated. The aqueous phase is extracted twice more with dichloromethane. The combined organic phases are dried on sodium sulphate and evaporated to dryness in vacuo.

$C_{16}H_{31}N_3O_2$ (297.44)

[M+H]+=298

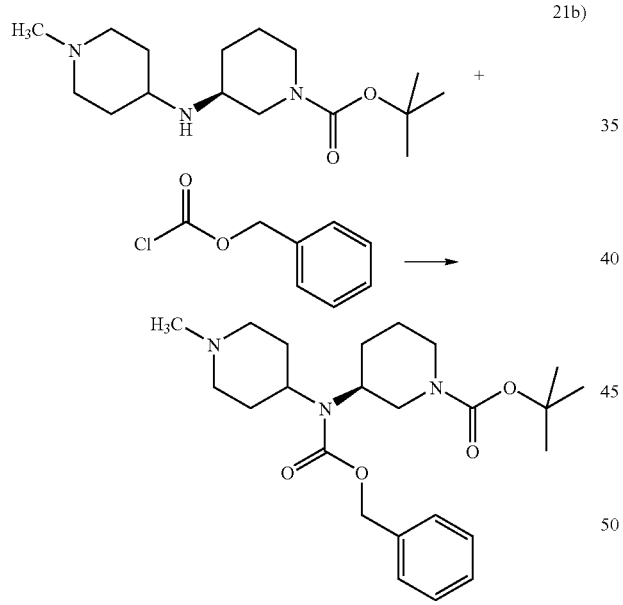

A mixture of 0.30 g (1.02 mmol) of product from 21a, 0.57 ml (4.09 mmol) of triethylamine and 7.5 ml dichloromethane is combined with 0.22 ml (1.23 mmol) of benzylchloroformate 95% while cooling with an ice bath. The reaction mixture is then stirred for 4 hours at ambient temperature. Then it is washed with water and saturated sodium chloride solution, dried on sodium sulphate and evaporated to dryness in vacuo. The crude product thus obtained is purified by column chromatography through silica gel (eluant: dichloromethane/methanol/ammonia 9:1:0.1).

$C_{24}H_{37}N_3O_4$ (431.57)

[M+H]+=432

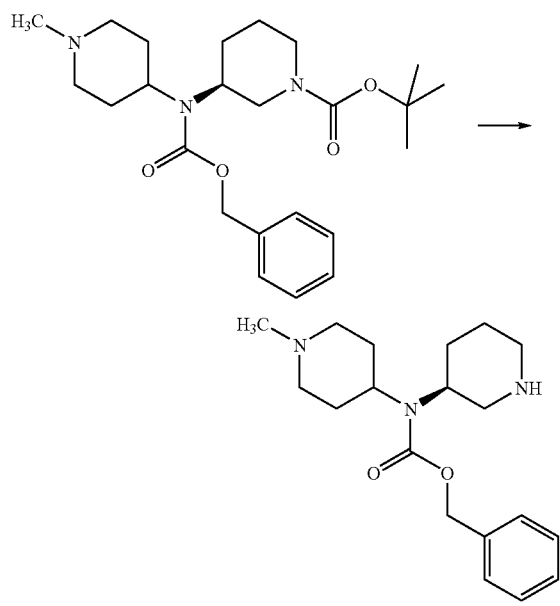

A mixture of 0.15 g (0.35 mmol) of product from 21b, 2.30 ml (9.18 mmol) of HCl 4 M in dioxane and 1 ml of methanol is stirred overnight at ambient temperature.

Then the reaction mixture is evaporated to dryness in vacuo.

$C_{19}H_{29}N_3O_2 \times 2HCl$ (404.38)

[M+H]+=332

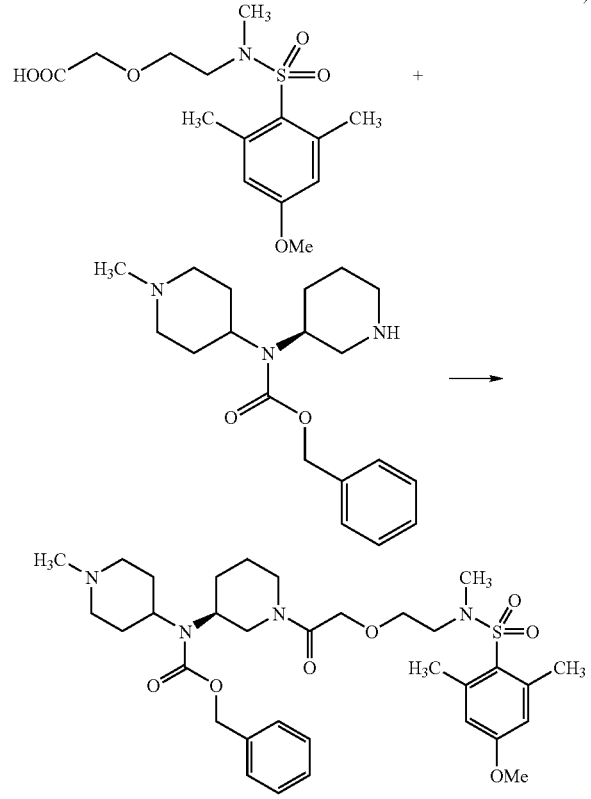

21d is prepared analogously to 1 g from 0.10 g (0.30 mmol) of product from 17c, 0.13 g (0.30 mmol) of product from 21c, 0.17 ml (1.21 mmol) of triethylamine and 0.10 g (0.30 mmol) of TBTU in 4 ml THF.

$C_{33}H_{48}N_4O_7S$ (644.82)

[M+H]+=645

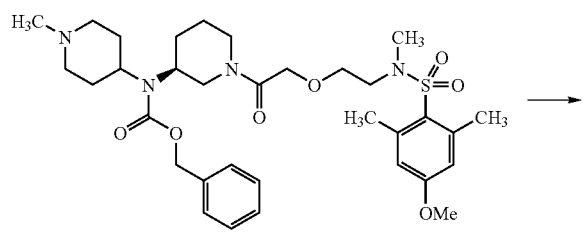

21e)

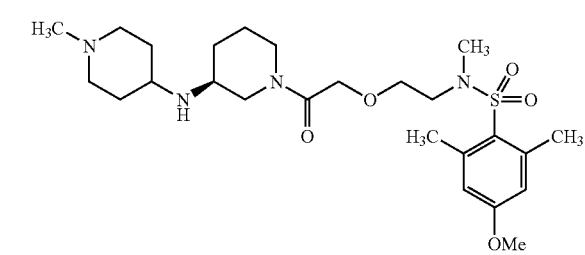

A mixture of 0.13 g (0.20 mmol) of product from 21d, 20 mg palladium on charcoal 10% and 50 ml of methanol is hydrogenated for 18 hours in the autoclave at ambient temperature. Then the catalyst is filtered off and the filtrate is evaporated to dryness in vacuo.

$C_{25}H_{42}N_4O_5S$ (510.69)

[M+H]+=511

HPLC (Method 4): retention time=1.38 min

The following compounds (Example 22-23) were prepared analogously to Example 21:

Example 22

$C_{25}H_{42}N_4O_5S$ (510.69)

[M+H]+=511

HPLC (Method 4): retention time=1.36 min

Example 23

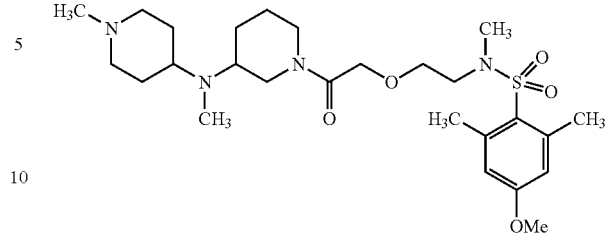

$C_{26}H_{44}N_4O_5S \times 2HCl$ (597.64)

[M+H]+=525

HPLC (Method 4): retention time=1.14 min

Example 24

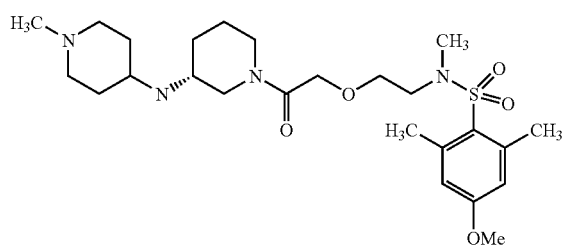

24a)

A mixture of 1.70 g (44.80 mmol) of lithium aluminium hydride and 30 ml THF is slowly combined with 1.69 g (7.97 mmol) of (4-methylpiperazin-1-yl)-piperidin-3-yl-methanone (analogously to Bioorg. Med. Chem. Lett. 16, 2006, 204-207) in 30 ml THF at 65° C. The reaction mixture is then stirred for three hours at 65° C. and overnight at ambient temperature. Then the reaction mixture is carefully hydrolysed with water and 1 M sodium hydroxide solution while cooling with an ice bath and filtered through Celite. The filtrate is evaporated to dryness in vacuo.

$C_{11}H_{23}N_3$ (197.32)

[M+H]+=198

24b)

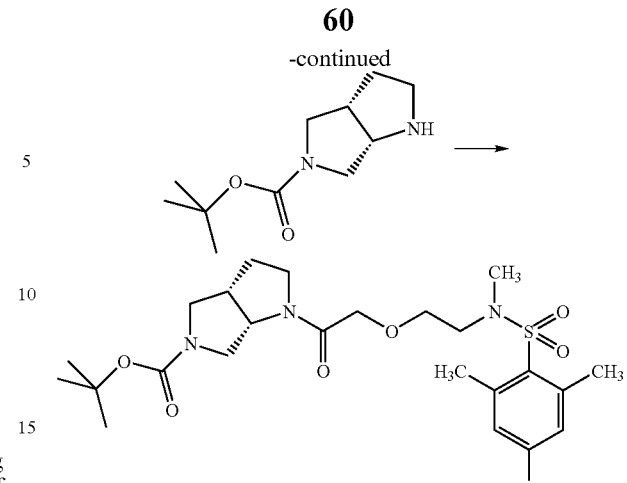

Example 24 is prepared analogously to 1 g from 0.34 g (1.02 mmol) of product from 17c, 0.21 g (1.06 mmol) of product from 24a, 0.35 ml (2.54 mmol) of triethylamine and 0.39 g (1.22 mmol) of TBTU in 15 ml DMF.

$C_{25}H_{42}N_4O_5S \times 2HCl$ (583.61)
[M+H]+=511
HPLC (Method 4): retention time=1.40 min The following compound (Example 25) was prepared analogously to Example 24:

Example 25

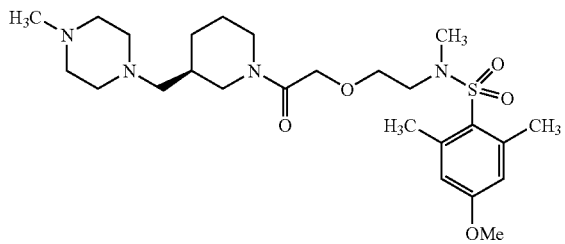

$C_{25}H_{42}N_4O_5S \times 2HCl$ (583.61)
[M+H]+=511
HPLC (Method 4): retention time=1.39 min Example 26

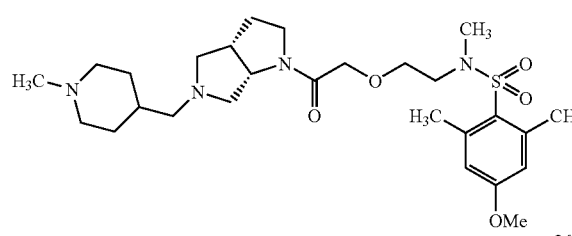

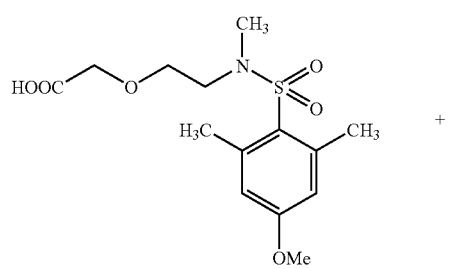

26a)

26a is prepared analogously to 1 g from 0.99 g (3.00 mmol) of product from 17c, 0.64 g (3.00 mmol) of tert-butyl (3aS, 6aS)-hexahydropyrrol[3,4-b]pyrrole-5-carboxylate (enamine), 1.29 ml (7.50 mmol) of DIPEA and 1.00 g (3.00 mmol) of TBTU in 20 ml DMF.

$C_{25}H_{39}N_3O_7S$ (525.66)
HPLC (Method 2): retention time=2.36 min

26b)

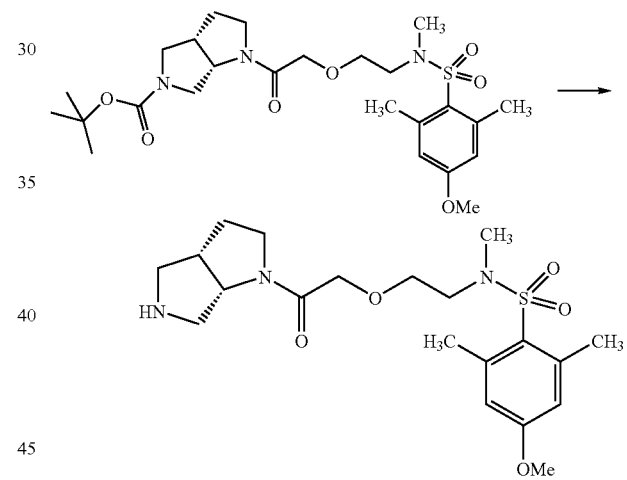

26b is prepared analogously to 14b from 1.50 g (2.85 mmol) of product from 26a, 12 ml TFA and 12 ml dichloromethane.

$C_{20}H_{31}N_3O_5S$ (425.54)
[M+H]+=426
HPLC (Method 2): retention time=1.40 min 26c)

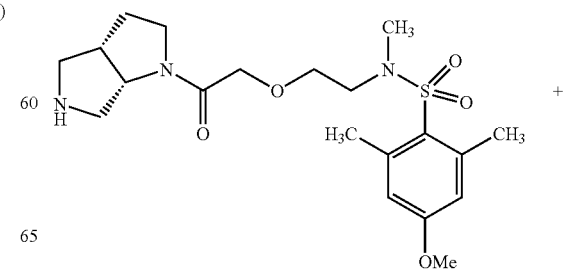

+

-continued

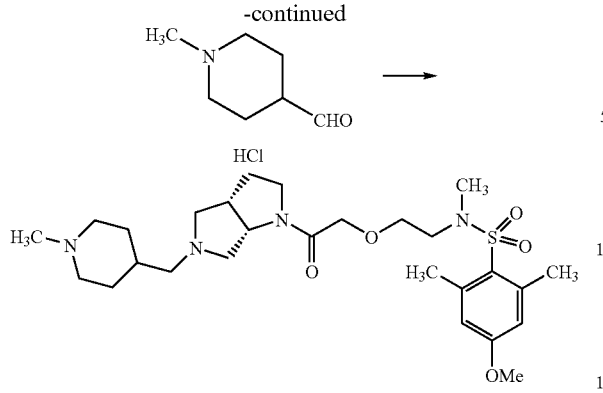

Example 26 is prepared analogously to 1e from 0.21 g (0.50 mmol) of product from 26b, 82 mg (0.50 mmol) of 1-methylpiperidine-4-carbaldehyde hydrochloride (Chembridge), 0.16 g (0.75 mmol) of sodium triacetoxyborohydride, 0.06 ml (1.00 mmol) of acetic acid and 7 ml THF.

$C_{27}H_{44}N_4O_5S \times 2C_2HF_3O_2$ (764.77)
[M+H]+=537
HPLC (Method 2): retention time=1.32 min The following compounds (Example 27-35) were prepared analogously to Example 26:

Example 27

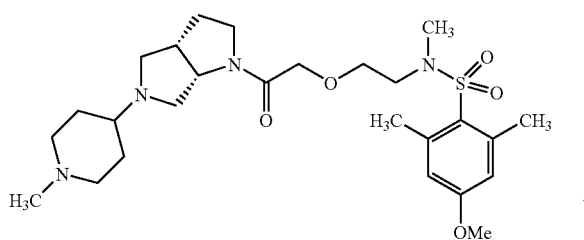

$C_{26}H_{42}N_4O_5S \times 2C_2HF_3O_2$ (750.75)
[M+H]+=523
HPLC (Method 2): retention time=1.30 min Example 28

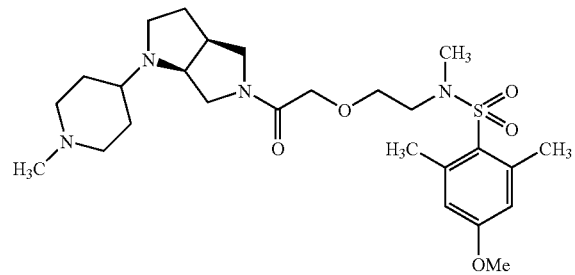

$C_{26}H_{42}N_4O_5S \times 2HCl$ (595.62)
[M+H]+=523
HPLC (Method 2): retention time=1.22 min Example 29

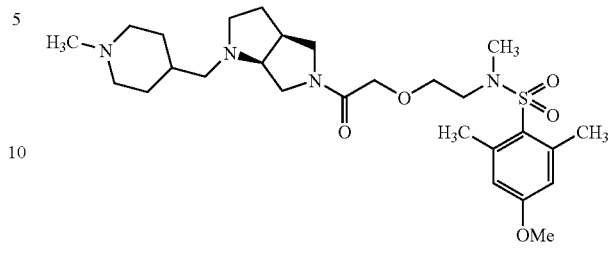

$C_{27}H_{44}N_4O_5S \times 2C_2HF_3O_2$ (764.77)
[M+H]+=537
HPLC (Method 2): retention time=1.27 min Example 30

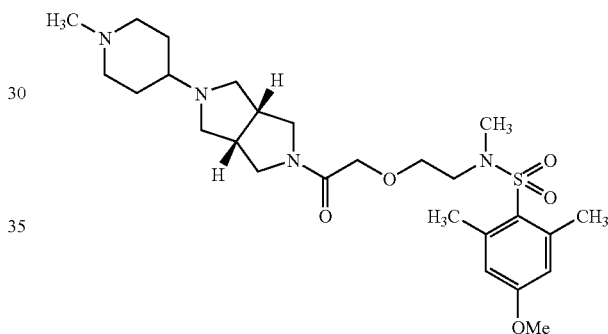

$C_{26}H_{42}N_4O_5S \times 2C_2HF_3O_2$ (750.75)
[M+H]+=523
HPLC (Method 2): retention time=1.24 min Example 31

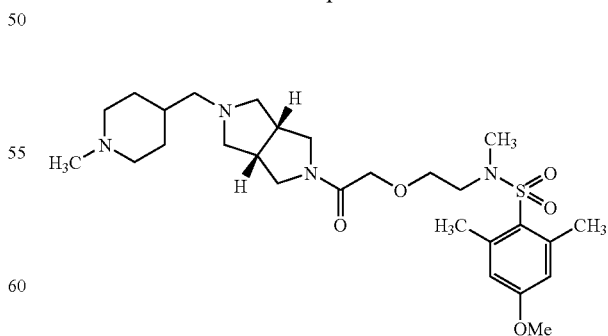

$C_{27}H_{44}N_4O_5S \times CH_2O_2$ (582.75)
[M+H]+=537
HPLC (Method 2): retention time=1.29 min

Example 32

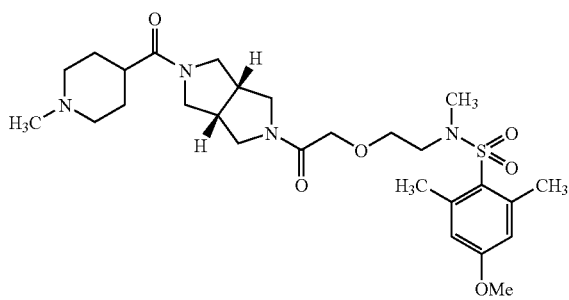

C$_{27}$H$_{42}$N$_4$O$_6$S×C$_2$HF$_3$O$_2$ (664.74)

[M+H]+=551

HPLC (Method x): retention time=? min

Example 33

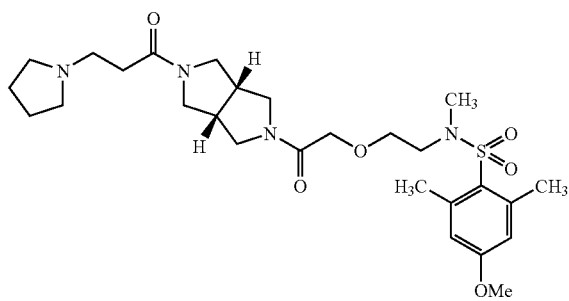 [SMILES: COc1cc(C)c(S(=O)(=O)N(C)CCOCC(=O)N2C[C@H]3CN(C(=O)CCN4CCCC4)C[C@H]3C2)c(C)c1]

C$_{26}$H$_{40}$N$_4$O$_6$S×C$_2$HF$_3$O$_2$ (650.71)

[M+H]+=537

HPLC (Method x): retention time=? min

Example 34

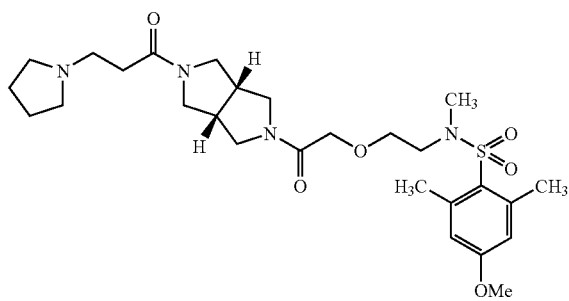 [SMILES: COc1cc(C)c(S(=O)(=O)N(C)CCOCC(=O)N2C[C@H]3CN(C(=O)CCN4CCCC4)C[C@H]3C2)c(C)c1]

C$_{27}$H$_{42}$N$_4$O$_6$S (550.71)

[M+H]+=551

HPLC (Method x): retention time=? min

Example 35

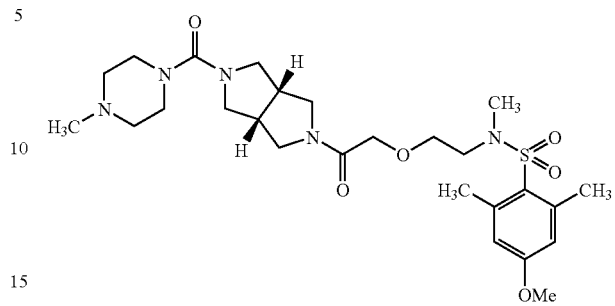

C$_{26}$H$_{41}$N$_5$O$_6$S (551.70)

[M+H]+=552

HPLC (Method x): retention time=? min

Example 36

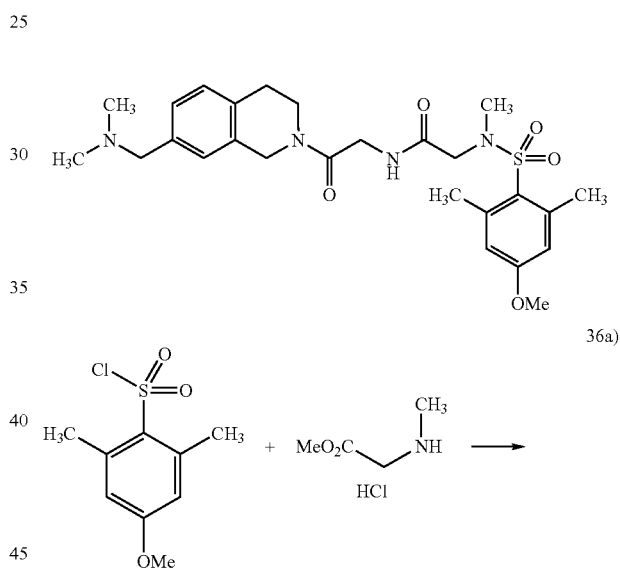

36a)

A mixture of 1.65 g (7.05 mmol) of product from 1a, 0.98 g (7.05 mmol) of sarcosine methylester hydrochloride (Fluke) and 50 ml of pyridine is stirred for one hour at ambient temperature. The reaction mixture is then evaporated to dryness in vacuo. The residue is then taken up in 1 M HCl and extracted with ethyl acetate. The organic extracts are dried on sodium sulphate and evaporated to dryness in vacuo.

C$_{13}$H$_{19}$NO$_5$S (301.36)

[M+H]+=302

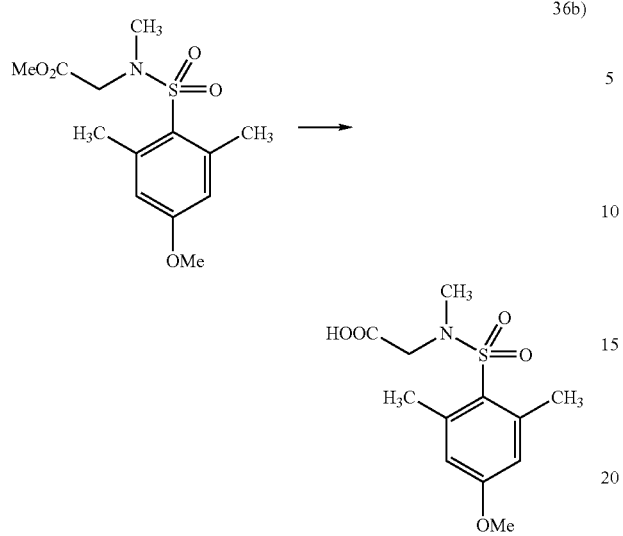

A mixture of 1.90 g (6.29 mmol) of product from 36a, 6.45 ml (12.90 mmol) of 2 M sodium hydroxide solution and 9 ml of methanol is stirred for three days at ambient temperature. The methanol is eliminated in vacuo, the aqueous residue is poured onto 1 M HCl. The precipitate formed is filtered off and dried overnight in the vacuum desiccator.

$C_{12}H_{17}NO_5S$ (287.33)

[M+H]+=288

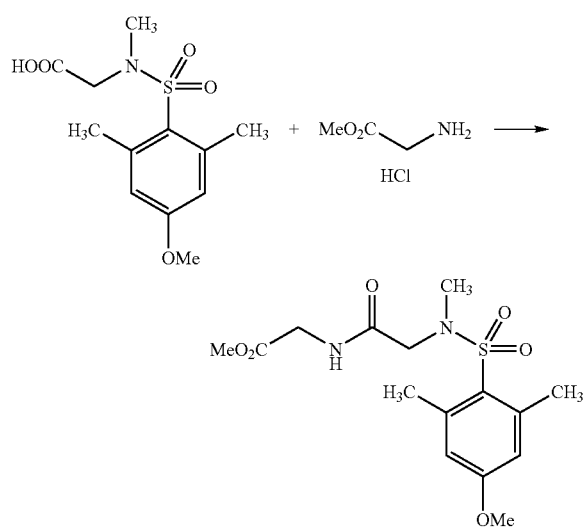

36c is prepared analogously to 1 g from 0.20 g (0.70 mmol) of product from 36b, 0.087 g (0.70 mmol) of glycine methylester hydrochloride (Aldrich), 0.29 ml (2.09 mmol) of triethylamine and 0.22 g (0.70 mmol) of TBTU in 5 ml THF.

$C_{15}H_{22}N_2O_6S$ (358.41)

[M+H]+=359

HPLC (Method 5): retention time=1.72 min

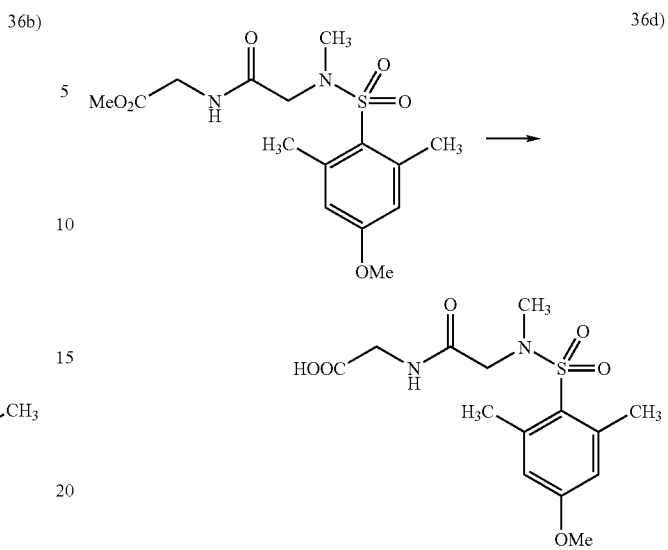

36d is prepared analogously to 36b from 0.23 g (0.63 mmol) of product from 36c and 0.64 ml (1.29 mmol) of 2 M sodium hydroxide solution in 1 ml of methanol.

$C_{14}H_{20}N_2O_6S$ (344.38)

[M+H]+=345

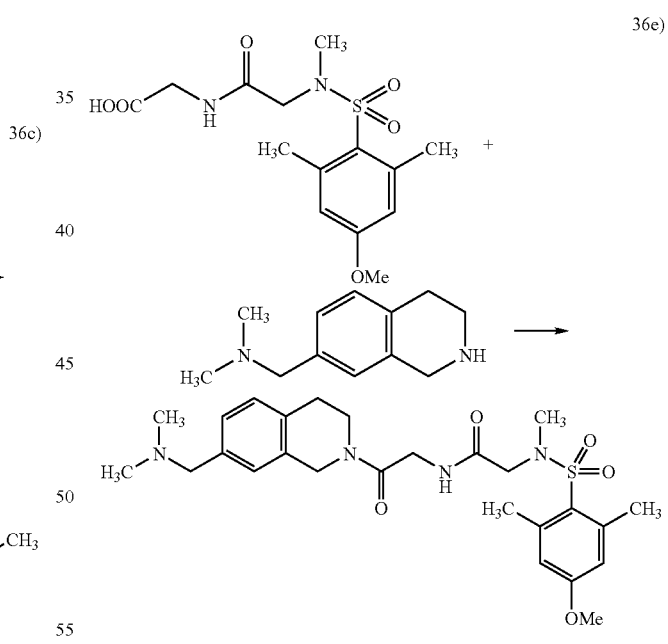

Example 36 is prepared analogously to 1 g from 0.10 g (0.29 mmol) of product from 36d, 0.07 g (0.35 mmol) of product from 14c, 59 µl (0.58 mmol) of triethylamine and 0.11 g (0.35 mmol) of TBTU in 5 ml DMF.

$C_{26}H_{36}N_4O_5S \times HCl$ (553.11)

[M+H]+=517

HPLC (Method 4): retention time=1.46 min

The following compounds (Example 37-39) were prepared analogously to Example 36:

Example 37

C$_{27}$H$_{38}$N$_4$O$_5$S×HCl (567.14)
[M+H]+=531
HPLC (Method 4): retention time=1.54 min

Example 38

C$_{26}$H$_{36}$N$_4$O$_5$S×HCl (553.11)
[M+H]+=517
HPLC (Method 5): retention time=1.73 min

Example 39

C$_{27}$H$_{38}$N$_4$O$_5$S (530.68)
[M+H]+=531
HPLC (Method 4): retention time=1.49 min The following Examples describe pharmaceutical formulations which contain as active substance any desired compound of general formula I:

Example I

Dry Ampoule with 75 mg of Active Compound Per 10 ml

Composition:

| | |
|---|---|
| Active compound | 75.0 mg |
| Mannitol | 50.0 mg |
| Water for injection | ad 10.0 ml |

Production:

Active compound and mannitol are dissolved in water. The charged ampoules are freeze dried. Water for injection is used to dissolve to give the solution ready for use.

Example II

Tablet with 50 mg of Active Compound

Composition:

| | |
|---|---|
| (1) Active compound | 50.0 mg |
| (2) Lactose | 98.0 mg |
| (3) Maize starch | 50.0 mg |
| (4) Polyvinylpyrrolidone | 15.0 mg |
| (5) Magnesium stearate | 2.0 mg |
| | 215.0 mg |

Production:

(1), (2) and (3) are mixed and granulated with an aqueous solution of (4). (5) is admixed to the dry granules. Tablets are compressed from this mixture, biplanar with a bevel on both sides and dividing groove on one side.

Diameter of the tablets: 9 mm.

Example III

Tablet with 350 mg of Active Compound

Composition:

| | |
|---|---|
| (1) Active compound | 350.0 mg |
| (2) Lactose | 136.0 mg |
| (3) Maize starch | 80.0 mg |
| (4) Polyvinylpyrrolidone | 30.0 mg |
| (5) Magnesium stearate | 4.0 mg |
| | 600.0 mg |

Production:

(1), (2) and (3) are mixed and granulated with an aqueous solution of (4). (5) is admixed to the dry granules. Tablets are compressed from this mixture, biplanar with a bevel on both sides and dividing groove on one side.

Diameter of the tablets: 12 mm.

Example IV

Capsule with 50 mg of Active Compound

Composition:

| | |
|---|---|
| (1) Active compound | 50.0 mg |
| (2) Maize starch dried | 58.0 mg |
| (3) Lactose powdered | 50.0 mg |
| (4) Magnesium stearate | 2.0 mg |
| | 160.0 mg |

Production:

(1) is triturated with (3). This trituration is added to the mixture of (2) and (4) with vigorous mixing.

This powder mixture is packed into hard gelatine two-piece capsules of size 3 in a capsule-filling machine.

Example V

Capsules with 350 mg of Active Compound

Composition:

| | | |
|---|---|---|
| (1) Active compound | 350.0 mg | |
| (2) Maize starch dried | 46.0 mg | |
| (3) Lactose powdered | 30.0 mg | |
| (4) Magnesium stearate | 4.0 mg | |
| | 430.0 mg | |

Production:

(1) is triturated with (3). This trituration is added to the mixture of (2) and (4) with vigorous stirring.

This powder mixture is packed into hard gelatine two-piece capsules of size 0 in a capsule-filling machine.

Example VI

Suppositories with 100 mg of Active Compound 1 suppository comprises:

| | |
|---|---|
| Active compound | 100.0 mg |
| Polyethylene glycol (M.W. 1500) | 600.0 mg |
| Polyethylene glycol (M.W. 6000) | 460.0 mg |
| Polyethylene sorbitan monostearate | 840.0 mg |
| | 2000.0 mg |

The invention claimed is:

1. A compound of the formula I

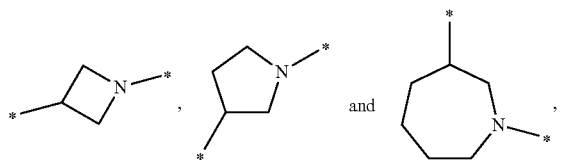

(I)

wherein

A denotes
  a) a bond,
  b) $C_{1-4}$-alkylene,
  c) —N($R^2$),
  d) —C(O),
  e) a saturated 5- or 6-membered aza heterocyclic group or
  f) a saturated 6- or 7-membered diaza heterocyclic group, Y denotes a $C_{1-6}$-alkylene group optionally substituted by the group $R^2$, while a methylene group contained therein may additionally be replaced by $Y^1$ and $Y^1$ denotes —O—, —S—, —S(O)—, —N($R^2$)—, —N($R^2$)—C(O)—, —C(O)—N($R^2$)—, —C(O)—, —CH(aryl) or —S(O)$_2$—, $R^1$ denotes
  a) aryl or
  b) heteroaryl,
  while the previously mentioned aryl and heteroaryl groups may each be substituted by one, two, three or four groups $R^{1.1}$ and the groups $R^{1.1}$ may be identical or different and
  $R^{1.1}$ denotes H, F, Cl, Br, I, $C_{1-3}$-alkyl, $F_3C$, HO, $C_{1-3}$-alkyl-O or $C_{1-3}$-alkyl-O—$C_{2-4}$-alkylene-O—, $R^2$ denotes
  a) H or
  b) $C_{1-3}$-alkyl, while each methylene group may be substituted by up to two and each methyl group may be substituted by up to three fluorine atoms, $R^3$ denotes
  a) a saturated 4- to 7-membered aza heterocyclic group which is selected from among

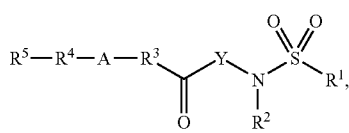

b) a monounsaturated 5- to 7-membered aza heterocyclic group, wherein an olefinic double bond is fused to a group $R^{3.1}$, or
  c) a saturated 8- to 10-membered diaza-heterobicyclic group with the proviso that one of A, R4 or R5 is an aza heterocyclic group,
and
  $R^{3.1}$ denotes phenyl or pyridyl,
  while the groups $R^{3.1}$ in the carbon skeleton may additionally be substituted by one, two or three identical or different groups $R^{3.1.1}$ and
  $R^{3.1.1}$ denotes F, Cl, Br, I, $H_3C$ or $F_3C$—, $R^4$ denotes
  a) a bond,
  b) $C_{1-3}$-alkylene
  c) $C_{3-6}$-cycloalkylene,
  d) a saturated 4- to 7-membered aza heterocyclic group,
  e) a saturated 6- to 7-membered diaza heterocyclic group or
  f) a saturated 9- to 11-membered diaza-spirocycle, $R^5$ denotes
  a) a $C_{1-4}$-alkyl group substituted by $R^{5.1}$,
  b) $H_2N$,
  c) $C_{1-4}$-alkyl-NH—
  d) ($C_{1-4}$-alkyl)$_2$N or
  e) a saturated 4- to 6-membered aza heterocyclic group and
  $R^{5.1}$ denotes H, ($C_{1-4}$-alkyl)$_2$N or a saturated 4- to 6-membered aza heterocyclic group, or an enantiomer, diastereomer or salt thereof.

2. The compound of the formula I according to claim 1, wherein $R^1$ denotes an aryl group which is substituted in each case by one, two, three or four groups $R^{1.1}$, while the groups $R^{1.1}$ may be identical or different and $R^{1.1}$ denotes H, F, Cl, Br, I, $C_{1-3}$-alkyl, $F_3C$, HO, $C_{1-3}$-alkyl-O or $C_{1-3}$-alkyl-O—$C_{2-4}$-alkylene-O—, or an enantiomer, diastereomer or physiologically acceptable salt thereof with an organic or inorganic acid or base.

3. The compound of the formula I according to claim 1, wherein

R¹ denotes a group selected from

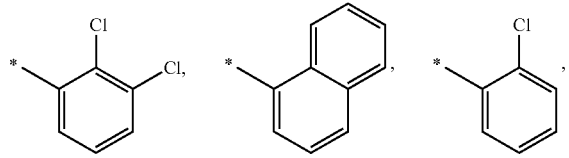

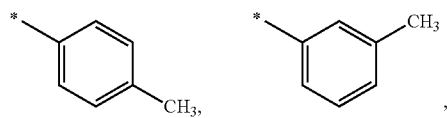

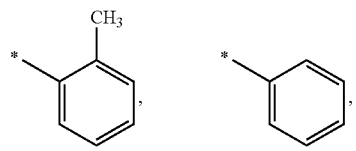

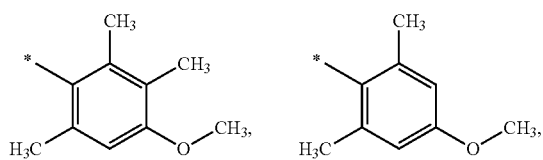

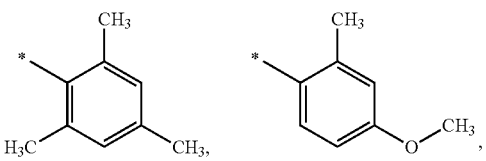

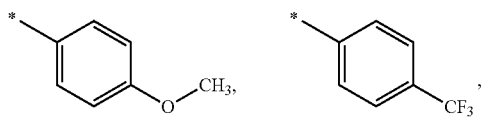

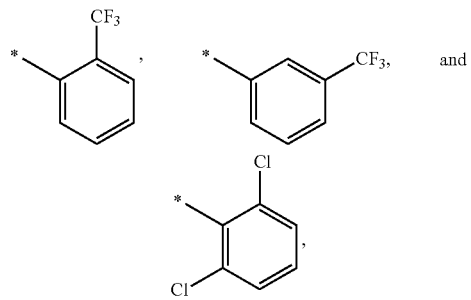

and or an enantiomer, diastereomer or physiologically acceptable salt thereof with an organic or inorganic acid or base.

4. The compound of the formula I according to claim 1, wherein

R¹ denotes the group

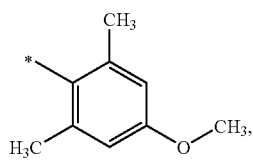

or an enantiomer, diastereomer or physiologically acceptable salt thereof with an organic or inorganic acid or base.

5. The compound of the formula I according to claim 1, wherein

R² denotes a) H or b) H₃C—, or an enantiomer, diastereomer or physiologically acceptable salt thereof with an organic or inorganic acid or base.

6. The compound of the formula I according to claim 1, wherein

Y denotes $C_{1-4}$-alkylene or a group selected from

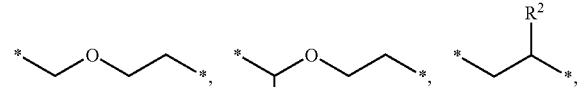

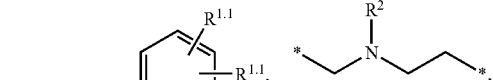

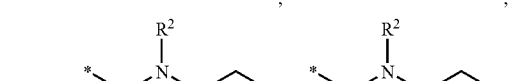

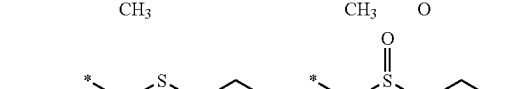

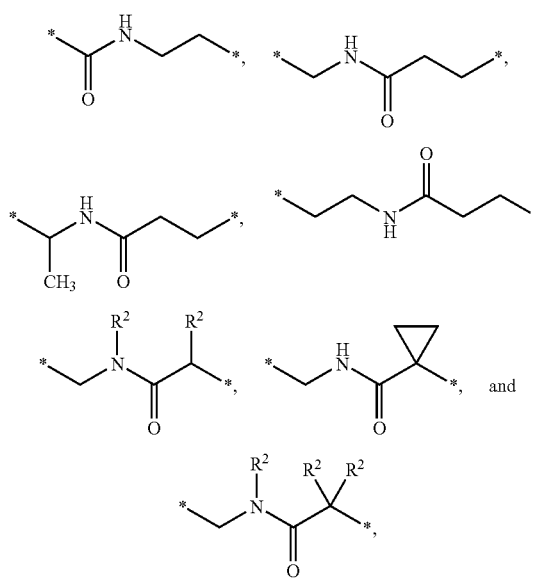

or an enantiomer, diastereomer or physiologically acceptable salt thereof with an organic or inorganic acid or base.

7. The compound of the formula I according to claim 1, wherein

Y denotes a group selected from

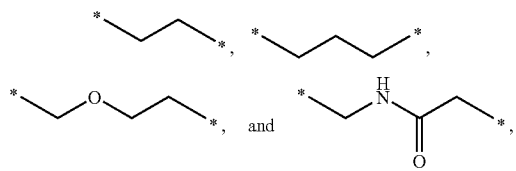

or an enantiomer, diastereomer or physiologically acceptable salt thereof with an organic or inorganic acid or base.

8. The compound of the formula I according to claim 1, wherein $R^3$ denotes a saturated 4- to 7-membered aza heterocyclic group which is selected from among

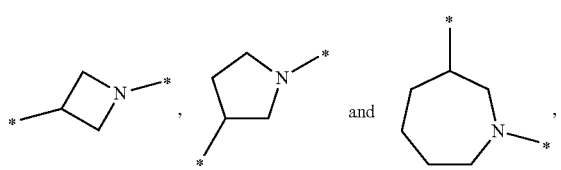

or an enantiomer, diastereomer or physiologically acceptable salt thereof with an organic or inorganic acid or base.

9. The compound of the formula I according to claim 1, wherein $R^3$ denotes a monounsaturated 5- to 7-membered aza heterocyclic group, wherein an olefinic double bond is fused to a phenyl or pyridyl group which is selected from among

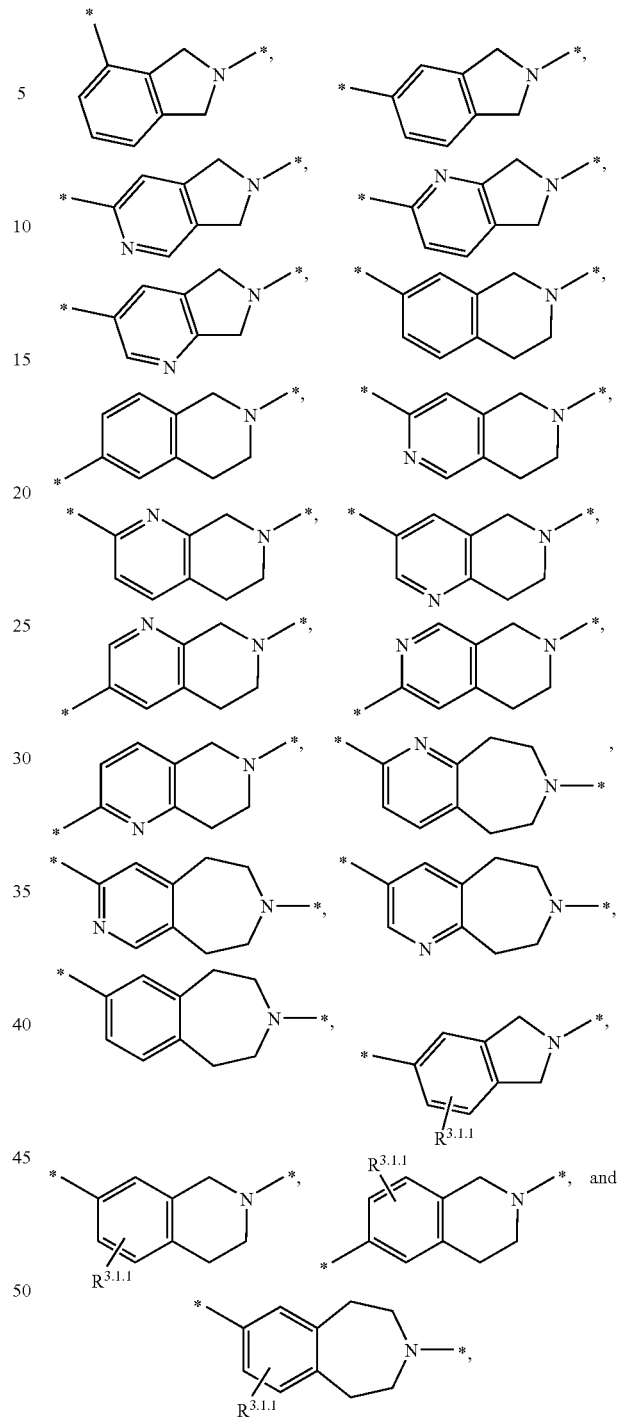

wherein $R^{3.1.1}$ denotes F, Cl, Br, I, $H_3C$ or $F_3C-$, or an enantiomer, diastereomer, a mixture thereof or a physiologically acceptable salt thereof with an organic or inorganic acid or base.

10. The compound of the formula I according to claim 1, wherein $R^3$ denotes a saturated 8- to 10-membered diaza-heterobicyclic group which is selected from among

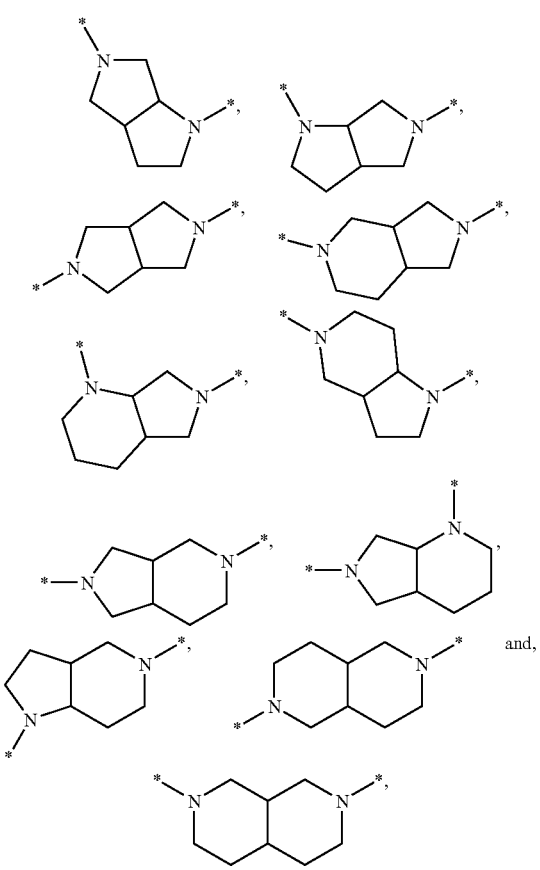

or an enantiomer, diastereomer, a mixture thereof or a physiologically acceptable salt thereof with an organic or inorganic acid or base.

11. The compound of the formula I according to claim 1, wherein $R^4$ denotes a bond, or an enantiomer, diastereomer, a mixture thereof or a physiologically acceptable salt thereof with an organic or inorganic acid or base.

12. The compound of the formula I according to claim 1, wherein $R^4$ denotes a $C_{1-3}$-alkylene group, or an enantiomer, diastereomer, a mixture thereof or a physiologically acceptable salt thereof with an organic or inorganic acid or base.

13. The compound of the formula I according to claim 1, wherein $R^4$ denotes a $C_{3-6}$-cycloalkylene group, or an enantiomer, diastereomer, a mixture thereof or a physiologically acceptable salt thereof with an organic or inorganic acid or base.

14. The compound of the formula I according to claim 1, wherein $R^4$ denotes a saturated 4- to 7-membered aza heterocyclic group which is selected from among

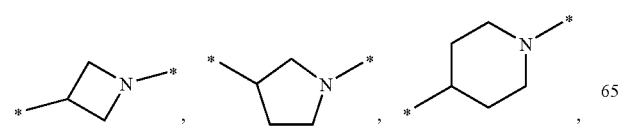

-continued

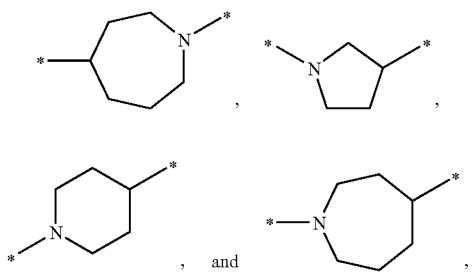

or an enantiomer, diastereomer, a mixture thereof or a physiologically acceptable salt thereof with an organic or inorganic acid or base.

15. The compound of the formula I according to claim 1, wherein $R^4$ denotes a saturated 6- to 7-membered diaza heterocyclic group selected from among

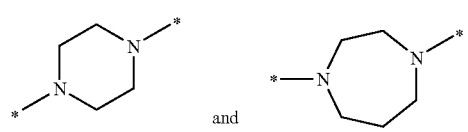

or an enantiomer, diastereomer or physiologically acceptable salt thereof with an organic or inorganic acid or base.

16. The compound of the formula I according to claim 1, wherein $R^4$ denotes a saturated 9- to 11-membered diaza-spirocycle selected from among

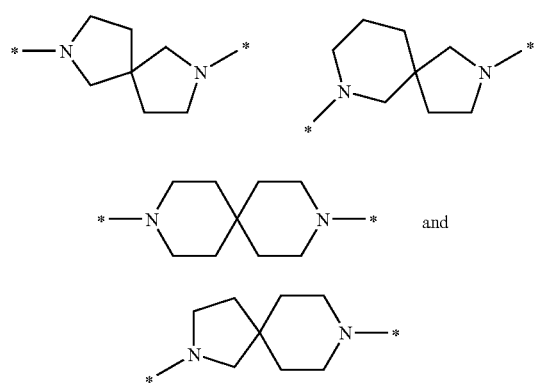

or an enantiomer, diastereomer, a mixture thereof or a physiologically acceptable salt thereof with an organic or inorganic acid or base.

17. The compound of the formula I according to claim 1, wherein

A denotes a) a bond,
b) $C_{1-4}$-alkylene,
c) —N($R^2$),
d) —C(O), e) a heterocyclic group which is selected from among
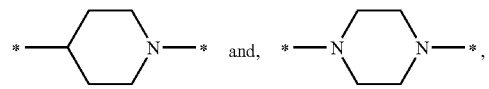
Y denotes $C_{1-4}$-alkylene or a group selected from
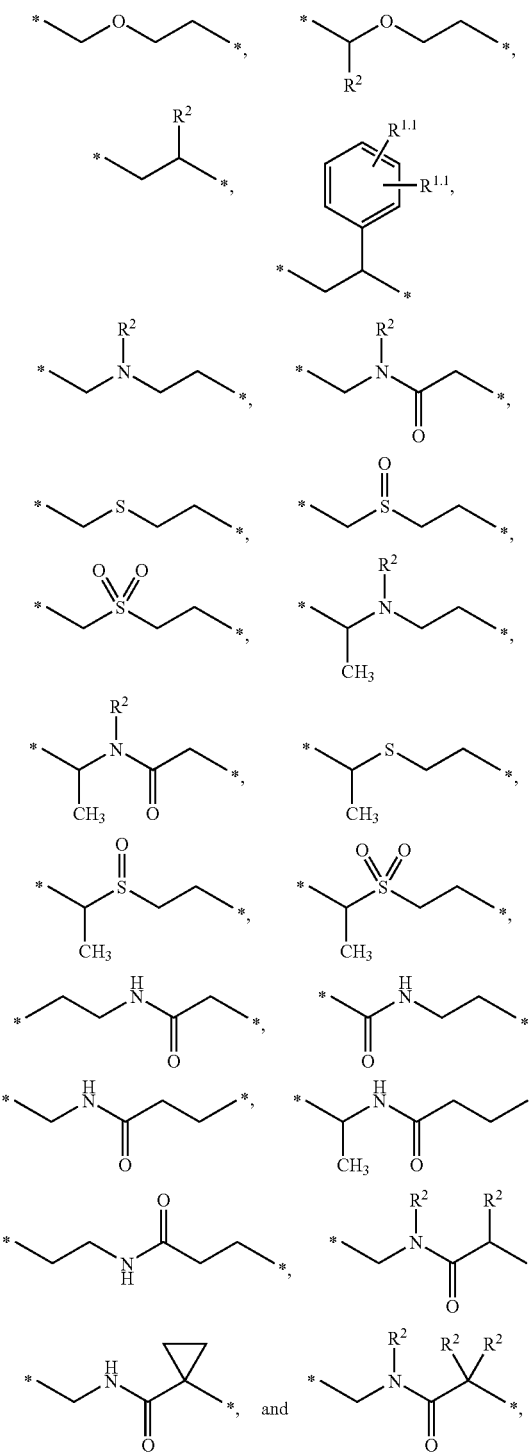
$R^1$ denotes a group selected from
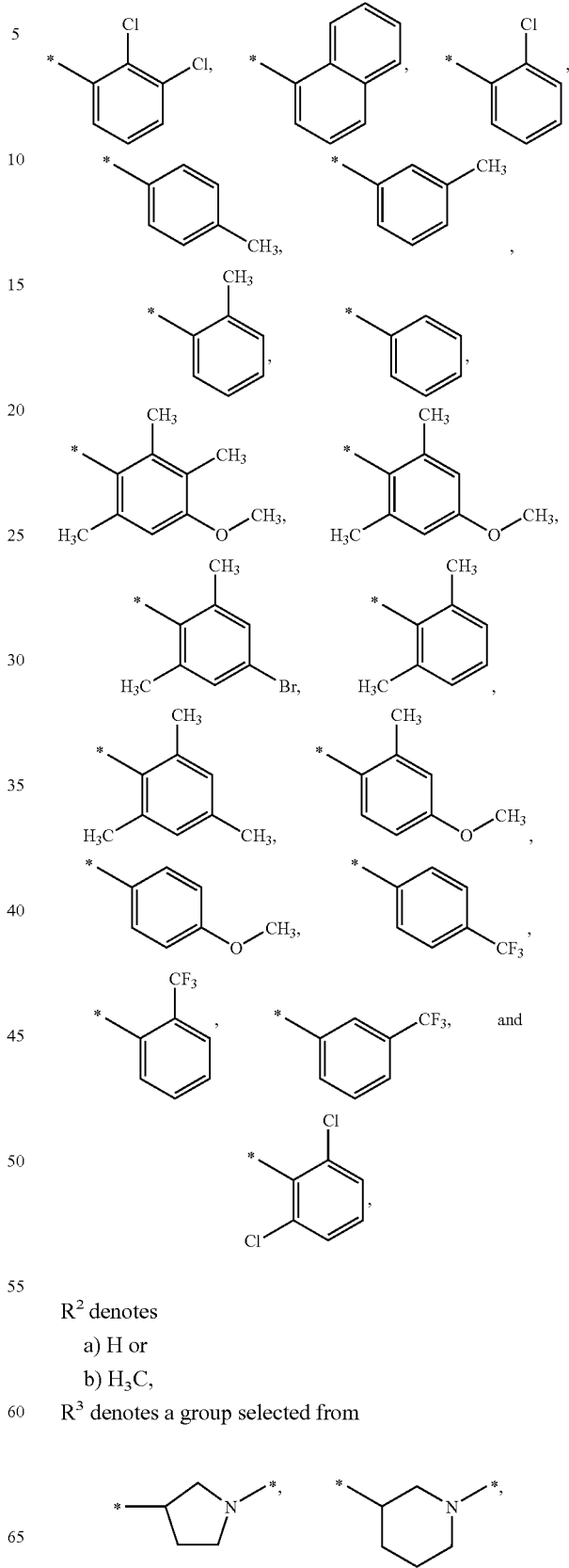
$R^2$ denotes
a) H or
b) $H_3C$,
$R^3$ denotes a group selected from

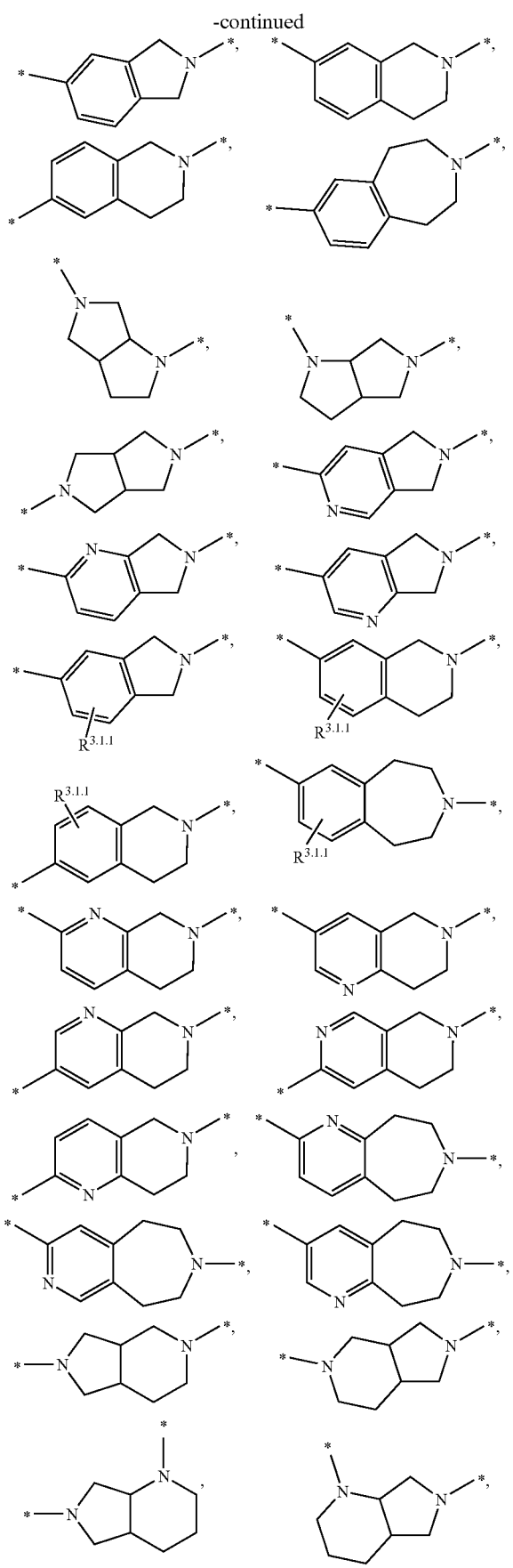
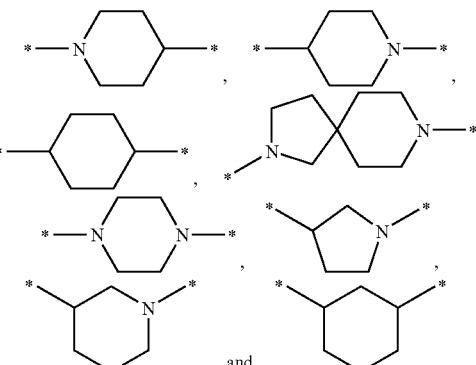
wherein
$R^{3.1.1}$ denotes F, Cl, Br, I, $H_3C$ or $F_3C$—,
$R^4$ denotes
 a) a bond,
 b) —$CH_2$ or —$(CH_2)_2$ or
 c) a group selected from
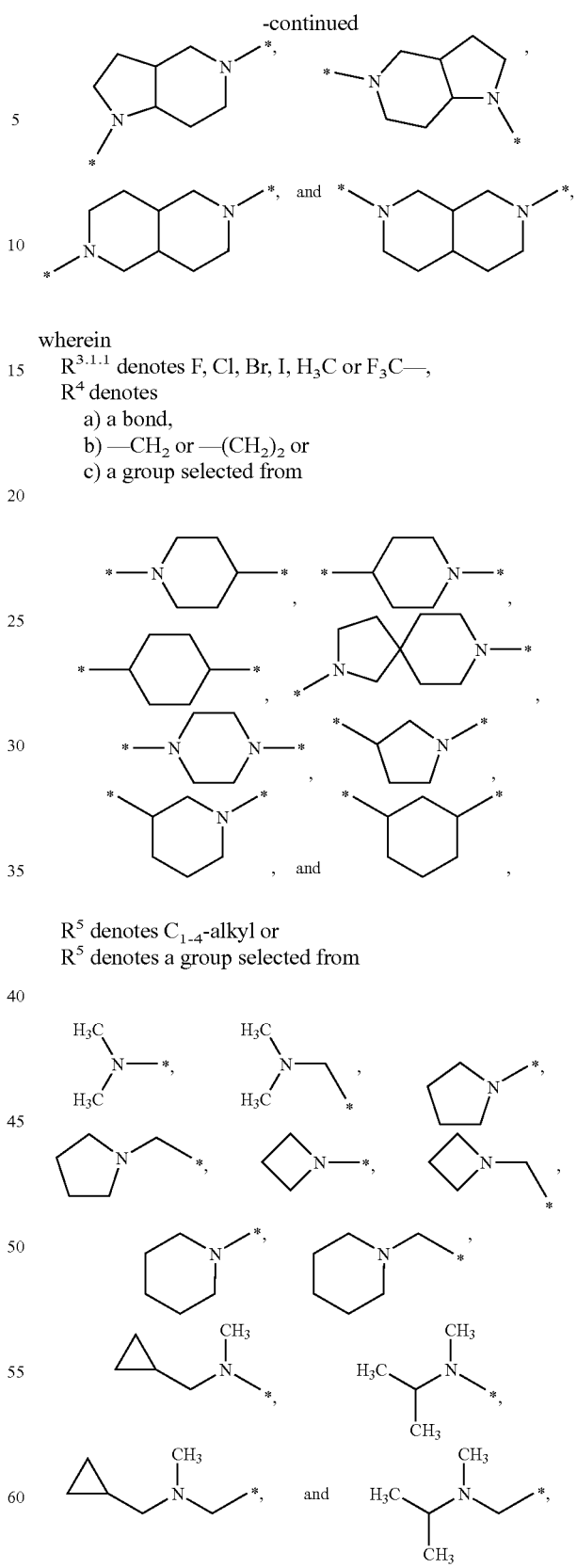
and
$R^5$ denotes $C_{1-4}$-alkyl or
$R^5$ denotes a group selected from
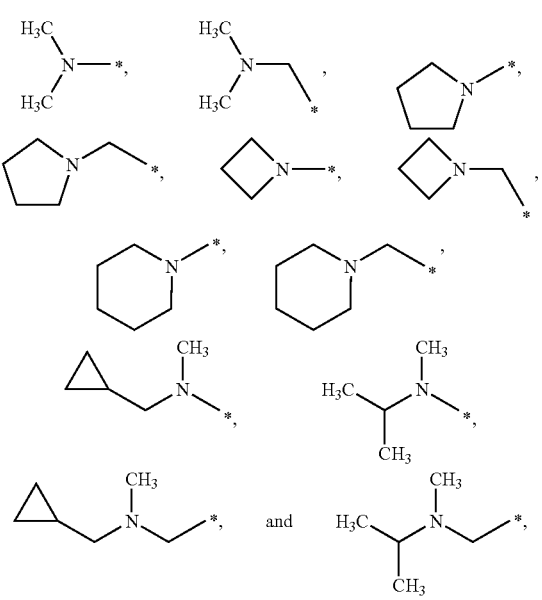
or an enantiomer, diastereomer, a mixture thereof or a physiologically acceptable salt thereof with an organic or inorganic acid or base.

18. The compound of the formula I according to claim 1, wherein

A denotes
 a) a bond,
 b) —CH$_2$ or —(CH$_2$)$_2$,
 c) —N(R$^2$),
 d) —C(O),
 e) a heterocyclic group which is selected from among

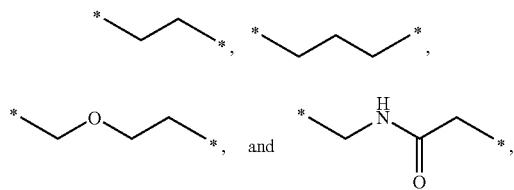

Y denotes a group selected from

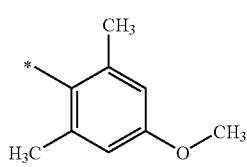

R$^1$ denotes the group

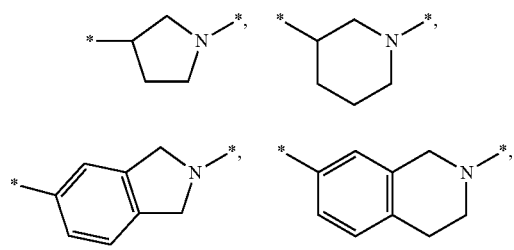

R$^2$ denotes
 a) H or
 b) H$_3$C,

R$^3$ denotes a group selected from

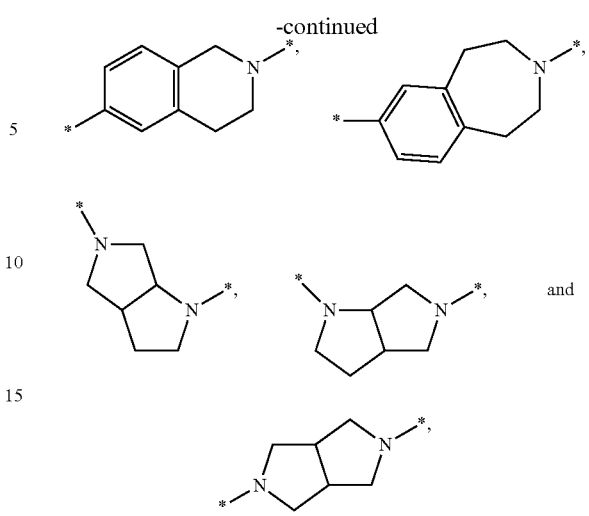

R$^4$ denotes
 a) a bond,
 b) —CH$_2$ or —(CH$_2$)$_2$ or
 b) a group selected from

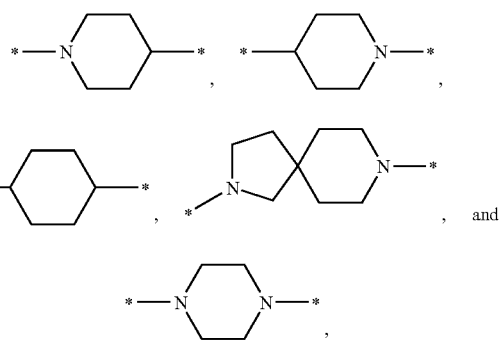

R$^5$ denotes a group selected from

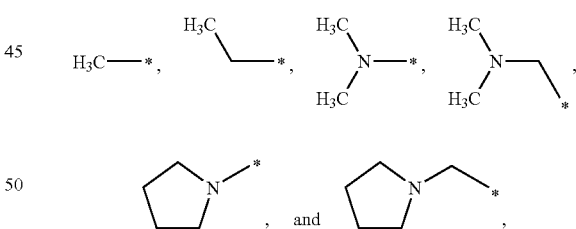

or an enantiomer, diastereomer, a mixture thereof or a physiologically acceptable salt thereof with an organic or inorganic acid or base.

19. A compound chosen from:

| Example | Structure |
|---|---|
| (1) | 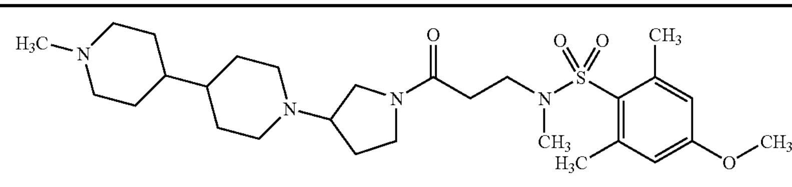 |

-continued
| Example | Structure |
|---|---|
| (2) | 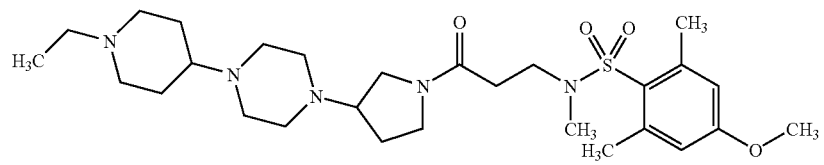 [SMILES: CCN1CCC(N2CCN(C3CCN(C(=O)CCN(C)S(=O)(=O)c4c(C)cc(OC)cc4C)C3)CC2)CC1] |
| (3) | 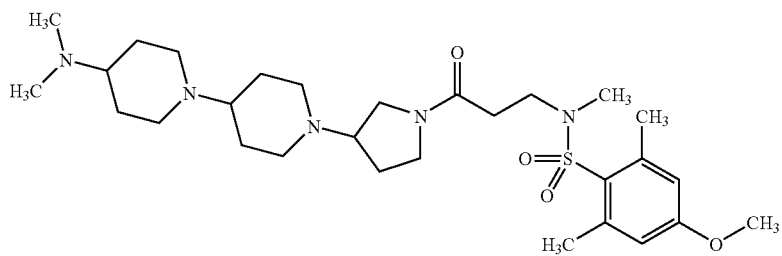 |
| (4) | 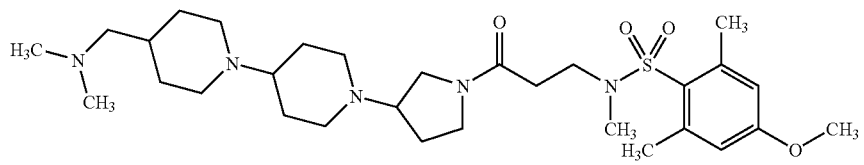 |
| (5) | 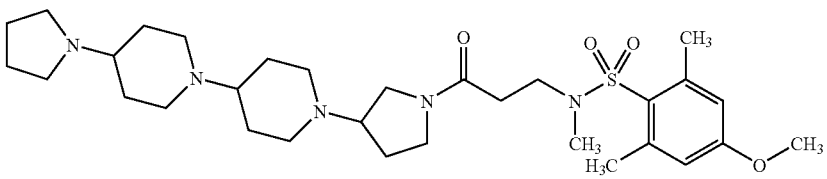 [SMILES: COc1cc(C)c(S(=O)(=O)N(C)CCC(=O)N2CCC(N3CCC(N4CCC(N5CCCC5)CC4)CC3)C2)c(C)c1] |
| (6) | 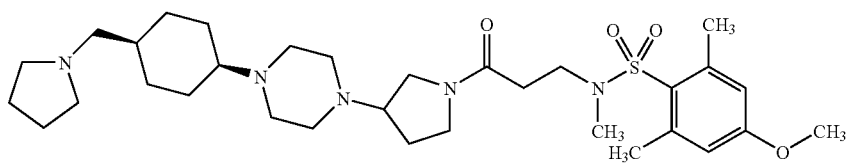 [SMILES: COc1cc(C)c(S(=O)(=O)N(C)CCC(=O)N2CCC(N3CCN([C@H]4CC[C@@H](CN5CCCC5)CC4)CC3)C2)c(C)c1] |
| (7) | 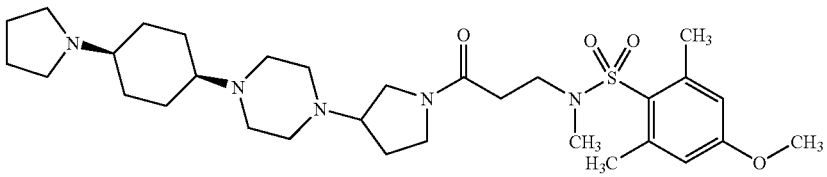 [SMILES: COc1cc(C)c(S(=O)(=O)N(C)CCC(=O)N2CCC(N3CCN([C@H]4CC[C@@H](N5CCCC5)CC4)CC3)C2)c(C)c1] |
| (8) | 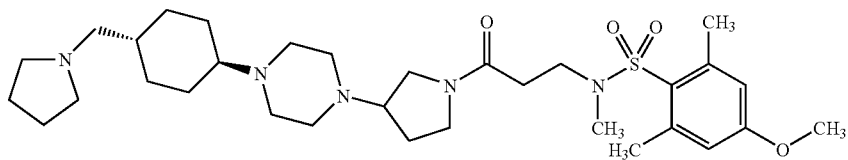 [SMILES: COc1cc(C)c(S(=O)(=O)N(C)CCC(=O)N2CCC(N3CCN([C@H]4CC[C@H](CN5CCCC5)CC4)CC3)C2)c(C)c1] |
| (9) | 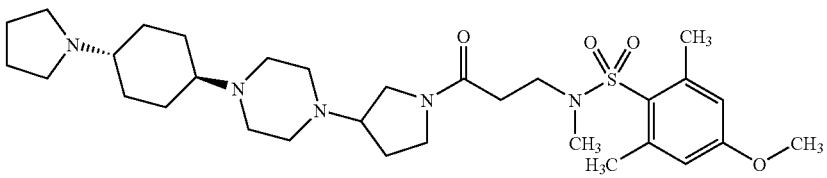 [SMILES: COc1cc(C)c(S(=O)(=O)N(C)CCC(=O)N2CCC(N3CCN([C@H]4CC[C@H](N5CCCC5)CC4)CC3)C2)c(C)c1] |

-continued
| Example | Structure |
|---|---|
| (10) | 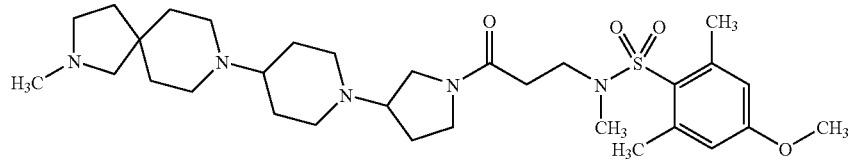 |
| (11) | 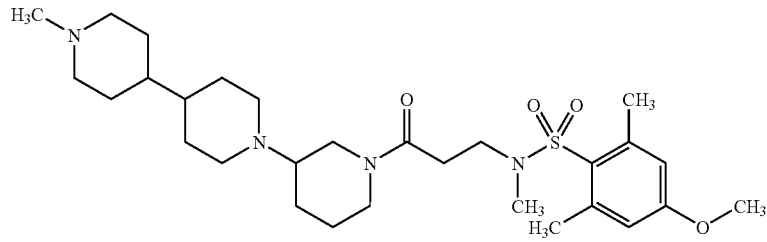 |
| (12) | 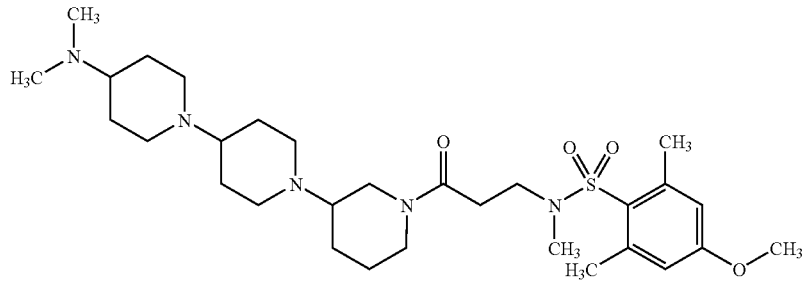 |
| (13) | 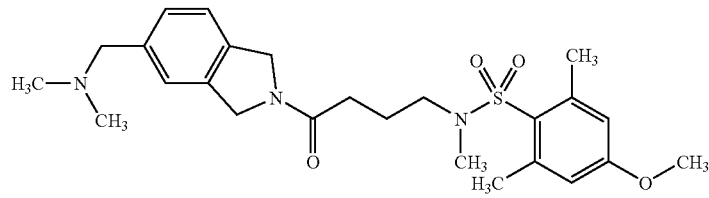 |
| (14) | 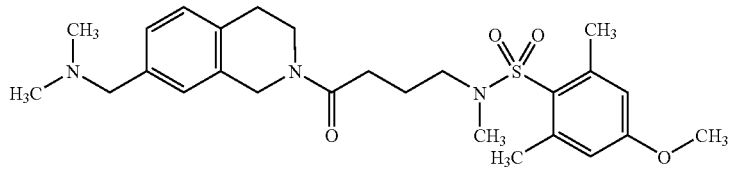 |
| (15) | 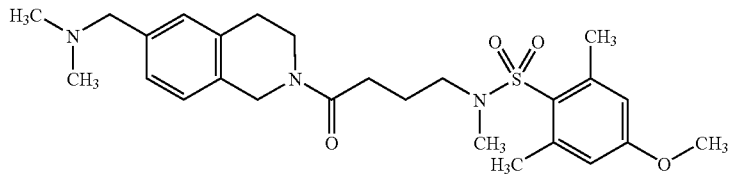 |
| (16) | 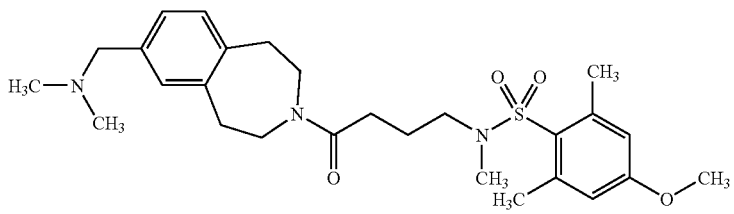 |

-continued

| Example | Structure |
|---|---|
| (17) | 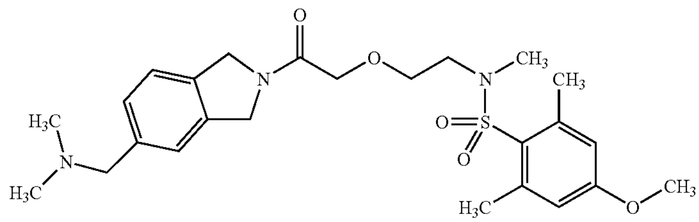 |
| (18) | 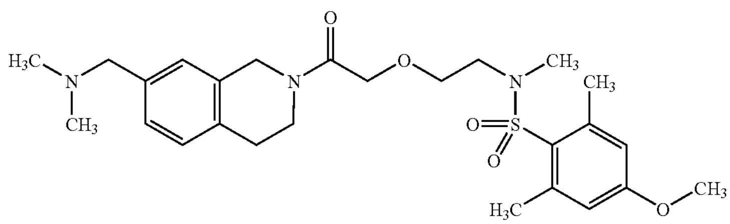 |
| (19) | 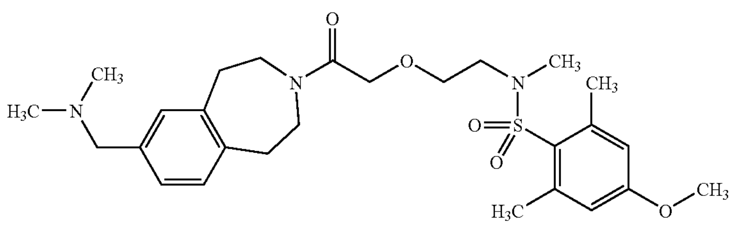 |
| (20) | 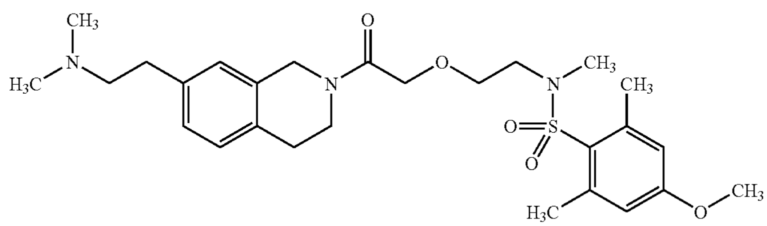 |
| (21) | Chiral |
| (22) | Chiral |
| (23) | 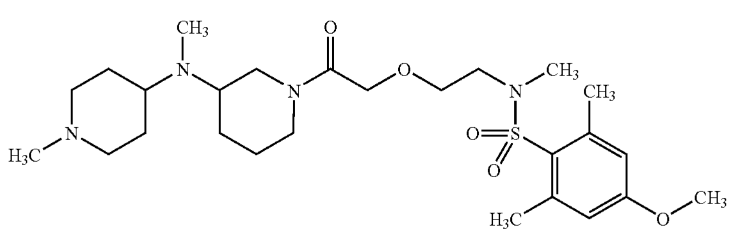 |

-continued
| Example | Structure |
|---|---|
| (24) | 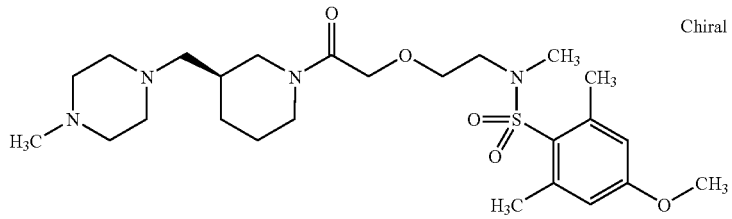 Chiral |
| (25) | 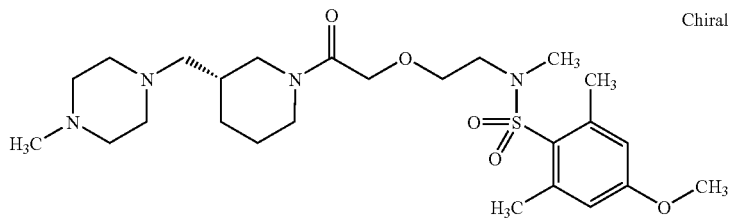 Chiral |
| (26) | 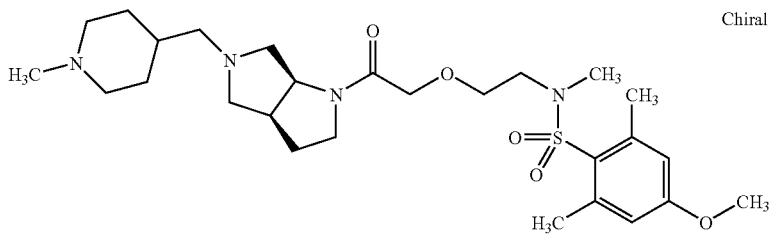 Chiral |
| (27) | 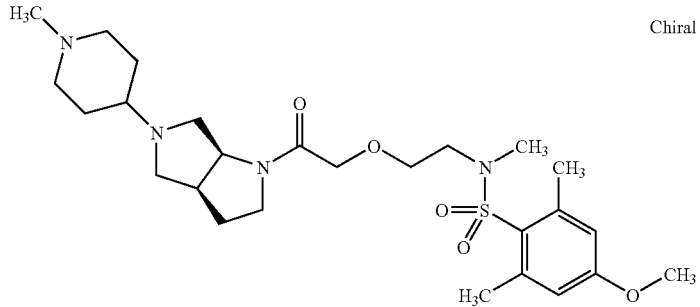 Chiral |
| (28) | 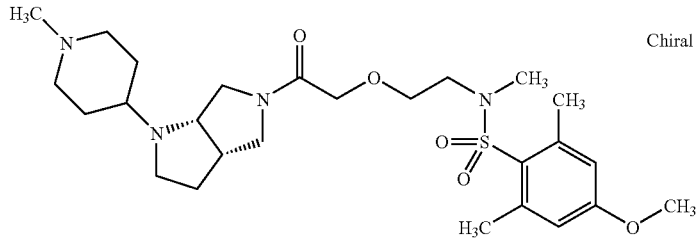 Chiral |
| (29) | 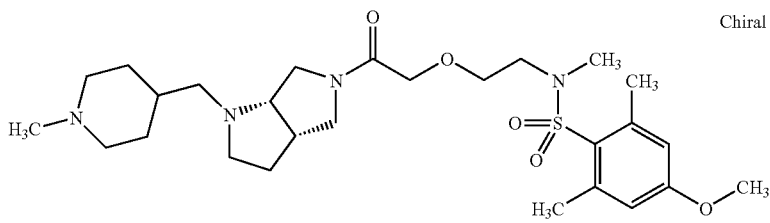 Chiral |

-continued
| Example | Structure |
|---|---|
| (30) | 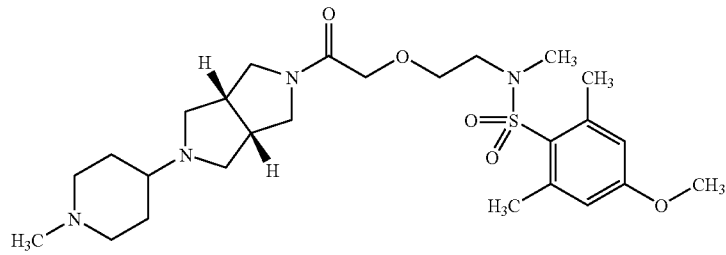 |
| (31) | 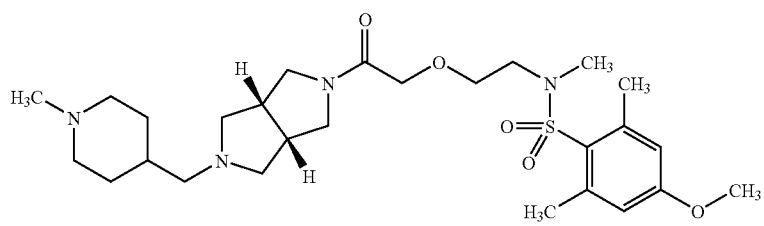 |
| (32) | 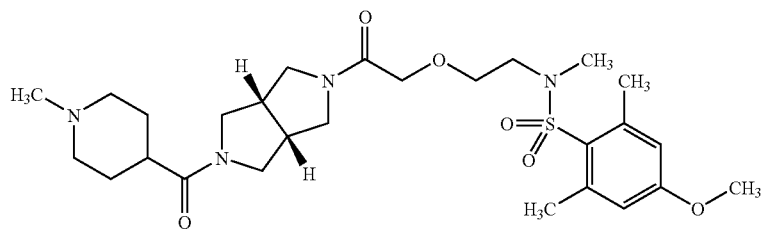 |
| (33) | 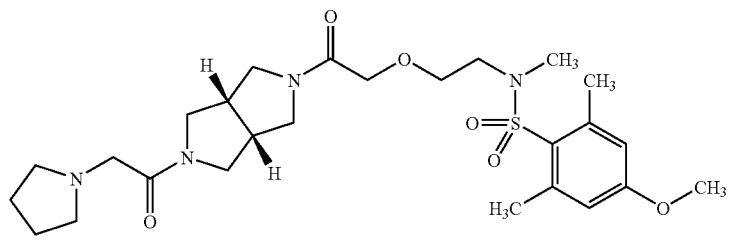 [SMILES: COc1cc(C)c(S(=O)(=O)N(C)CCOCC(=O)N2C[C@@H]3CN(C(=O)CN4CCCC4)C[C@@H]3C2)c(C)c1] |
| (34) | 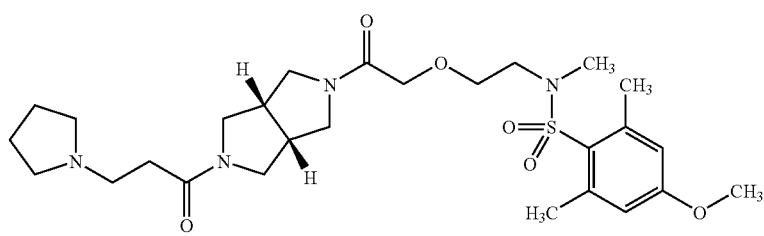 [SMILES: COc1cc(C)c(S(=O)(=O)N(C)CCOCC(=O)N2C[C@H]3CN(C(=O)CCN4CCCC4)C[C@H]3C2)c(C)c1] |
| (35) | 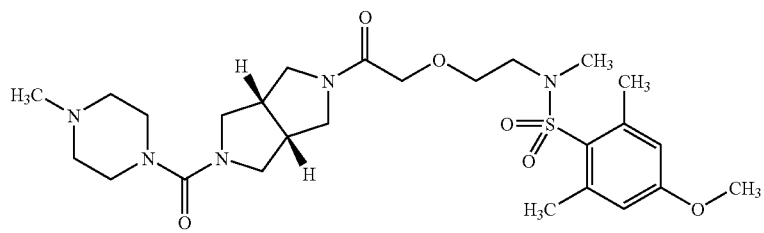 |

| Example | Structure |
|---|---|
| (36) | 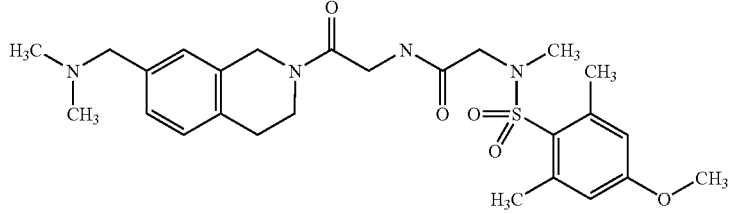 |
| (37) | 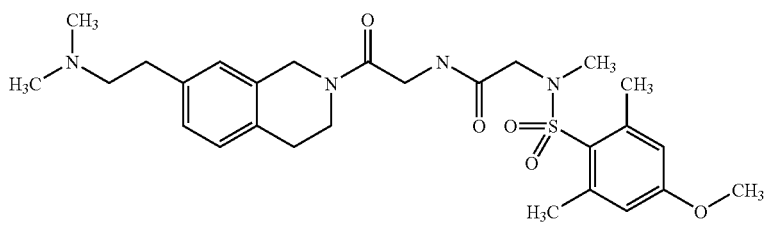 |
| (38) | 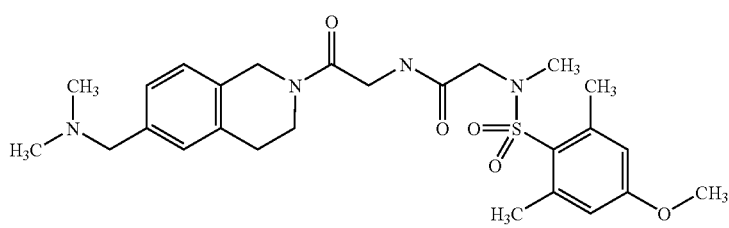 |
| | and |
| (39) | 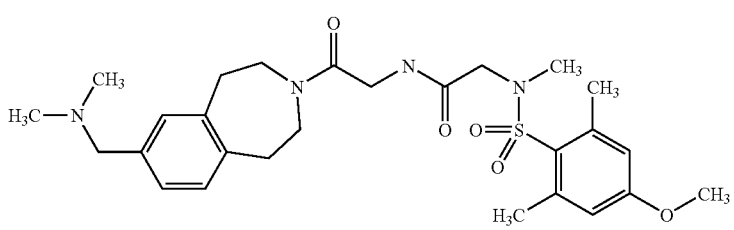 | or an enantiomer, diastereomer or physiologically acceptable salt thereof with an organic or inorganic acid or base.

20. The compound according to claim 1 wherein the salt is a physiologically acceptable salt with an inorganic or organic acid or base.

21. A pharmaceutical composition comprising a therapeutically effective amount of a compound according to claim 20 together with one or more inert carriers and/or diluents.

22. A method of treating acute pain, visceral pain, neuropathic pain, inflammatory/pain receptor-mediated pain, tumour pain or headache diseases comprising administering a therapeutically effective amount of a compound according to claim 20.

* * * * *